(12) United States Patent
Grinstaff et al.

(10) Patent No.: US 10,251,841 B2
(45) Date of Patent: Apr. 9, 2019

(54) POLYMERIC DEPOTS FOR LOCALIZATION OF AGENT TO BIOLOGICAL SITES

(71) Applicants: TRUSTEES OF BOSTON UNIVERSITY, Boston, MA (US); THE BRIGHAM AND WOMEN'S HOSPITAL, INC., Boston, MA (US)

(72) Inventors: Mark W. Grinstaff, Brookline, MA (US); Aaron H. Colby, Concord, MA (US); Yolonda Colson, Dover, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 73 days.

(21) Appl. No.: 14/351,972

(22) PCT Filed: Oct. 17, 2012

(86) PCT No.: PCT/US2012/060582
§ 371 (c)(1),
(2) Date: Apr. 15, 2014

(87) PCT Pub. No.: WO2013/059295
PCT Pub. Date: Apr. 25, 2013

(65) Prior Publication Data
US 2014/0271489 A1 Sep. 18, 2014

Related U.S. Application Data

(60) Provisional application No. 61/547,940, filed on Oct. 17, 2011.

(51) Int. Cl.
| | |
|---|---|
| *A61K 9/16* | (2006.01) |
| *A61K 31/337* | (2006.01) |
| *A61K 31/352* | (2006.01) |
| *A61K 31/519* | (2006.01) |
| *A61K 49/00* | (2006.01) |
| *A61K 9/51* | (2006.01) |
| *A61K 47/54* | (2017.01) |

(52) U.S. Cl.
CPC .......... *A61K 9/1641* (2013.01); *A61K 9/5138* (2013.01); *A61K 31/337* (2013.01); *A61K 31/352* (2013.01); *A61K 31/519* (2013.01); *A61K 47/555* (2017.08); *A61K 49/0054* (2013.01)

(58) Field of Classification Search
None
See application file for complete search history.

(56) References Cited

U.S. PATENT DOCUMENTS

| | | | |
|---|---|---|---|
| 7,671,005 B2 | 3/2010 | Mort et al. | |
| 7,671,095 B2 | 3/2010 | Colson et al. | |
| 8,334,324 B2 | 12/2012 | Colson et al. | |
| 8,338,492 B2 | 12/2012 | Colson et al. | |
| 2012/0219589 A1* | 8/2012 | Garcia De Castro Andrews ........ A61K 9/0021 424/227.1 |

OTHER PUBLICATIONS

Agrawal et al., "Evaluation of poly(L-lactic acid) as a material for intravascular polymeric stents", Biomaterials 13(3):176-182 (1992).
Athanasiou et al., "Orthopaedic Applications for PLA-PGA Biodegradable Polymers", Arthroscopy 14(7):726-737 (1998).
Attawia et al., "Cytotoxicity testing of poly(anhydride-co-imides) for orthopedic applications", J. Biomed. Mater. Res. 29:1233-1240 (1995).
Edlund et al., "Degradable Polymer Microspheres for Controlled Drug Delivery", Adv. Polymer Sci. 157:67-112 (2002).
Heller et al., "Poly(ortho esters): synthesis, characterization, properties and uses", Adv. Drug Deliv. Rev. 54:1015-1039 (2002).
Landfester et al., "Formulation and Stability Mechanisms of Polymerizable Miniennulsions", Macromolecules 32:5222-5228 (1999).
Miller et al., "On the biodegradation of poly-beta-hydroxybutyrate (PHB) homopolymer and poly-beta-hydroxybutyrate-hydroxyvalerate copolymers", Biomaterials 8:129-137 (1987).
Wang et al., "Preparation and Characterization of Poly(lactic-co-glycolic acid) Microspheres for Targeted Delivery of a Novel Anticancer Agent, Taxol", Chem. Pharm. Bull. 44(10):1935-1940 (1996).
Zubris et al., "Hydrogels as Intracellular Depots for Drug Delivery", Mol. Pharm. 9:196-200 (2012).

* cited by examiner

*Primary Examiner* — James W Rogers
(74) *Attorney, Agent, or Firm* — Ronald I. Eisenstein; Nixon Peabody LLP

(57) ABSTRACT

Provided herein are polymeric particles and compounds and processes that can be used to prepare polymer-based particles and methods of using those particles to localize or concentrate a subsequently delivered agent to an in vivo site.

13 Claims, 16 Drawing Sheets

POLYMERIC DEPOTS FOR LOCALIZATION OF AGENT TO BIOLOGICAL SITES

RELATED APPLICATIONS

This application is a 35 U.S.C § 371 National Phase Entry Application of International Application No. PCT/US2012/060582 filed Oct. 17, 2012, which designates the U.S., and which claims benefit under 35 U.S.C. § 119(e) of the U.S. Provisional Application No. 61/547,940, filed Oct. 17, 2012, the content of which is incorporated herein by reference in its entirety.

GOVERNMENT SUPPORT

This invention was made with Government Support under Contract No. DMR-1006601 awarded by the National Science Foundation and Contract No. W81XWH-09-2-0001 awarded by the Department of the Army. The Government has certain rights in the invention.

FIELD OF THE INVENTION

Provided herein are polymer particle compositions, compounds, processes, and methods of use of the polymer particles that localize to a tissue site and then target and concentrate a subsequently delivered agent to the site.

BACKGROUND OF THE INVENTION

Medicine traditionally utilizes pharmacologic agents or surgical interventions for the treatment of disease. Specific targeting or localization of pharmacologic or biologic agents to desired organs and tissues is a complex challenge.

For example, delivery of agents to tumors to treat or cure cancer is limited by non-specific targeting, agent degradation, and high systemic toxicity, to name a few. Treatments of conditions such as cancer remain relatively ineffective as evidenced by high rates of cancer recurrence and low survival; cancer is a leading cause of death for both men and women in the United States (Jemal et al., CA Cancer J. Clin., 60:277-300, 2010). Current methods of cancer treatment include chemotherapy, radiation treatment, and surgical resection.

Other medical applications which utilize drug delivery technologies include immunological applications, pain control, wound healing, infectious disease, transplants, and the development of vaccines. Potential drug candidates often present solubility, toxicity, and/or pharmacokinetic concerns. Thus, there is a broad need for locally and regionally targeted and sustained delivery of therapeutic agents.

Certain polyesters, polycarbonates, and polyamides are biodegradable polymers with low toxicity and degradation properties. Such polymers include poly(ε-caprolactone), poly(p-dioxanone), poly(trimethylene carbonate), and most notably poly(glycolic acid) and poly(lactic acid)(see, e.g., Agrawal et al., Biomaterials, 13:176-182, 1992; Attawia et al., J. Biomed. Mater. Res., 29:1233-140, 1995; Heller et al., Adv. Drug Deliv. Rev., 54:1015-1039, 2002; Miller and Williams, Biomaterials, 8:129-137, 1987; and Athanasiou et al., Arthroscopy, 14:726-737, 1998). These polymers are used in a variety of applications including the delivery of therapeutic agents. However, physical properties of the aforementioned polymers are limited by monomer selection, polymerization techniques and post-polymerization modifications. Properties of interest include thermal transition temperatures, bulk strength, flexibility or elasticity, degradation, crystallinity, and hydrophobicity. When polymers are utilized for in vivo applications, the physical properties of the material affect host response.

Hence, a need exists for polymers and delivery systems with desired characteristics that are effective for treatment of diseases and conditions in vivo and that can be tailored for specific therapeutic needs and tissue characteristics.

SUMMARY OF THE INVENTION

The invention is based, at least in part, on the discovery that polymeric particles can be used for the controlled, localized, sustained delivery of various agents for treatment of diseases and conditions. The inventors have discovered inter alia that polymeric particles can localize to a site in vivo after administration and can concentrate or localize, at that site, an agent that is delivered prior to, simultaneously with, or subsequent to the polymeric particles. Such a delivery system reduces systemic exposure of the agent and increases the local concentration of the agent at the desired site. Further, the agent can be administered once or multiple times to obtain repeated high concentrations of the agent at the site for increased efficacy.

Thus, in one aspect, the present disclosure provides methods and processes for concentrating, localizing or delivering an agent to a desired site or location. Generally, the method comprises providing one or more empty polymeric particles to the site, and the agent that needs to be concentrated or localized is delivered prior to, simultaneously with or after providing the empty polymeric particles to the site. The polymeric particle can undergo a change in volume when coming in contact with the desired site or location and become localized at that site or location. Without wishing to be bound by a theory, the polymeric particle can uptake the agent that is delivered without the polymeric particle. In some embodiments, the polymeric particle is capable of localizing or concentrating an agent in a tissue in vivo.

The method described herein is novel and non-obvious over the methods currently used in the art for delivering an agent using particles. The methods currently employed in the art comprise preloading the particle with agent to be delivered before delivering the particle to the desired site. Accordingly, the particle can be said to transferring the agent to the desired site. However, in the method described herein, the particle is delivered to the desired site without the agent. The agent can be delivered prior to, simultaneously with or after providing the polymeric particle to the site. Thus, the polymeric particle is acting as a depot for concentrating or localizing the agent at the desired site.

Without limitations, the method can be used to concentrate or localize the agent at a desired site in vitro, ex vivo or in vivo. Further, the desired site can be a cell, a tissue, or an organ. Exemplary sites can include, but are not limited to, specific cell types, a tissue, an organ, a lymph node, an established tumor, and the remains of a tumor from a surgically resected tumor, etc. . . . . The desired site can also be sites of inflammation or specific organs or biologic locations or sites of pathologic processes such as inflammation, such as in joints, where increased local drug concentrations are desired. In some embodiments, the desired site can be a tumor, a lymph node, airways, a cavity or a capillary, or any combination thereof. In some embodiments, the site of interest can be a tissue location selected from the group consisting of a tumor, a surgical resection margin at a treated or untreated tumor or cavity, within a treated or untreated tumor or cavity, a target site of disease away from a surgical margin, a target site of disease away from a tumor, a lymph node, within an airway or lumen, and within an organ. In some embodiments, the site of interest can be selected from the group consisting of lymph node, colon, small intestine, large intestine, bladder, ovary, urethra, uterus, breast, prostate, thyroid gland, stomach, kidney, liver, heart, or brain.

In some embodiments, the polymeric particles are delivered to an endocrine, an intrathoracic or an intraabdominal organ or a combination thereof.

For in vivo application, the empty polymeric particles and the agent can be administered to a subject. For example, the empty polymeric particles can be administered locally to the desired site or location, e.g., tissue or organ. The agent can be administered locally or systemically.

The method described herein can be used to deliver any agent by concentrating it at a specific site. The agent can be in any pharmaceutically acceptable form of an agent, including pharmaceutically acceptable salts. A large number of pharmaceutical agents are known in the art and are amenable for use in the method described herein. Acceptable agents include, but are not limited to, chemotherapeutic agents, such as radiosensitizers, receptor inhibitors and agonists or other anti-neoplastic agents; immune modulators, anti-inflammatory agents, and bioactive agents, such as cytokines, growth factors, or steroids with or without the co-incorporation of tumor or pathogen antigens to increase the antineoplastic response as a means of vaccine development; local anesthetic agents; antibiotics; or nucleic acids as a means of local gene therapy.

In some embodiments, the agent can be a bioactive agent or a therapeutic agent.

In some embodiments, agent can be an anticancer agent, an immune modulator agent, an anti-inflammatory agent, an antibiotic, or any combinations thereof.

In some embodiments, the agent can be selected from the group consisting of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel; doxorubicin; etoposide; floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed; pentostatin; plicamycin; procarbazine; rituximab; streptozocin; teniposide; thioguanine; thiotepa; vinblastine; vincristine; vinorelbine; 10-hydrocamptothecin and derivatives thereof and any combinations thereof.

In some embodiments, the agent is paclitaxel.

In some embodiments, the agent can be in the form of a microparticle or a nanoparticle, i.e., a particle having a diameter from about 1 nm to about 10 microns, e.g., a diameter from about 2 nm to about 1 micron. Accordingly, in some embodiments, the polymeric particle can comprises a nanoparticle of size about 1 nm to about 1000 nm, a microparticle of size about 1000 nm to about 10 micron, or a larger microparticle of size about >10 microns.

The polymeric particle can be targeted or localized to the desired site using any technique or method available to and known to the skilled artisan. For example, the polymeric particles can be targeted and localized to a specific site using targeting ligands. However, other physical or chemical methods can also be employed to target the particles to the desired site. For example, the polymeric particles can be coated with PLURONIC® F127, or the particles can be entrapped within a gel, hydrogel, adhesive, or sealant to increase there resident time at the implant site.

In some embodiments, the particles can swell and become lodged, embedded, entrapped, or otherwise immobilized at a certain target location. For example, swelled particles can become lodged or embedded within a specific tissue, organ, cavity, node, tubule, bronchus or capillary and can be used to occlude blood flow as an embolization agent for bleeding, arteriovenous malformations, or tumor devascularization or can be used to prevent airflow to a specific portion of the lung as for endoscopic lung volume reduction surgery, to cite only two examples of potential uses of this property. The resulting particle in the cell or tissue site can be used as a depot to concentrate agent that has been subsequently delivered.

Accordingly, in some embodiments, the polymeric particles undergo a change in volume at the desired site. Stated in other way, the polymeric particles can comprise a first volume while not in contact with the desired site and a second volume when in contact with the desired site. The first and second volumes can different from each other by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 1.1 folds, at least 1.2 folds, at least 1.25 folds, at least 1.5 folds, at least 1.75 folds, at least 2 folds, at least 3 folds, at least 4 folds, at least 5 folds, at least 6 folds, at least 7 folds, at least 8 folds, at least 9 folds, or at least 10 folds. Generally, the first volume can be smaller than the second volume, i.e., the volume of the particle increases after becoming in contact with the desired site. Stated another way, the particles swell after becoming in contact with the desired site. Without wishing to be bound by a theory, the change in volume allows the polymeric particle to become lodged, embedded, immobilized or entrapped at the desired site, e.g. in an anatomical location of the tissue. If desired or needed, the amount of volume changes can be controlled by cross-linking the polymers or oligomers in the particles.

In some embodiments, polymeric particle can under go a change in volume due to changes in pH, salt concentration, temperature, pressure, light, cleavage of one or more molecules making the particle, or temperature, upon becoming in contact with the desired site. Accordingly, in some embodiments, the polymeric particle comprises a pH-sensitive, a photo-sensitive or a thermosensitive monomer, and the polymeric particle can undergo a change in volume on contact with the tissue and becomes lodged, embedded, immobilized or entrapped at the desired site, e.g., in an anatomical location of a tissue.

In some embodiments, particle swelling can be triggered by pH change from an exogenous agent added to the polymer comprised in the polymeric particles, a change within a cavity or vessel as can occur in ischemic or infected tissues or within an intracellular compartment such as an endosome. Such particles can also be manufactured to deliver agents that manipulate healing or fibrosis to facilitate permanent or temporary closure of the occluded lumen or cavity. In some embodiments, the polymeric particle can undergo a change in volume of 1×, 1.1× or more when the pH is acidic.

The polymeric particles can comprise oligomers, polymers, macromolecules or copolymers which contain alkyl side chains formed between [1] a monomer or macromolecular unit containing at least one functional side group; [2] alkyl chains containing 1-50 carbon units; and, in some embodiments, [3] a structurally different monomer or macromolecular unit. In some embodiments, the macromolecular materials can be elastic solids or viscoelastic solids. In some embodiments, the macromolecular material can be hydrophobic or hydrophilic. In some other embodiments, the macromolecular material undergoes a change from hydrophobic to hydrophilic in response to a change in pH, temperature, or light exposure. In some embodiments, the macromolecular material can swell to a size that leads to an expanded state in the cell or surrounding tissue. This expanded state or hydrogel state can act then act a drug depot for agents by concentrating the agent at the site after IP, IV, SQ, IM, inhaled, rectal or oral administration.

In some embodiments, the polymeric particles can be provided in aqueous or organic solutions, or combinations thereof. Examples of the aqueous solutions include but are not limited to water, buffered aqueous media, saline, buffered saline, solutions of amino acids, solutions of sugars, solutions of vitamins, solutions of carbohydrates or combinations of any two or more thereof. Examples of the organic solutions include but are not limited to DMSO, ethanol, methanol, tetrahydrofuran (THF), dichloromethane, dimethylformamide (DMF), hexane or toluene or combinations of any two or more thereof.

In some embodiments, the polymeric particle comprises a core that is more hydrophobic than the aqueous solution it is suspended. This can allow the particle to become localized into a tissue site and concentrating a subsequently delivered agent.

In some embodiments, the polymeric particle is a particle described in or comprises an oligomer or polymer described in U.S. Pat. No. 7,671,095 and U.S. patent application Ser. No. 12/690,607, filed Jan. 20, 2010 and Ser. No. 12/818,693, filed Jun. 18, 2010, contents of all of which are incorporated herein by reference in their entireties.

Further provided herein are compounds and processes for preparing polymer based particles, gels and related compositions.

BRIEF DESCRIPTION OF THE DRAWINGS

This patent or application file contains at least one drawing executed in color. Copies of this patent or patent application publication with color drawing will be provided by the Office upon request and payment of the necessary fee.

DETAILED DESCRIPTION OF THE INVENTION

Figure 1:
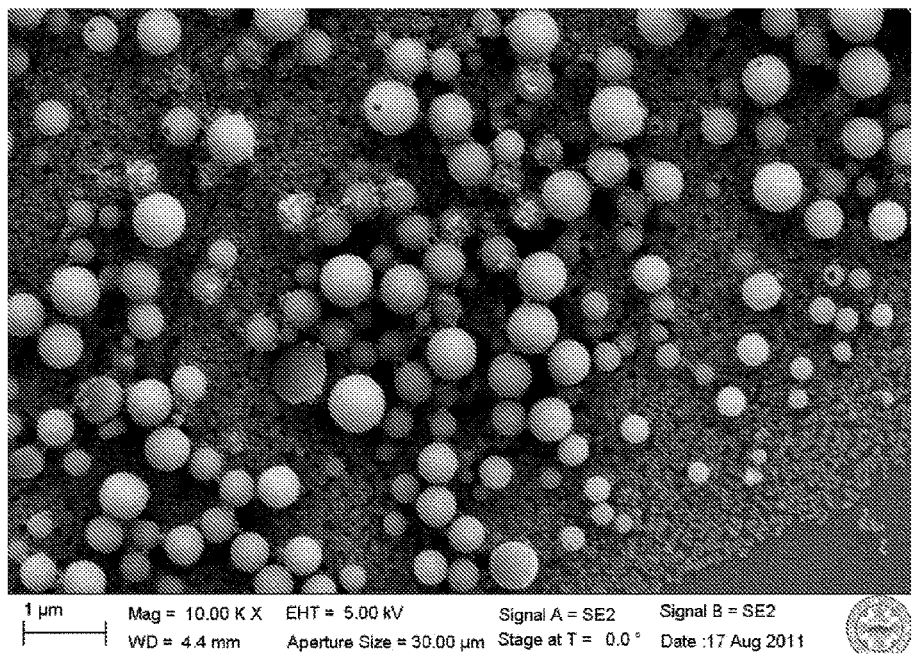
FIG. 1 shows a scanning electron microscope (SEM) image of nanoparticles.

Provided herein are methods and processes for concentrating, localizing or delivering an agent to a desired site or location. Generally, the method comprises providing one or more empty polymeric particles to the site, and the agent that needs to be concentrated or localized is delivered prior to, simultaneously with or after providing the empty polymeric particles to the site. The polymeric particle can undergo a change in volume when coming in contact with the desired site or location and become localized at that site or location. Without wishing to be bound by a theory, the polymeric particle can uptake the agent that is delivered without the polymeric particle, thereby concentrating or localizing the agent at the desired site or location. For example, empty polymeric particle can be administered to a patient affected with a tumor, the particle localizes at a tumor site, a drug, such as a chemotherapeutic drug, e.g., paclitaxel, can be subsequently administered, and the drug concentrates at the location of the delivered particles. The drug can be administered once or multiple times to obtain repeated high concentrations of the drug at the tumor site for increased efficacy.

The method described herein is novel and non-obvious over the methods currently used in the art for delivering an agent using particles. The methods currently employed in the art comprise preloading the particle with agent to be delivered before delivering the particle to the desired site. Accordingly, the particle can be said to transferring the agent to the desired site. However, in the method described herein, the particle is delivered to the desired site without the agent. The agent can be delivered prior to, simultaneously with or after providing the polymeric particle to the site. Thus, the polymeric particle is acting as a depot for concentrating or localizing the agent at the desired site.

As used herein, the term "empty particle" refers to particles that lack the agent to be delivered, concentrated or localized to the site of interest. Thus, empty particle do not transfer the agent to the desired site but concentrate the agent at the desired site. While the empty particle lacks the agent to be delivered, the particle can include it a second or different agent. This can be useful for delivering two or more different agents to a site without having to formulate the agents in the same composition. For example, a first agent can be included in the polymeric particles that can be delivered to the desired site prior to, simultaneously with or after providing a second agent to the site. Thus, when two or more different agents are to be delivered, the term "empty particle" refers to particles that lack at least one of the agents to be delivered, concentrated or localized to the site of interest. Lesser amounts can be used to achieve efficacious levels of treatment for certain biologically active substances.

While the empty particle generally lacks any amount of the agent to be delivered to the site, in some embodiments, the empty particle can comprise some small amount of the agent to be localized or concentrated. This can be useful for delivering an initial small amount of the agent to check for toxicity or adverse reactions. If no or little toxicity or adversity to the agent is seen, a higher dosage of the agent can be delivered to the site. In some embodiments, the empty particle can comprise less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 50%, or 60% of the total amount of agent to be delivered. In some embodiments, less than 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 30%, 35%, 40%, 50%, or 60% of the empty particles include the agent which is to concentrated at the site.

Without limitations, the polymeric particle can be of any size, shape or form, e.g., spherical, rod, elliptical, cylindrical, capsule, or disc. In some embodiments, the particle can be a microparticle or a nanoparticle. As used herein, the term "microparticle" refers to a particle having a particle size of about 1 µm to about 1000 µm. In some embodiments, the microparticle as a size of about 5 µm to about 750 µm, about 10 µm to about 500 µm, about 25 µm to about 250 µm, or about 50 µm to about 100 µm. As used herein, the term "nanoparticle" refers to particle having a particle size of about 1 nm to about 1000 nm. For example, a nanoparticle can have a particle size of about 5 nm to about 750 nm, about 10 nm to about 500 nm, about 15 nm to about 250 nm, or about 20 nm to about 100 nm. In some embodiments, the particle can have a diameter about 2 nm to 100 nm, from about 0.002 micrometers to about 10 micrometeres, or from about 1 micrometer to about 50 micrometers.

When the polymer nanoparticle swells and expands the size will be larger with a preferable size of between 10 and 1000 nm. Other polymeric particles of these sizes or larger can be useful at specific sites, such as an established tumor or where tumor regrowth is prevalent. For example, at a surgical margin, where suturing or stapling has occurred, or within an established or treated tumor such as an ablated cavity secondary to radiofrequency ablation or other therapy, or within a spontaneous cavity such as occurs in squamous cell carcinoma. Placement of polymeric particles within pathologic cavities or biologic spaces (i.e. pleural or peritoneal spaces) could be utilized to treat abscess cavities with antibiotics or to result in sclerosis of the cavity, either with release of specific sclerosing agents such as talc powder, alcohol or doxycyclin as examples or other inflammatory agents. This approach can then be utilized in the treatment of bullous disease in emphysema or infectious diseases such as ecchinococcal cysts for example.

It will be understood by one of ordinary skill in the art that particles usually exhibit a distribution of particle sizes around the indicated "size." Unless otherwise stated, the term "size" as used herein refers to the mode of a size distribution of particles, i.e., the value that occurs most frequently in the size distribution. Methods for measuring the particle size are known to a skilled artisan, e.g., by dynamic light scattering (such as photocorrelation spectroscopy, laser diffraction, low-angle laser light scattering (LALLS), and medium-angle laser light scattering (MALLS)), light obscuration methods (such as Coulter analysis method), or other techniques (such as rheology, and light or electron microscopy).

In some embodiments, the particle can be substantially spherical. What is meant by "substantially spherical" is that the ratio of the lengths of the longest to the shortest perpendicular axes of the particle cross section is less than or equal to about 1.5. Substantially spherical does not require a line of symmetry. Further, the particles can have surface texturing, such as lines or indentations or protuberances that are small in scale when compared to the overall size of the particle and still be substantially spherical. In some embodiments, the ratio of lengths between the longest and shortest axes of the particle is less than or equal to about 1.5, less than or equal to about 1.45, less than or equal to about 1.4, less than or equal to about 1.35, less than or equal to about 1.30 less than or equal to about 1.25 less than or equal to about 1.20 less than or equal to about 1.15 less than or equal to about 1.1. Without wishing to be bound by a theory, surface contact is minimized in particles that are substantially spherical, which minimizes the undesirable agglomeration of the particles upon storage. Many crystals or flakes have flat surfaces that can allow large surface contact areas where agglomeration can occur by ionic or non-ionic interactions. A sphere permits contact over a much smaller area.

In some embodiments, the particles have substantially the same particle size. Particles having a broad size distribution where there are both relatively big and small particles allow for the smaller particles to fill in the gaps between the larger particles, thereby creating new contact surfaces. A broad size distribution can result in larger spheres by creating many contact opportunities for binding agglomeration. The particles described herein are within a narrow size distribution, thereby minimizing opportunities for contact agglomeration. What is meant by a "narrow size distribution" is a particle size distribution that has a ratio of the volume diameter of the 90th percentile of the small spherical particles to the volume diameter of the 10th percentile less than or equal to 5. In some embodiments, the volume diameter of the 90th percentile of the small spherical particles to the volume diameter of the 10th percentile is less than or equal to 4.5, less than or equal to 4, less than or equal to 3.5, less than or equal to 3, less than or equal to 2.5, less than or equal to 2, less than or equal to 1.5, less than or equal to 1.45, less than or equal to 1.40, less than or equal to 1.35, less than or equal to 1.3, less than or equal to 1.25, less than or equal to 1.20, less than or equal to 1.15, or less than or equal to 1.1.

The amount of agent concentrated or localized at the desired site will depend on the therapeutic range of the drug, its toxicity when and how it is delivered, and the clinical characteristics of the patient being treated as well as the interaction between the polymer nanoparticle and the agent which concentrates therein. As used herein, the term "concentrate" in reference to concentrating an agent at a desired site means that amount of the agent at the desired site is higher than relative to when no polymeric particles are present at the site. For example, the amount of the agent at the desired site is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 1.1 folds, at least 1.2 folds, at least 1.25 folds, at least 1.5 folds, at least 1.75 folds, at least 2 folds, at least 3 folds, at least 4 folds, at least 5 folds, at least 6 folds, at least 7 folds, at least 8 folds, at least 9 folds, or at least 10 folds higher when polymeric particles is present at the site relative to when no polymeric particles are present.

As used herein, the term "localize" in reference to localizing an agent at a desired site means that amount of the agent at the desired site is higher than relative to when no polymeric particles are present at the site. For example, the amount of the agent at the desired site is at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 1-fold, at least 1.1 folds, at least 1.2 folds, at least 1.25 folds, at least 1.5 folds, at least 1.75 folds, at least 2 folds, at least 3 folds, at least 4 folds, at least 5 folds, at least 6 folds, at least 7 folds, at least 8 folds, at least 9 folds, or at least 10 folds higher when polymeric particles is present at the site relative to when no polymeric particles are present.

In some embodiments, the amount of the agent localized or concentrated at the desire site is a therapeutically effective amount of the agent. As used herein, the term "therapeutically effective amount" refers to an amount of a compound sufficient to achieve a therapeutic effect. Therapeutic effect can be, e.g., reduction is tumor size, reduction in the amount of a disease marker or partial normalization of other laboratory test, such as a urine analysis or blood chemistry for any particular disease or disorder, reduction in swelling, or subjective reduction in pain experienced by the subject.

The number of particles delivered to a site is selected depending on factors such as 1) the amount of agent delivered per particle, 2) the therapeutic range of the agent, 3) the local toxicity of the agent, and 4) the clinical characteristics of the subject being treated. The development of dosages based on these parameters is routinely performed by those skilled in the art of pharmacology and clinical medicine. For example, between $1\times10^4$ and $1\times10^{12}$ particles/cm can be delivered or administered to the desired site, e.g., a biological area.

The method can be used for in vitro and in vivo local drug concentration. Depending upon the selected polymeric particle, the rate of drug release can be delayed or immediate. In some embodiments, the polymeric particles can be used for prolonged drug delivery after an initial period of quiescence to permit surgical healing to occur.

The method provided herein can be utilized to promote healing or prevent disease by targeting prophylactic or therapeutic drugs to local and/or regional areas. The method an also be used in imaging, such as diagnostic imaging of tumors or residual tumor cells, for example, to see tumor cells for surgical debulking of small amounts of tumor. The method described herein can be utilized to diagnose disease, promote healing or prevent disease by targeting or concentrating a drug or diagnositic molecule to local and regional areas. The method described herein can be used for a variety of applications including, but not limited to, repair an injured tissue, organ, bone, or genetic defect. Other uses include treatment of early, late or previously treated malignancies, pre-treatment of malignancies or other condition as a sensitizer to augment therapy of another agent such as with radiation sensitizers, avoidance of locoregional lymph node metastasis, augmentation of local wound healing and decrease in infection, manipulation of structure and abnormal scar formation, delivery of drugs, cytokines or steroids—into, for example, joint capsules—insulin, glucagon, or genetically missing enzymes and for the treatment of post-operative pain. The method described herein can also be used for a variety of other applications including, but not limited to repair of an injured or malformed tissue, organ, bone, or amelioration of genetic defect.

Accordingly, provided herein are methods of treatment of diseases and disorders comprising the step of delivering empty polymeric particles to a specific tissue location wherein a therapeutic agent is desired to be delivered. The drug for treatment can be delivered prior to, simultaneously with, or subsequent to the polymeric particles.

In some embodiments, the method comprises administering one or more empty polymeric particles to a subject prior to, simultaneously with or after administering the therapeutic agent or a diagnostic agent to the subject.

In some embodiments, the polymer particle is delivered first to the tissue site and the agent is administered subsequently, wherein the agent concentrates at the site of the polymer particle, thus delivering a targeted treatment of the tissue or location wherein the polymer particles have been delivered.

As used herein, the term "administered" refers to the placement of the polymeric particles or the agent into a subject by a method or route which results in at least partial localization of the particles or the agent at a desired site. Without limitations, the in vivo administration can be by any appropriate route which results in some localization of the the particles or the agent at the desired site in the subject, i.e., administration results in delivery to a desired location in the subject where at least some amount or portion of the polymeric particles or the agent is delivered. Exemplary modes of administration include, but are not limited to, implant, injection, infusion, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. Further, the administration can be local or systemic. By local administration is meant the the administration is local to the desired sire, i.e., administration is within or around the desired site. By systemic administration is meant non-local administration.

In some embodiments, the polymeric particles can be administered locally. For example, the polymeric particles can be injected or infused into or around inoperable tumors to locally deliver drugs, such as chemotherapy, immunomodulators, or sensitizers etc, or injected/infused near the site of the operative incision, such as antibiotics, anesthetics or growth/healing factors, thereby avoiding side effects associated with systemic delivery. The polymeric particles can also be administered locally at a site of surgery to treat local residual tumor cells and to be carried by the lymph fluid to locoregional nodes. The particles can become trapped at the lymph nodes, allowing delivery of agents to tumor cells that also commonly migrate to lymph nodes. Cells that commonly migrate to lymph nodes include tumor cells and immune cells such as T cells or dendritic cells, and thus direct presentation of antigens, immunomodulating agents etc., by the particles can be used to enhance the immune system. Thus, the particles can be used to treat tumors systemically either by targeting the tumor cells directly of by upregulating the immune system to fight the tumor. In some embodiments, the empty polymeric particles can be implanted at the desired site. The particles can be encapsulated in a matrix, e.g. a matrix comprising a biocompatible or biodegradable polymer.

For administering the agent, the agent can be administered locally near the location of the particles or systemically, allowing it to concentrate to the location of the polymeric particles.

Without limitations, the empty polymeric particles and the agent can be administered within any required period of time. What is meant by this is that the time period between administration of the polymeric particles and the agent can be any desired amount of time. For example, the empty polymeric particles and the agent can be administered within seconds, minutes, hours, or days of each other. In some embodiments, the empty polymeric particles and the agent can be administered within 1 week, 6 days, 5, days, 4 days, 3 days, 2 days, 24 hours, 18 hours, 12 hours, 11, hours, 10 hours, 9 hours, 8 hours, 7 hours, 6 hours, 5 hours, 4 hours, 1 hours, 60 minutes, 45 minutes, 30 minutes, 25 minutes, 20 minutes, 15 minutes, 10 minutes, 5 minutes, 60 seconds, 45 seconds, 30 seconds of 15 seconds of each other. Further, either the polymeric particles or the agent can be administered first. In some embodiments, the polymeric particles can be administered first.

For administration to a subject, the polymeric particles and/or the agent can can be formulated in pharmaceutically acceptable compositions which comprise the polymeric particles or the agent formulated together with one or more pharmaceutically acceptable carriers (additives) and/or diluents. The pharmaceutical composition can be specially formulated for administration in solid or liquid form, including those adapted for the following: (1) oral administration, for example, drenches (aqueous or non-aqueous solutions or suspensions), lozenges, dragees, capsules, pills, tablets (e.g., those targeted for buccal, sublingual, and systemic absorption), boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) transmucosally; or (9) nasally.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Carriers include compounds that facilitate the administration and delivery of another compound and can also facilitate the administration and delivery of another compound and can also facilitate the incorporation of another compound into cells or tissues. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alchols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. Dimethyl sulfoxide (DMSO) is a commonly used carrier for improving incorporation of certain organic compounds into cells or tissues.

Pharmaceutically-acceptable antioxidants include, but are not limited to, (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lectithin, propyl gallate, alpha-tocopherol, and the like; and (3) metal chelating agents, such as citric acid, ethylenediamine tetraacetic acid (EDTA), sorbitol, tartaric acid, phosphoric acids, and the like.

For administering to the subject, the polymeric particles and the agent can be formulated in separate pharmaceutically acceptable formulations or combined in one pharmaceutically acceptable formulation. In some embodiments, the polymeric particles and the agent are formulated in separate pharmaceutically acceptable formulations formulations.

As used herein, the term "pharmaceutical composition" means a chemical compound or composition capable of inducing, alone or in combination with another agent, a desired therapeutic effect or outcome in a subject and includes agents or compounds that can increase bioavailability of other agents. In some embodiments, a pharmaceutical composition contains an active agent, which is the agent that induces the desired therapeutic effect. The pharmaceutical composition can contain a prodrug of the compounds provided herein. In some embodiments, a pharmaceutical composition contains inactive ingredients, such as, for example, carriers and excipients.

In some embodiments, the method provided herein can be used to treat cancer. For example, the method provided herein can be used to treat various malignancies, e.g., lung, colon, prostate, pancreas, ovarian, sarcoma, mesothelioma, or breast cancer at all stages. In some embodiments, the invention provides a method of treating a tumor in a subject, the method comprising administering to the subject one or more of the polymer particles to a location or multiple locations of the malignancy, and administering to the subject an agent that is toxic to the tumor, such as a chemotherapeutic drug. Without limitations, the method described herein can be used to treat cancer. For example, the method provided herein can be used to treat lung, colon, prostate, pancreas, ovarian, or breast cancer or mesothelioma or sarcoma. The polymeric particles of the invention are also useful for bone marrow transplantation to target residual tumor cells in the graft (i.e. to target lymphomas and leukemias).

As used herein, the term "cancer" or "tumor" refers to the presence of cells possessing characteristics typical of cancer-causing cells, such as uncontrolled proliferation, immortality, metastatic potential, rapid growth and proliferation rate, and certain characteristic morphological features. This term refers to any type of malignancy (primary or metastases). The cancer can be an early stage cancer without local or systemic invasion or the cancer can be an invasive cancer and/or a cancer capable of metastasis. Typical cancers are solid or hematopoietic cancers such as breast, stomach, oesophageal, sarcoma, ovarian, endometrium, bladder, cervix uteri, rectum, colon, lung or oral cancers, paediatric tumours (neuroblastoma, glioblastoma multiforme), lymphoma, leukaemia, myeloma, seminoma, Hodgkin and malignant hemopathies. In some embodiments, the cancer is selected from the group consisting of leukemia, lymphoma, melanoma, lung cancer, bowel cancer, colon cancer, rectal cancer, colorectal cancer, brain cancer, liver cancer, pancreatic cancer, breast cancer, prostate cancer, testicular cancer and retinoblastoma. In some preferred embodiment, the cancer is a solid cancer, preferably a breast cancer or a prostate cancer, more preferably a breast cancer.

As used herein, the term "treatment of cancer" refers to any act intended to extend life span of patients such as therapy and retardation of the disease. The treatment can be designed to eradicate the tumor, to stop the progression of the tumor, to prevent the occurrence of metastasis, to promote the regression of the tumor and/or to prevent muscle invasion of cancer. Preferably, the term "treatment of cancer" as used herein, refers to the prevention or delay of metastasis formation, disease progression and/or systemic invasion.

In some embodiments, the method further comprises selecting a subject for treatment of cancer, i.e., a subject having or suspected of developing a cancer.

The tumor can be a malignant tumor or a benign tumor. The tumor can be a primary tumor or a metastatic tumor.

The drug or agent, such as a therapeutic agent, can be administered within the polymer particles, before administering the polymer particles, simultaneously with administering the polymer particles or after administering the polymer particles.

The treatment can be treatment of early, late or previously treated malignancy or it can include prevention or inhibition of recurrence of a malignancy that has been surgically removed or locally treated following radiofrequency ablation or radiosurgery/radiation therapy. The treatment can include avoidance of locoregional lymph node metastasis, augmentation of local wound healing and decrease in infection, manipulation of structure and abnormal scar formation to treat a chronic condition, and for the treatment of postoperative pain.

In some embodiments, the polymeric particle can be labeled, for example, with a fluorescent label to allow monitoring of the location of the polymeric particle. In some embodiments, the particle is unlabeled, and a labeled substance can be delivered as a subsequent agent to allow the label to concentrate into the tissue site, such as a tumor tissue site.

The polymeric particles can also be administered to sites where tumor regrowth is likely to occur. The particles can be administered to areas where, as a consequence of disease (COPD, inflammatory bowel disease etc) or systemic chemotherapy, poor healing can result in major complications. In addition, the particles can be administered to the margins of a surgical excision or resection, or to sites following local ablative therapy. For such applications, the polymeric particles can be prepared to adhere to the surgical margin or be retained within the confines and perimeter of the mass.

The particles can also be used to coat medical devices such as stents and artificial body parts.

In addition, other types of surgery can benefit from the use of the methods and polymeric particles described herein. For example, particles can be delivered and then used with antibiotics for local delivery at a surgical site. The local concentration of the antibiotics can be prolonged at the surgical site to reduce the risk of post-surgical infections and complications, such as *Clostridium difficile* infection. Thus provided herein is a method for local delivery of antibiotics, the method comprising administering to a subject in need of local antibiotic treatment one or more of empty polymeric particles prior to, simultaneously with, or subsequent to administering an antibiotic or a mixture of antibiotics. This method provides an alternative to the use and risk of systemic antibiotics.

The particles can contain and or be used with anesthetics, such as local amide anesthetics, IV narcotics, or anti-inflammatory agents (steroids, NSAIDS etc) to reduce the discomfort of patients, particularly surgical incisions or sites of injury or inflammation. The use of such polymeric materials can reduce morbidity secondary to delirium and constipation by decreasing systemic levels of narcotics, thus decreasing the length of hospital stay for patients, and reduce overall health care costs.

Without limitations, the method described herein can be used to deliver or concentrate any agent or agents. The agent can be in any pharmaceutically acceptable form, including pharmaceutically acceptable salts. A large number of pharmaceutical agents are known in the art and are amenable for use in the pharmaceutical compositions of the polymeric materials described herein. Acceptable agents are described elsewhere herein, and include, but are not limited to, chemotherapeutic agents, such as radiosensitizers, receptor inhibitors and agonists or other anti-neoplastic agent; small molecules, peptides, DNA/RNA nucleotides, immune modulators and bioactive agents, such as cytokines, growth factors or steroids with or without the co-incorporation of tumor or pathogen antigens to increase the anti-neoplastic response as a means of vaccine development; local anesthetic agents; or antibiotics.

Accordingly, as used herein, the term "agent" refers to any molecule, compound or composition that needs to be delivered, concentrated or localized at a desired site. Without limitations, the agent can be selected from the group consisting of small organic or inorganic molecules (i.e., including heteroorganic and organometallic compounds), saccharines, oligosaccharides, polysaccharides, biological macromolecules, peptides, proteins, peptide analogs and derivatives, peptidomimetics, antibodies, fragments or portions of antibodies, nucleic acids, nucleic acid analogs and derivatives, extracts made from biological materials (such as bacteria, plants, fungi, or animal cells), animal tissues, naturally occurring or synthetic compositions, and any combinations thereof.

Furthermore, the term "agent" includes without limitation, medicaments, vitamins, mineral supplements, hormones, growth factors, substances used for the treatment, prevention, diagnosis, cure or mitigation of disease or illness, substances that affect the structure or function of the body, or pro-drugs, which become biologically active or more active after they have been placed in a predetermined physiological environment.

As used herein, the terms "therapeutic agent" and "bioactive agent" refer to an agent that is capable of exerting a biological effect in vitro and/or in vivo. The biological effect can be therapeutic in nature. As used herein, "bioactive agent" refers also to a substance that is used in connection with an application that is diagnostic in nature, such as in methods for diagnosing the presence or absence of a disease in a patient. The bioactive agents can be neutral or positively or negatively charged. Examples of suitable bioactive agents include pharmaceuticals and drugs, cells, gases and gaseous precursors (e.g., $O_2$), synthetic organic molecules, proteins, enzymes, growth factors, vitamins, steroids, polyanions, nucleosides, nucleotides, polynucleotides and diagnostic agents, such as contrast agents for use in connection with magnetic resonance imaging, ultrasound, positron emission tomography (PET), X-ray computed tomography or other imaging modalities.

Exemplary agents include, but are not limited to, (1) nonsteroidal anti-inflammatory drugs (NSAIDs) analgesics, including but no limited to diclofenac, ibuprofen, ketoprofen, and naproxen; (2) opiate agonist analgesics, including but no limited to codeine, vancomycin, ceftazidime, fentanyl, hydromorphone, and morphine; (3) salicylate analgesics, including but no limited to aspirin (ASA) (or enteric coated ASA); (4) H1-blocker antihistamines, including but no limited toclemastine and terfenadine; (5) H2-blocker antihistamines, including but no limited tocimetidine, famotidine, nizadine, and ranitidine; (6) anti-infective agents, including but no limited tomupirocin; (7) antianaerobic anti-infectives, including but no limited tochloramphenicol metronidazole and clindamycin; (8) antifungal antibiotic anti-infectives, including but no limited toamphotericin b, clotrimazole, fluconazole, and ketoconazole; (9) macrolide antibiotic anti-infectives, including but no limited toazithromycin and erythromycin; (10) miscellaneous beta-lactam antibiotic anti-infectives, including but no limited toaztreonam and imipenem; (11) penicillin antibiotic anti-infectives, including but not limited to nafcillin, oxacillin, penicillin G, and penicillin V; (12) quinolone antibiotic anti-infectives, including but not limited to ciprofloxacin and norfloxacin; (13) tetracycline antibiotic anti-infectives, including but not limited to doxycycline, minocycline, and tetracycline; (14) antituberculosis antimycobacterial anti-infectives including but not limited to isoniazid (INH), and rifampin; (15) antiprotozoal anti-infectives, including but not limited to atovaquone and dapsone; (16) antimalarial antiprotozoal anti-infectives, including but not limited to chloroquine and pyrimethamine; (17) anti-retroviral anti-infectives, including but not limited to ritonavir and zidovudine; (18) antiviral anti-infective agents, including but not limited to acyclovir, ganciclovir, interferon alpha, and rimantadine; (19) alkylating antineoplastic agents, including but not limited to carboplatin and cisplatin; (20) nitrosourea alkylating antineoplastic agents, including but not limited to carmustine (BCNU); (21) antimetabolite antineoplastic agents, including but not limited to methotrexate; (22) pyrimidine analog antimetabolite antineoplastic agents, including but not limited to fluorouracil (5-FU), gemcitabine, or ceftazidine, aminoglycodi meroperium, or ticarcillin and tobramycin; (23) hormonal antineoplastics, including but not limited to goserelin, leuprolide, and tamoxifen; (24) natural antineoplastics, including but not limited to aldesleukin, interleukin-2, docetaxel, etoposide (VP-16), interferon alpha, paclitaxel, and tretinoin (ATRA); (25) antibiotic natural antineoplastics, including but not limited to bleomycin, actinomycin, daunorubicin, doxorubicin, and mitomycin; (26) vinca alkaloid natural antineoplastics, including but not limited to vinblastine and vincristine; (27) autonomic agents, including but not limited to nicotine; (28) anticholinergic autonomic agents, including but not limited to benztropine and trihexyphenidyl; (29) antimuscarinic anticholinergic autonomic agents, including but not limited to atropine and oxybutynin; (30) ergot alkaloid autonomic agents, including but not limited to bromocriptine; (31) cholinergic agonist parasympathomimetics, including but not limited to pilocarpine; (32) cholinesterase inhibitor parasympathomimetics, including but not limited to pyridostigmine; (33) alpha-blocker sympatholytics, including but not limited to prazosin; (34) beta-blocker sympatholytics, including but not limited to atenolol; (35) adrenergic agonist sympathomimetics, including but not limited to albuterol and dobutamine; (36) cardiovascular agents, including but not limited to aspirin (ASA), plavix (Clopidogrel bisulfate) etc; (37) beta-blocker antianginals, including but not limited to atenolol and propranolol; (38) calcium-channel blocker antianginals, including but not limited to nifedipine and verapamil; (39) nitrate antianginals, including but not limited to isosorbide dinitrate (ISDN); (40) cardiac glycoside antiarrhythmics, including but not limited to digoxin; (41) class I anti-arrhythmics, including but not limited to lidocaine, mexiletine, phenytoin, procainamide, and quinidine; (42) class II antiarrhythmics, including but not limited to atenolol, metoprolol, propranolol, and timolol; (43) class III antiarrhythmics, including but not limited to amiodarone; (44) class IV antiarrhythmics, including but not limited to diltiazem and verapamil; (45) alpha-blocker antihypertensives, including but not limited to prazosin; (46) angiotensin-converting enzyme inhibitor (ACE inhibitor) antihypertensives, including but not limited to captopril and enalapril; (47) beta blocker antihypertensives, including but not limited to atenolol, metoprolol, nadolol, and propanolol; (48) calcium-channel blocker antihypertensive agents, including but not limited to diltiazem and nifedipine; (49) central-acting adrenergic antihypertensives, including but not limited to clonidine and methyldopa; (50) diurectic antihypertensive agents, including but not limited to amiloride, furosemide, hydrochlorothiazide (HCTZ), and spironolactone; (51) peripheral vasodilator antihypertensives, including but not limited to hydralazine and minoxidil; (52) antilipemics, including but not limited to gemfibrozil and probucol; (53) bile acid sequestrant antilipemics, including but not limited to cholestyramine; (54) HMG-CoA reductase inhibitor antilipemics, including but not limited to lovastatin and pravastatin; (55) inotropes, including but not limited to amrinone, dobutamine, and dopamine; (56) cardiac glycoside inotropes, including but not limited to digoxin; (57) thrombolytic agents or enzymes, including but not limited to alteplase (TPA), anistreplase, streptokinase, and urokinase; (58) dermatological agents, including but not limited to colchicine, isotretinoin, methotrexate, minoxidil, tretinoin (ATRA); (59) dermatological corticosteroid anti-inflammatory agents, including but not limited to betamethasone and dexamethasone; (60) antifungal topical antiinfectives, including but not limited to amphotericin B, clotrimazole, miconazole, and nystatin; (61) antiviral topical anti-infectives, including but not limited to acyclovir; (62) topical antineoplastics, including but not limited to fluorouracil (5-FU); (63) electrolytic and renal agents, including but not limited to lactulose; (64) loop diuretics, including but not limited to furosemide; (65) potassium-sparing diuretics, including but not limited to triamterene; (66) thiazide diuretics, including but not limited to hydrochlorothiazide (HCTZ); (67) uricosuric agents, including but not limited to probenecid; (68) enzymes including but not limited to RNase and DNase; (69) immunosupressive agents, including but not limited to cyclosporine, steroids, methotrexate, tacrolimus, sirolimus, rapamycin; (70) antiemetics, including but not limited to prochlorperazine; (71) salicylate gastrointestinal anti-inflammatory agents, including but not limited to sulfasalazine; (72) gastric acid-pump inhibitor anti-ulcer agents, including but not limited to omeprazole; (73) $H_2$-blocker anti-ulcer agents, including but not limited to cimetidine, famotidine, nizatidine, and ranitidine; (74) digestants, including but not limited to pancrelipase; (75) prokinetic agents, including but not limited to erythromycin; (76) opiate agonist intravenous anesthetics including but not limited to fentanyl; (77) hematopoietic antianemia agents, including but not limited to erythropoietin, filgrastim (G-CSF), and sargramostim (GM-CSF); (78) coagulation agents, including but not limited to antihemophilic factors 1-10 (AHF 1-10); (79) anticoagulants, including but not limited to warfarin, heparin (important for heparin bound polymers and cardiopulmonary bypass pump circuits), argatroban—each works by a different mechanism and is metabolized differently; (80) growth receptor inhibitors, including but not limited to erlotinib and gefetinib; (82) abortifacients, including but not limited to methotrexate; (83) antidiabetic agents, including but not limited to insulin; (84) oral contraceptives, including but not limited to estrogen and progestin; (85) progestin contraceptives, including but not limited to levonorgestrel and norgestrel; (86) estrogens including but not limited to conjugated estrogens, diethylstilbestrol (DES), estrogen (estradiol, estrone, and estropipate); (87) fertility agents, including but not limited to clomiphene, human chorionic gonadatropin (HCG), and menotropins; (88) parathyroid agents including but not limited to calcitonin; (89) pituitary hormones, including but not limited to desmopressin, goserelin, oxytocin, and vasopressin (ADH); (90) progestins, including but not limited to medroxyprogesterone, norethindrone, and progesterone; (91) thyroid hormones, including but not limited to levothyroxine; (92) immunobiologic agents, including but not limited to interferon beta-1b and interferon gamma-1b; (93) immunoglobulins, including but not limited to immune globulin IM, IMIG, IGIM and immune globulin IV, IVIG, IGIV; (94) amide local anesthetics, including but not limited to lidocaine; (95) ester local anesthetics, including but not limited to benzocaine and procaine; (96) musculoskeletal corticosteroid anti-inflammatory agents, including but not limited to beclomethasone, betamethasone, cortisone, dexamethasone, hydrocortisone, and prednisone; (97) musculoskeletal anti-inflammatory immunosuppressives, including but not limited to azathioprine, cyclophosphamide, and methotrexate; (98) musculoskeletal nonsteroidal anti-inflammatory drugs (NSAIDs), including but not limited to diclofenac, ibuprofen, ketoprofen, ketorlac, and naproxen; (99) skeletal muscle relaxants, including but not limited to baclofen, cyclobenzaprine, and diazepam; (100) reverse neuromuscular blocker skeletal muscle relaxants, including but not limited to pyridostigmine; (101) neurological agents, including but not limited to nimodipine, riluzole, tacrine and ticlopidine; (102) anticonvulsants, including but not limited to carbamazepine, gabapentin, lamotrigine, phenytoin, and valproic acid; (103) barbiturate anticonvulsants, including but not limited to phenobarbital and primidone; (104) benzodiazepine anticonvulsants, including but not limited to clonazepam, diazepam, and lorazepam; (105) anti-parkisonian agents, including but not limited to bromocriptine, levodopa, carbidopa, and pergolide; (106) anti-vertigo agents, including but not limited to meclizine; (107) opiate agonists, including but not limited to codeine, fentanyl, hydromorphone, methadone, and morphine; (108) opiate antagonists, including but not limited to naloxone; (109) beta-blocker anti-glaucoma agents, including but not limited to timolol; (110) miotic anti-glaucoma agents, including but not limited to pilocarpine; (111) ophthalmic aminoglycoside antiinfectives, including but not limited to gentamicin, neomycin, and tobramycin; (112) ophthalmic quinolone antiinfectives, including but not limited to ciprofloxacin, norfloxacin, and ofloxacin; (113) ophthalmic corticosteroid anti-inflammatory agents, including but not limited to dexamethasone and prednisolone; (114) ophthalmic nonsteroidal anti-inflammatory drugs (NSAIDs), including but not limited to diclofenac; (115) antipsychotics, including but not limited to clozapine, haloperidol, and risperidone; (116) benzodiazepine anxiolytics, sedatives and hypnotics, including but not limited to clonazepam, diazepam, lorazepam, oxazepam, and prazepam; (117) psychostimulants, including but not limited to methylphenidate and pemoline; (118) antitussives, including but not limited to codeine; (119) bronchodilators, including but not limited to theophylline; (120) adrenergic agonist bronchodilators, including but not limited to albuterol; (121) respiratory corticosteroid anti-inflammatory agents, including but not limited to dexamethasone; (122) antidotes, including but not limited to flumazenil and naloxone; (123) heavy metal antagonists/chelating agents, including but not limited to penicillamine; (124) deterrent substance abuse agents, including but not limited to disulfiram, naltrexone, and nicotine; (125) withdrawal substance abuse agents, including but not limited to bromocriptine; (126) minerals, including but not limited to iron, calcium, and magnesium; (127) vitamin B compounds, including but not limited to cyanocobalamin (vitamin B12) and niacin (vitamin B3); (128) vitamin C compounds, including but not limited to ascorbic acid; (129) vitamin D compounds, including but not limited to calcitriol; (130) antiparasitic compounds including but not limited to metronidazole; (131) bronchodilators, including but not limited to salmeterol, and beta agonists; (132) leukotriene blockers/modifiers including montelukast or zileuton; (133) inhaled steroids including but not limited to fluticasone, beclomethasone, or budesonide. Anti-bleeding (hemostatic) agents including but not limited to protamine and antihelminth, radiation sensitizers, and other drugs including but not limited to racin and cyclosporine are also included. Additional anticancer drugs including but not limited to pycnidione as well as anti-Myc inhibitors.

In addition to the foregoing, the following less common drugs can also be used as encapsulated within the particles of the invention or in combination with the particles of the invention for targeted delivery of the drugs: chlorhexidine; estradiol cypionate in oil; estradiol valerate in oil; flurbiprofen; flurbiprofen sodium; ivermectin; levodopa; nafarelin; and somatropin. Further, the following drugs can also be used: pycnidione, cyclosporine, recombinant beta-glucan; bovine immunoglobulin concentrate; bovine superoxide dismutase; the formulation comprising fluorouracil, epinephrine, and bovine collagen; recombinant hirudin (r-Hir), HIV-1 immunogen; human anti-TAC antibody; recombinant human growth hormone (r-hGH); recombinant human hemoglobin (r-Hb); recombinant human mecasermin (r-IGF-1); recombinant interferon beta-1a; lenograstim (G-CSF); olanzapine; recombinant thyroid stimulating hormone (r-TSH); and topotecan. Further still, the following intravenous products can be used: acyclovir sodium; aldesleukin; atenolol; bleomycin sulfate, human calcitonin; salmon calcitonin; carboplatin; carmustine; dactinomycin, daunorubicin HCl; docetaxel; doxorubicin HCl; epoetin alfa; etoposide (VP-16); fluorouracil (5-FU); ganciclovir sodium; gentamicin sulfate; interferon alpha; leuprolide acetate; meperidine HCl; methadone HCl; methotrexate sodium; paclitaxel; ranitidine HCl; vinblastin sulfate; and zidovudine (AZT).

Some specific examples of useful pharmaceutical agents from the above categories include: (a) anti-neoplastics including but not limited to androgen inhibitors, antimetabolites, cytotoxic agents, receptor inhibitors, and immunomodulators; (b) anti-tussives including but not limited to dextromethorphan, dextromethorphan hydrobromide, noscapine, carbetapentane citrate, and chlorphedianol hydrochloride; (c) antihistamines including but not limited to chlorpheniramine maleate, phenindamine tartrate, pyrilamine maleate, doxylamine succinate, and phenyltoloxamine citrate; (d) decongestants including but not limited to phenylephrine hydrochloride, phenylpropanolamine hydrochloride, pseudoephedrine hydrochloride, and ephedrine; (e) various alkaloids including but not limited to codeine phosphate, codeine sulfate and morphine; (f) mineral supplements including but not limited to potassium chloride, zinc chloride, calcium carbonates, magnesium oxide, and other alkali metal and alkaline earth metal salts; (g) ion exchange resins including but not limited to cholestryramine; (h) anti-arrhythmics including but not limited to N-acetylprocainamide; (i) antipyretics and analgesics including but not limited to acetaminophen, aspirin and ibuprofen; (j) appetite suppressants including but not limited to phenyl-propanolamine hydrochloride or caffeine; (k) expectorants including but not limited to guaifenesin; (l) antacids including but not limited to aluminum hydroxide and magnesium hydroxide; (m) biologicals including but not limited to peptides, polypeptides, proteins and amino acids, hormones, interferons or cytokines, and other bioactive peptidic compounds, including but not limited to interleukins 1-18 including mutants and analogues, RNase, DNase, luteinizing hormone releasing hormone (LHRH) and analogues, gonadotropin releasing hormone (GnRH), transforming growth factor-.beta. (TGF-beta), fibroblast growth factor (FGF), tumor necrosis factor-alpha & beta (TNF-alpha & beta), nerve growth factor (NGF), growth hormone releasing factor (GHRF), epidermal growth factor (EGF), fibroblast growth factor homologous factor (FGFHF), hepatocyte growth factor (HGF), insulin growth factor (IGF), invasion inhibiting factor-2 (IIF-2), bone morphogenetic proteins 1-7 (BMP 1-7), somatostatin, thymosin-alpha-1, gamma-globulin, superoxide dismutase (SOD), complement factors, hGH, tPA, calcitonin, ANF, EPO and insulin; and (n) anti-infective agents including but not limited to antifungals, anti-virals, antihelminths, antiseptics and antibiotics. Additional agents include hemoglobin, oxygen, nitric oxide, silver or other nobel metals. Additional agents include drugs that have renal toxicity and cardio toxicity, wherein the delivery with the particles assists in reducing the renal or cardiotoxicity by delivering the drugs in a targeted manner to a tissue site other than kidneys or the heart.

Examples of specific drugs that can be used include, but are not limited to asparaginase; bleomycin; busulfan; capecitabine; carboplatin; carmustine; chlorambucil; cisplatin; cyclophosphamide; cytarabine; dacarbizine; dactinomycin; daunorubicin; dexrazoxane; docetaxel; doxorubicin; erlotinibil/gefetinib; etoposide; floxuridine; fludarabine; fluoruracil; gemcitabine; 10-hydrocamptothecin; hydroxyurea; idarubicin; ifosfamide; irinotecan; lomustine; mechlorethamine; melphalan; mercaptopurine; methotrexate; mitomycin; mitotane; mitoxantrone; paclitaxel; pentostatin; plicamycin; pemextred procarbazine; rituximabe; streptozocin; teniposid; thioguanine; thiotepa; vinplastine; vinchristine; and vinorelbineor derivates of these molecules.

Examples of anticancer, antineoplastic agents include, but are not limited to, camptothecins. These drugs are antineoplastic by virtue of their ability to inhibit topoisomerase I. Camptothecin is a plant alkaloid isolated from trees indigenous to China and analogs thereof including but not limited to 9-aminocamptothecin, 9-nitrocamptothecin, 10-hydroxycamptothecin, 10,11-methylenedioxycamptothecin, 9-nitro 10,11,methylenehydroxycamptothecin, 9-chloro-10, 11-methylenehydroxycamptothecin, 9-amino-10,11-methylenehydroxycamptothecin, 7-ethyl-10-hydroxycamptothecin (SN-38), topotecan, DX-8951, Lurtotecan (GII147221C), and other analogs (collectively referred to herein as camptothecin drugs) are presently under study worldwide in research laboratories for treatment of colon, breast, and other cancers.

Additionally, the pharmaceutical agent can be a radiosensitizer, including but not limited to metoclopramide, sensamide or neusensamide (manufactured by Oxigene); profiromycin (made by Vion); RSR13 (made by Allos); THYMITAQ® (made by Agouron), etanidazole or lobenguane (manufactured by Nycomed); gadolinium texaphrin (made by Pharmacyclics); BuDR/Broxine (made by NeoPharm); IPdR (made by Sparta); CR2412 (made by Cell Therapeutic); L1X (made by *Terrapin*); agents that minimize hypoxia, and the like. The biologically active substance can be selected from the group consisting of peptides, poly-peptides, proteins, amino acids, polysaccharides, growth factors, hormones, anti-angiogenesis factors, interferons or cytokines, elements, and pro-drugs. In a particularly preferred embodiment, the biologically active substance is a therapeutic drug or pro-drug, most preferably a drug selected from the group consisting of chemotherapeutic agents and other antineoplastics including but not limited to paclitaxel, antibiotics, anti-virals, antifungals, anesthetics, antihelminths, anti-inflammatories, and anticoagulants.

In some embodiments, the agent is a biologically active substance that is a therapeutic drug or pro-drug, most preferably a drug selected from the group consisting of chemotherapeutic agents and other antineoplastics including but not limited to paclitaxel, carboplatin and cisplatin; nitrosourea alkylating antineoplastic agents, including but not limited to carmustine (BCNU); fluorouracil (5-FU) and gemcitabine; hormonal antineoplastics, including but not limited to goserelin, leuprolide, and tamoxifen; receptor inhibitors including but not limited to erlotinib, gefetinib, Sunitinib, Imatinib, or anti-ckit inhibitors (registered name is Gleevec); natural antineoplastics, including but not limited to aldesleukin, interleukin-2, docetaxel, etoposide (VP-16), interferon alpha, paclitaxel, and tretinoin (ATRA). Furthermore, the agent to be delivered can be dissolved in an aqueous solution or in an aqueous solution containing another compound to increase the agent's solubility including but not limited to cremaphor E/L for paclitaxel.

Additional biologically active agents include, without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment. Useful active agents amenable for use in the new compositions include growth factors, including but not limited to transforming growth factors (TGFs), fibroblast growth factors (FGFs), platelet derived growth factors (PDGFs), epidermal growth factors (EGFs), connective tissue activated peptides (CTAPs), osteogenic factors, and biologically active analogs, fragments, and derivatives of such growth factors. Members of the transforming growth factor (TGF) supergene family, which are multifunctional regulatory proteins, are preferred. Members of the TGF supergene family include the beta-transforming growth factors (for example, TGF-b1, TGF-b2, and TGF-b3); bone morphogenetic proteins (for example, BMP-1, BMP-2, BMP-3, BMP-4, BMP-5, BMP-6, BMP-7, BMP-8, and BMP-9); heparin-binding growth factors (for example, fibroblast growth factor (FGF), epidermal growth factor (EGF), platelet-derived growth factor (PDGF), and insulin-like growth factor (IGF)); inhibins (for example, Inhibin A, Inhibin B); growth differentiating factors (for example, GDF-1); and activins (for example, Activin A, Activin B, and Activin AB).

Non-limiting examples of broad categories of useful pharmaceutical agents include the following therapeutic categories: anabolic agents, anesthetic agents, antacids, anti-asthmatic agents, anticholesterolemic and anti-lipid agents, anti-coagulants, anti-convulsants, anti-diarrheals, antiemetics, anti-infective agents, anti-inflammatory agents, anti-manic agents, anti-nauseants, antineoplastic agents, anti-obesity agents, anti-pyretic and analgesic agents, anti-spasmodic agents, anti-thrombotic agents, anti-uricemic agents, anti-anginal agents, antihistamines, anti-tussives, appetite suppressants, biologicals, cerebral dilators, coronary dilators, decongestants, diuretics, diagnostic agents, erythropoietic agents, expectorants, gastrointestinal sedatives, hyperglycemic agents, hypnotics, hypoglycemic agents, ion exchange resins, laxatives, mineral supplements, mucolytic agents, neuromuscular drugs, peripheral vasodilators, psychotropics, sedatives, small molecule inhibitors, receptor enzymes, stimulants, thyroid and anti-thyroid agents, uterine relaxants, vitamins, and prodrugs.

More specifically, non-limiting examples of useful pharmaceutical agents include the following categories: analgesics, including but not limited to nonsteroidal anti-inflammatory drugs, opiate agonists and salicylates; antihistamines, including but not limited to H1-blockers and H2-blockers; anti-infective agents, including but not limited to anthelmintics, antianaerobics, antibiotics, aminoglycoside antibiotics, antifungal antibiotics, cephalosporin antibiotics, macrolide antibiotics, miscellaneous beta-lactam antibiotics, penicillin antibiotics, quinolone antibiotics, sulfonamide antibiotics, tetracycline antibiotics, antimycobacterials, antituberculosis antimycobacterials, antiprotozoals, antimalarial antiprotozoals, antiviral agents, anti-retroviral agents, scabicides, and urinary anti-infectives; antineoplastic agents, including but not limited to alkylating agents, nitrogen mustard aklylating agents, nitrosourea alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; autonomic agents, including but not limited to anticholinergics, antimuscarinic anticholinergics, ergot alkaloids, parasympathomimetics, cholinergic agonist parasympathomimetics, cholinesterase inhibitor parasympathomimetics, sympatholytics, alphablocker sympatholytics, beta-blocker sympatholytics, sympathomimetics, and adrenergic agonist sympathomimetics; cardiovascular agents, including but not limited to antianginals, betablocker antianginals, calcium-channel blocker antianginals, nitrate antianginals, antiarrhythmics, cardiac glycoside antiarrhythmics, class I antiarrhythmics, class II antiarrhythmics, class III antiarrhythmics, class IV antiarrhythmics, antihypertensive agents, alpha-blocker antihypertensives, angiotensin-converting enzyme inhibitor (ACE inhibitor) antihypertensives, beta-blocker antihypertensives, calcium-channel blocker antihypertensives, central-acting adrenergic antihypertensives, diuretic antihypertensive agents, peripheral vasodilator antihypertensives, antilipemics, bile acid sequestrant antilipemics, HMG-CoA reductase inhibitor antilipemics, inotropes, cardiac glycoside inotropes, and thrombolytic agents; dermatological agents, including but not limited to antihistamines, anti-inflammatory agents, corticosteroid anti-inflammatory agents, antipruritics/local anesthetics, topical anti-infectives, antifungal topical anti-infectives, antiviral topical anti-infectives, and topical antineoplastics; electrolytic and renal agents, including but not limited to acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, including but not limited to pancreatic enzymes and thrombolytic enzymes; gastrointestinal agents, including but not limited to antidiarrheals, antiemetics, gastrointestinal anti-inflammatory agents, salicylate gastrointestinal anti-inflammatory agents, antacid anti-ulcer agents, gastric acid-pump inhibitor anti-ulcer agents, gastric mucosal anti-ulcer agents, H2—blocker anti-ulcer agents, cholelitholytic agents, digestants, emetics, laxatives and stool softeners, and prokinetic agents; general anesthetics, including but not limited to inhalation anesthetics, halogenated inhalation anesthetics, intravenous anesthetics, barbiturate intravenous anesthetics, benzodiazepine intravenous anesthetics, and opiate agonist intravenous anesthetics; hematological agents, including but not limited to antianemia agents, hematopoietic antianemia agents, coagulation agents, anticoagulants, hemostatic coagulation agents, platelet inhibitor coagulation agents, thrombolytic enzyme coagulation agents, and plasma volume expanders; hormones and hormone modifiers, including but not limited to abortifacients, adrenal agents, corticosteroid adrenal agents, androgens, antiandrogens, antidiabetic agents, sulfonylurea antidiabetic agents, antihypoglycemic agents, oral contraceptives, progestin contraceptives, estrogens, fertility agents, oxytocics, parathyroid agents, pituitary hormones, progestins, antithyroid agents, thyroid hormones, and tocolytics; immunobiologic agents, including but not limited to immunoglobulins, immunosuppressives, toxoids, and vaccines; local anesthetics, including but not limited to amide local anesthetics and ester local anesthetics; musculoskeletal agents, including but not limited to anti-gout anti-inflammatory agents, corticosteroid anti-inflammatory agents, gold compound anti-inflammatory agents, immuno-suppressive anti-inflammatory agents, nonsteroidal anti-inflammatory drugs (NSAIDs), salicylate anti-inflammatory agents, skeletal muscle relaxants, neuromuscular blocker skeletal muscle relaxants, and reverse neuromuscular blocker skeletal muscle relaxants; neurological agents, including but not limited to anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, including but not limited to antiglaucoma agents, beta-blocker anti-gluacoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic anti-inflammatory agents, ophthalmic corticosteroid anti-inflammatory agents, and ophthalmic nonsteroidal anti-inflammatory drugs (NSAIDs); psychotropic agents, including but not limited to antidepressants, heterocyclic antidepressants, monoamine oxidase inhibitors (MAOIs), sclerosants including but not limited to talc, alcohol or doxycyclin, selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, including but not limited to antitussives, bronchodilators, adrenergic agonist bronchodilators, antimuscarinic bronchodilators, expectorants, mucolytic agents, respiratory anti-inflammatory agents, leukotriene modifiers and respiratory corticosteroid anti-inflammatory agents; toxicology agents, including but not limited to antidotes, heavy metal antagonists/chelating agents, substance abuse agents, deterrent substance abuse agents, and withdrawal substance abuse agents; minerals; and vitamins, including but not limited to vitamin A, vitamin B, vitamin C, vitamin D, vitamin E, and vitamin K.

Additional, exemplary therapeutic agents include, but are not limited to, those found in *Harrison's Principles of Internal Medicine,* 13th Edition, Eds. T. R. Harrison et al. McGraw-Hill N.Y., NY; Physicians' Desk Reference, 50th Edition, 1997, Oradell N.J., Medical Economics Co.; Pharmacological Basis of Therapeutics, 8th Edition, Goodman and Gilman, 1990; United States Pharmacopeia, The National Formulary, USP XII NF XVII, 1990, the complete contents of all of which are incorporated herein by reference.

The method described herein can also be used to deliver a pro-drug and a reagent for converting the pro-drug to an active form. This can be accomplished by encapsulating either the pro-drug or the reagent in the particles. The particles then can be delivered to the required site prior to, simultaneously with, or subsequent delivery of the other (pro-drug or the reagent). This can be useful in instances wherein the active font) of the drug has unwanted side effects when given systemically. Localizing the conversion of the pro-drug into active form at a desired site can reduce one or more of any unwanted side effects.

The method described herein can also be used for multi-drug therapy. For example, the method can be used to deliver two or more different drugs. This can be useful when the different drugs cannot be formulated in one formulation or the drugs needs to be administered at different periods of time but need interactions with each other for efficacy. Accordingly, in some embodiments, a first agent can be included in the polymeric particles that can be delivered to the desired site prior to, simultaneously with or after providing a second agent to the site. Thus, when two or more different agents are to be delivered, the term "empty particle" refers to particles that lack at least one of the agents to be delivered, concentrated or localized to the site In some embodiments, when two or more agents are to be delivered, they can all be selected independently from the group consisting of asparaginase; bleomycin; busulfan; capecitabine; carboplatin; carmustine chlorambucil; cisplatin; cyclophosphamide; cytarabine; dacarbazine; dactinomycin; daunorubicin; dexrazoxane; docetaxel; doxorubicin; etoposide; floxuridine; fludarabine; fluorouracil; gemcitabine; hydroxyurea; idarubicin; ifosfamide; irinotecan; lomustine; mechlorethamine; melphalan; mercaptopurine; methotrexate; mitomycin; mitotane; mitoxantrone; paclitaxel; pemetrexed; pentostatin; plicamycin; procarbazine; rituximab; streptozocin; teniposide; thioguanine; thiotepa; vinblastine; vincristine; vinorelbine; 10-hydrocamptothecin, and derivatives thereof. For example, one or more agents selected from the above group can be preloaded into the particles while one or more other agents selected from the above group can be delivered to the site prior to, simultaneously or after delivering the preloaded particles to the site.

In some embodiments, the polymeric particle is a particle described in or comprises an oligomer or polymer described in U.S. Pat. No. 7,671,095 and U.S. patent application Ser. No. 12/690,607, filed Jan. 20, 2010 and Ser. No. 12/818,693, filed Jun. 18, 2010, contents of all of which are incorporated herein by reference in their entireties.

In some embodiments, the polymeric particles can be prepared from a polymer comprising an acryl monomer of Formula I, II, or III:

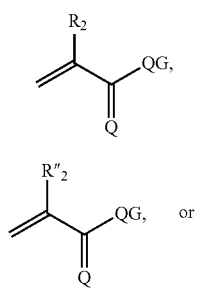

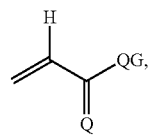

wherein:
each Q is independently selected from among O, S, Se, or NH;
G, or G and Q together, are selected independently from

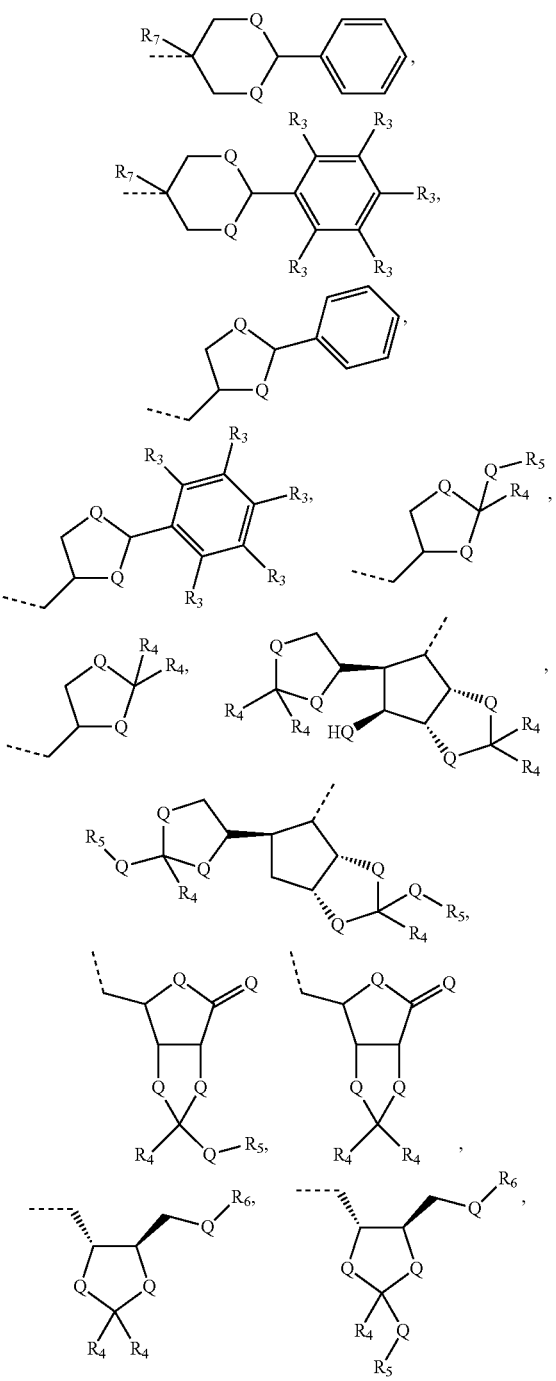

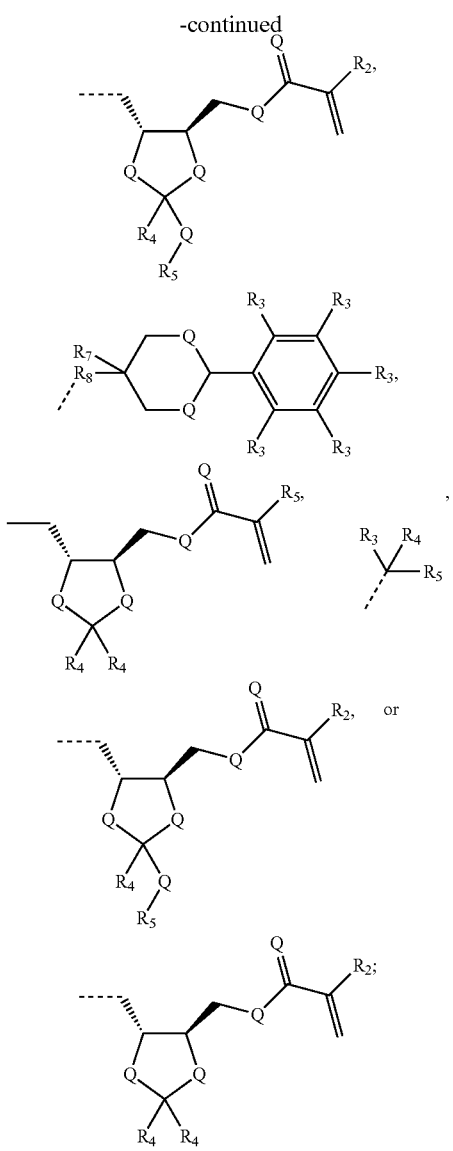

$R_2$ is selected from the group consisting of hydrogen, a straight or branched alkyl, cycloalkyl, aryl, olefin, silyl, alkylsilyl, arylsilyl, alkylaryl or arylalkyl chain of 1-50 carbons, wherein the alkyl, cycloalkyl, aryl, olefin, silyl, alkylsilyl, arylsilyl, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

$R''_2$ is selected from the group consisting of a straight or branched alkyl, cycloalkyl, aryl, olefin, silyl, alkylsilyl, arylsilyl, alkylaryl, or arylalkyl chain of 1-50 carbons, wherein the alkyl, cycloalkyl, aryl, olefin, silyl, alkylsilyl, arylsilyl, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

$R_3$ is selected from the group consisting of hydrogen, methoxy, ethoxy, amino, nitro, a straight or branched alkyl, cycloalkyl, aryl, olefin, silyl, alkylsilyl, arylsilyl, alkylaryl, or arylalkyl chain of 1-10 carbons;

$R_4$ and $R_5$ are each independently selected from the group consisting of a straight or branched alkyl, cycloalkyl, aryl, olefin, silyl, alkylsilyl, arylsilyl, alkylaryl or arylalkyl chain of 1-10 carbons;

$R_6$ is selected from the group consisting of a straight or branched alkyl, cycloalkyl, aryl, olefin, silyl, alkylsilyl, arylsilyl, alkylaryl or arylalkyl chain of 1-10 carbons;

$R_7$ is selected from the group consisting of hydrogen, a straight or branched alkyl, cycloalkyl, aryl, olefin, alkylaryl or arylalkyl chain of 1-50 carbons, wherein the alkyl, cycloalkyl, aryl, olefin, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate or halogen substituents; and $R_8$ is selected from the group consisting of hydrogen, a straight or branched alkyl, cycloalkyl, aryl, olefin, alkylaryl or arylalkyl chain of 1-50 carbons, wherein the alkyl, cycloalkyl, aryl, olefin, alkylaryl or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

Inventors have discovered that polymers comprising one or more of the above acryl monomers have the capacity to concentrate on a site of a tissue, such as tissue affected with abnormal growth or inflammation.

In some embodiments, a compound of Formula II is selected from the group consisting of a compound Formula IV, V, VI, or VII:

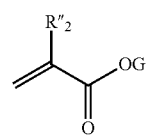

IV

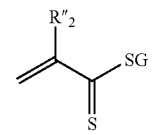

V

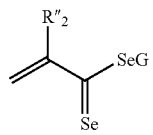

VI

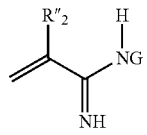

VII wherein $R''_2$ and G are selected independently from substituents as defined for compounds of Formula I, II, and III above.

In some embodiments, the compound of Formula II is a compound of Formula IV, where Q is oxygen. In some embodiments, the compound of Formula II is a compound of Formula V, where Q is sulfur. In some embodiments, the compound of Formula II is a compound of Formula VI, where Q is Se. In some embodiments, the compound of Formula II is a compound of Formula VII, where Q is NH.

In some embodiments, a compound of Formula III is selected from the group consisting of a compound Formula VIII, IX, X, or XI:

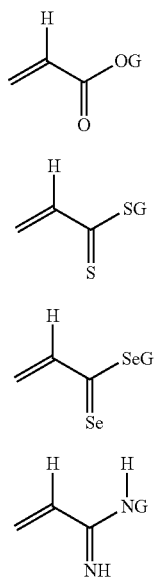

wherein R″$_2$ and G are selected independently from substituents as defined for compounds of Formula I, II, and III above.

In some embodiments, the compound of Formula III is a compound of Formula VIII where Q is oxygen. In some embodiments, the compound of Formula III is a compound of Formula IX, where Q is sulfur. In some embodiments, the compound of Formula III is a compound of Formula X, where Q is Se. In some embodiments, the compound of Formula III is a compound of Formula XI, where Q is NH.

In some embodiments, a compound of Formula II is selected from the group consisting of a compound Formula XII, XIII or XIV:

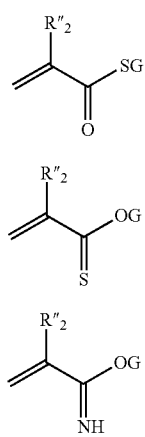

wherein R″$_2$ and G are selected independently from substituents as defined for compounds of Formula I, II, and III above.

In some embodiments, the compound of Formula II is a compound of Formula XII. In some embodiments, the compound of Formula II is a compound of Formula XIII. In some embodiments, the compound of Formula II is a compound of Formula XIV.

In some embodiments, a compound of Formula III is independently selected from the group consisting of a compound of Formula XV, XVI, or XVII:

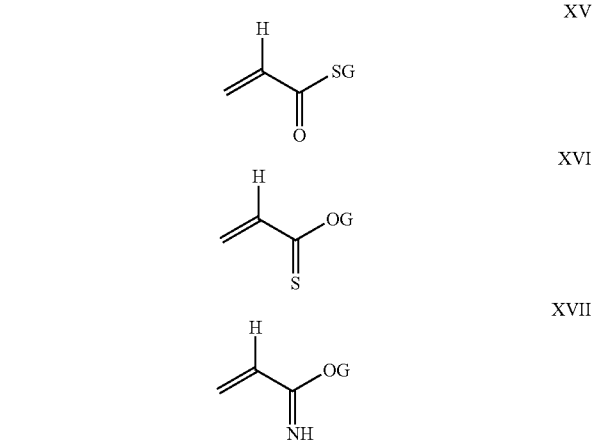

wherein R″$_2$ and G are selected independently from substituents as defined for compounds of Formula I, II, and III above.

In some embodiments, each G group of any of Formula II-XVI is independently selected from a substituent listed for group G in Formula I, II, and III above.

In some embodiments, R$_2$ of Formula I is selected from the group consisting of, hydrogen, C$_1$-C$_{20}$ alkyl, cycloalkyl, C$_1$-C$_{20}$ haloalkyl, heteroalkyl, cycloalkyl, alkylcycloalkyl, aryl and heteroaryl, wherein the alkyl, haloalkyl, heteroalkyl, cycloalkyl, alkylcycloalkyl, aryl and heteroaryl can be optionally substituted. In some embodiments, R$_2$ of Formula I is selected from the group consisting of C$_1$-C$_{20}$ alkyl, cycloalkyl, aryl and heteroaryl. In some embodiments, R$_2$ of Formula I is selected from the group consisting of C$_1$-C$_{20}$ alkyl. In some aspects of this embodiment, the alkyl is optionally substituted with halo, OH, NH$_2$, NH(CH$_3$), N(CH$_3$)$_2$, or COOH.

In some embodiments, the R$_2$ of Formula I is selected from H, methyl, ethy, isopropyl,

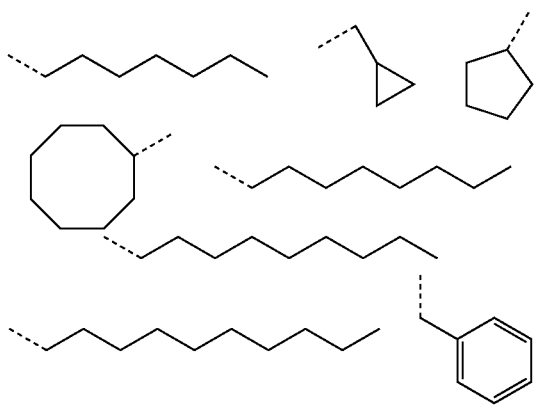

-continued

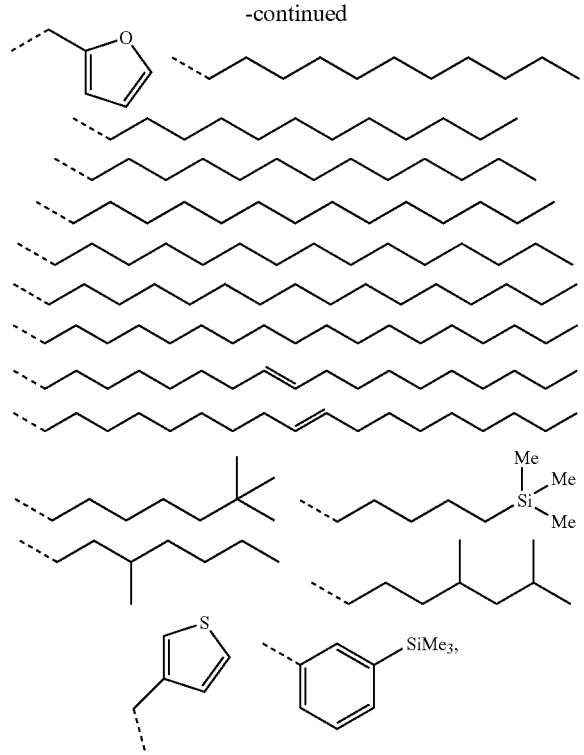

or any combinations thereof.

In some embodiments, the R$_2$ of Formula I is selected from the following:

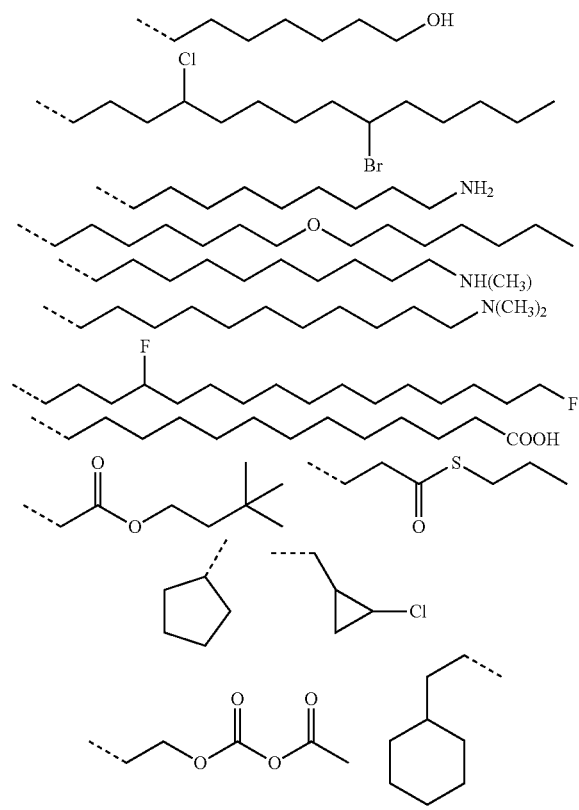

-continued

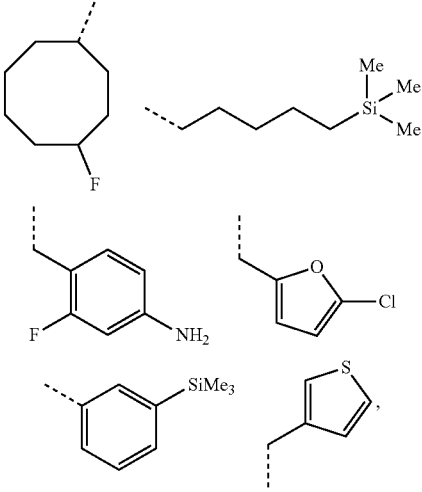

or any combinations thereof.

The acryl monomer units described herein can be synthesized by reacting a compound of Formula I' to provide a compound of Formula I as shown in Scheme I:

Scheme I

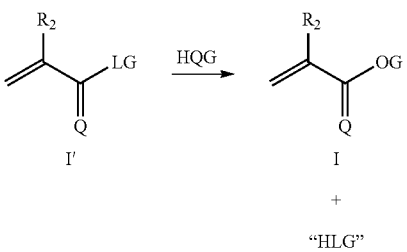

wherein each Q, G, and R$_2$ are independently selected or G and Q together are selected from substituents as defined for compounds of Formula I, II, and III above; and LG is a leaving group such as Cl or Br.

In one embodiment, a compound of Formula HQG, where Q and G are as defined herein, is dissolved in a solvent such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), dimethyl sulfoxide, acetic acid, n-butanol, isopropanol, n-propanol, ethanol, methanol or water. In some embodiments, a compound of Formula HQG is dissolved in THF. To this solution is added an acryloyl halide, such as methacryloyl chloride. In some embodiments a base, such as a trialkyl amine, e.g., triethylamine, is added to the reaction mixture. The resulting product is a compound of Formula I.

In another embodiment, a compound of Formula I is prepared by reacting a compound of Formula HQG, where Q and G are defined as above, with an acryl anhydride, such as methacrylic anhydride, in the presence of a base, such as triethyl amine.

A compound of Formula I, II, or III can be polymerized to yield a compound of Formula XX as shown in Scheme II.

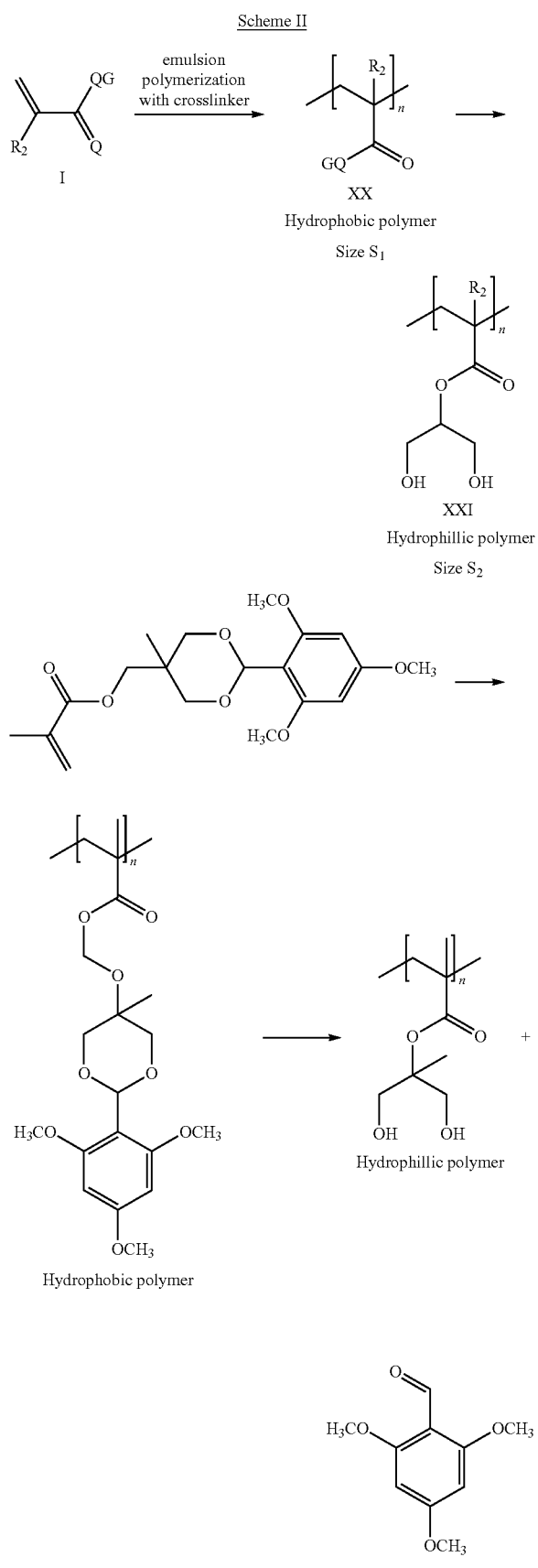

Scheme II wherein each Q, G, and $R_2$ are independently selected or G and Q together are selected from substituents as defined for compounds of Formula I, II, and III above;

n is an integer from 1-500; and each polymeric terminal group is selected from among amines, thiols, amides, phosphates, sulphates, hydroxides, alkenes and alkynes.

In Scheme II, $S_1$ and $S_2$ refer to the size of particles, measured as the diameter of the particle, of the associated composition.

Any method of acryl polymerization known in the art can be used for this reaction. For example, a compound of Formula I can be reacted with a free-radical initiator. Free-radical initiators include halogen molecules, such as $Cl_2$, azo compounds, such as 2,2'-azobis(2-methylpropionitrile) (AIBN), ammonium peroxodisulfate (APS) and tetramethylethylenediamine (TEMED), and organic peroxides, such as di-t-butylperoxide. Alternatively, the polymerization can be induced by light and a photoinitiator.

In one embodiment, a compound of Formula I is dissolved in a solvent, such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), or dimethyl sulfoxide, and reacted with AIBN to yield a compound of Formula XX.

In some embodiments, the polymer of Formula XX is hydrophobic and contains a pH sensitive group. G groups that are pH sensitive can be selected from the group consisting of substituents for Gas set forth in compounds of Formula I, II and III above.

As shown in Scheme II, Polymers of Formula XXI can be obtained by acid catalyzed hydrolysis from polymers of Formula XX, which contain a pH sensitive group. Any method of acid catalyzed hydrolysis known in the art can be used for this transformation. For example, the hydrolysis can be realized by immersing the polymer of Formula XX into a hydrochloric acid solution.

The pH of the solution can be between 0.1 and 6.5. In other embodiments, the pH of the solution is between 1 and 5. In some embodiments, the pH is about 1, 2, 3, 4, or 5. In some embodiments, the pH is 4. In other embodiments, the pH sensitive group can be removed under basic conditions and/or can be cleaved enzymatically.

As shown in Scheme II, the hydrophilic polymer of Formula XXI can increase in size, measured as particle diameter, as compared to the hydrophobic polymer of Formula XX. The increased size ($S_2$) can be between 1.01 and 100 times the original size ($S_1$). In some embodiments, the change in size from $S_1$ to $S_2$ is between 2 and 20 times, e.g., between 5 and 15, 5 and 10, 2 and 4, or 8 and 10 times, the original size.

As shown in Schemes III-IX, a compound, e.g., compound 1, 2, 3, 4, 5, 6, 7, 8, 9, 10, 11, 12, 13, 14, 15, or 16, is polymerized to form a polymer, e.g., compound 1a, 2a, 3a, 4a, 5a, 6a, 7a, 8a, 9a, 10a, 11a, 12a, 13a, 14a, 15a, or 16a. Any method of polymerization described herein can be used for this transformation. For example, compound 1, 2, 3, 4, 5, 6, 7, 8, 9, 10, 11, 12, 13, 14, 15, or 16 can be reacted with a free-radical initiator, such as 2,2'-azobis(2-methylpropionitrile) (AIBN). The resulting compound 1a, 2a, 3a, 4a, 5a, 6a, 7a, 8a, 9a, 10a, 11a, 12a, 13a, 14a, 15a, or 16a is a hydrophobic polymer with a pH sensitive group. Any method of acid catalyzed hydrolysis known in the art can be used to cleave the pH sensitive group, as described herein. Alternatively, an enzyme can cleave the protecting group. For example, compound 1a, 2a, 3a, 4a, 5a, 6a, 7a, 8a, 9a, 10a, 11a, 12a, 13a, 14a, 15a, or 16a can be immersed in a hydrochloric acid solution. The resulting compound 1b, 2b, 3b, 4b, 5b, 6b, 7b, 8b, 9b, 10b, 11b, 12b, 13b, 14b, 15b, or 16b is a hydrophilic polymer and can increase in size, as measured by particle diameter, between 1.01 and 100 or more (it is much greater than 10) times the original size of compound 1a, 2a, 3a, 4a, 5a, 6a, 7a, 8a, 9a, 10a, 11a, 12a, 13a, 14a, 15a, or 16a, respectively. For example, compound 1a, 2a, 3a, 4a, 5a, 6a, 7a, 8a, 9a, 10a, 11a, 12a, 13a, 14a, 15a, or 16a can be exposed to an acidic solution for various periods of time. Longer periods of exposure can lead to greater swelling. Alternative methods of achieving greater increase in diameter, or growth in particle size, include raising the temperature and/or lowering the pH. The degree to which the particle grows can be reduced by adding in one or more difunctional crosslinkers or co-monomers. These di-acrylate species provide crosslinking between the polymer chains further restricting the size of the particle upon expansion. A co-monomer, such as benzyl methacrylate, that is not pH-labile and may be hydrophobic in nature can induce decreased swelling in the particle. In some embodiments, cross-linker is 1,4-benzyl-diacrylate.

Scheme III

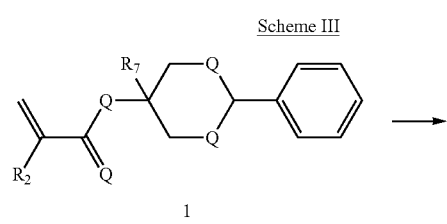

1

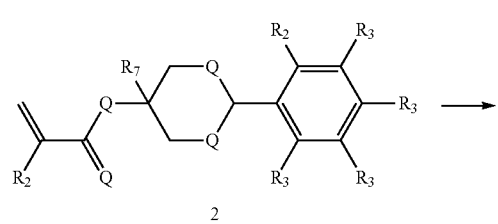

1a

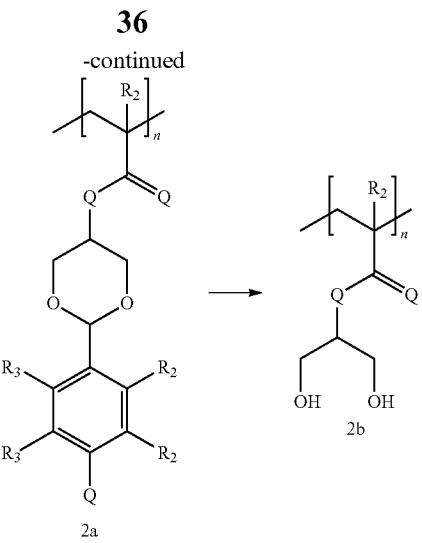

2a

2b

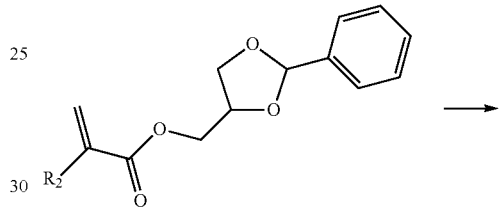

3

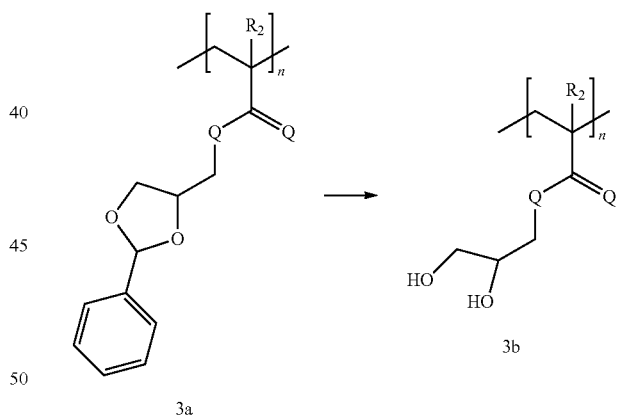

3a

3b

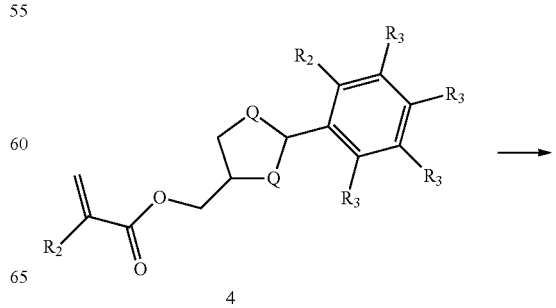

2

4

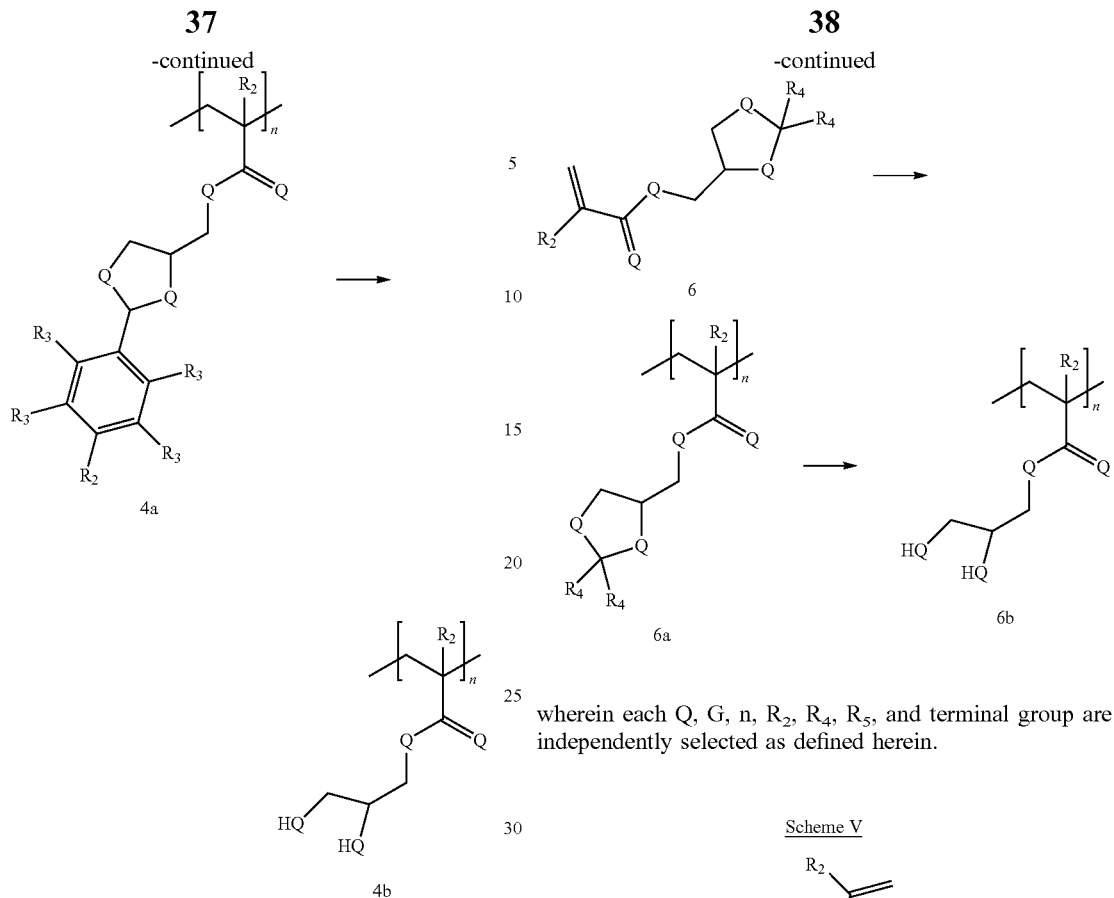
wherein each Q, G, n, R$_2$, R$_3$, R$_7$, and terminal group are independently selected as defined herein.
Scheme IV
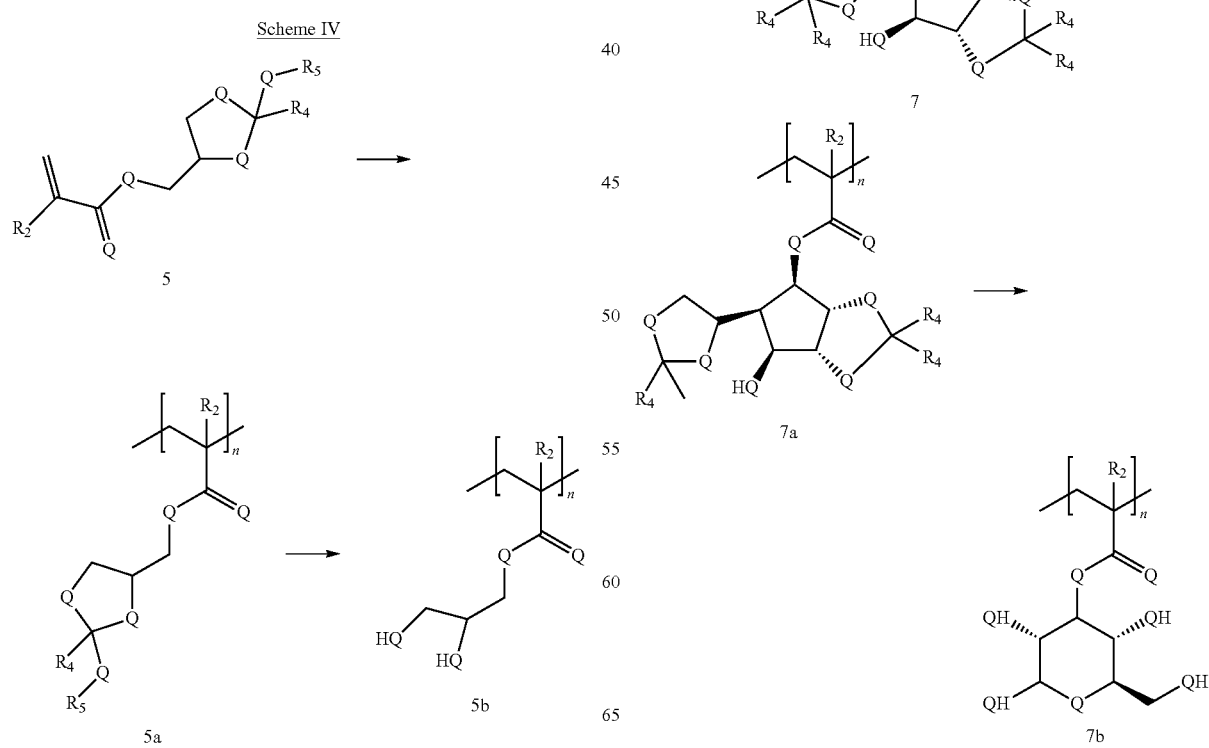
wherein each Q, G, n, R$_2$, R$_4$, R$_5$, and terminal group are independently selected as defined herein.
Scheme V

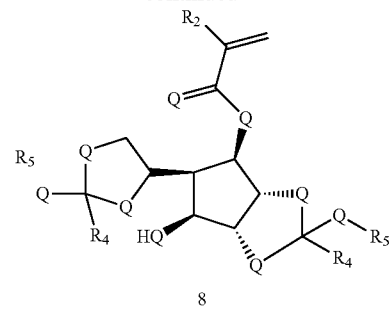
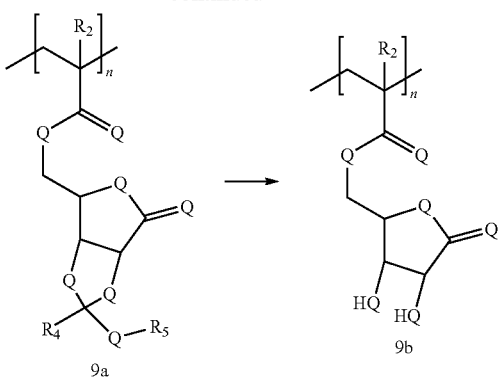
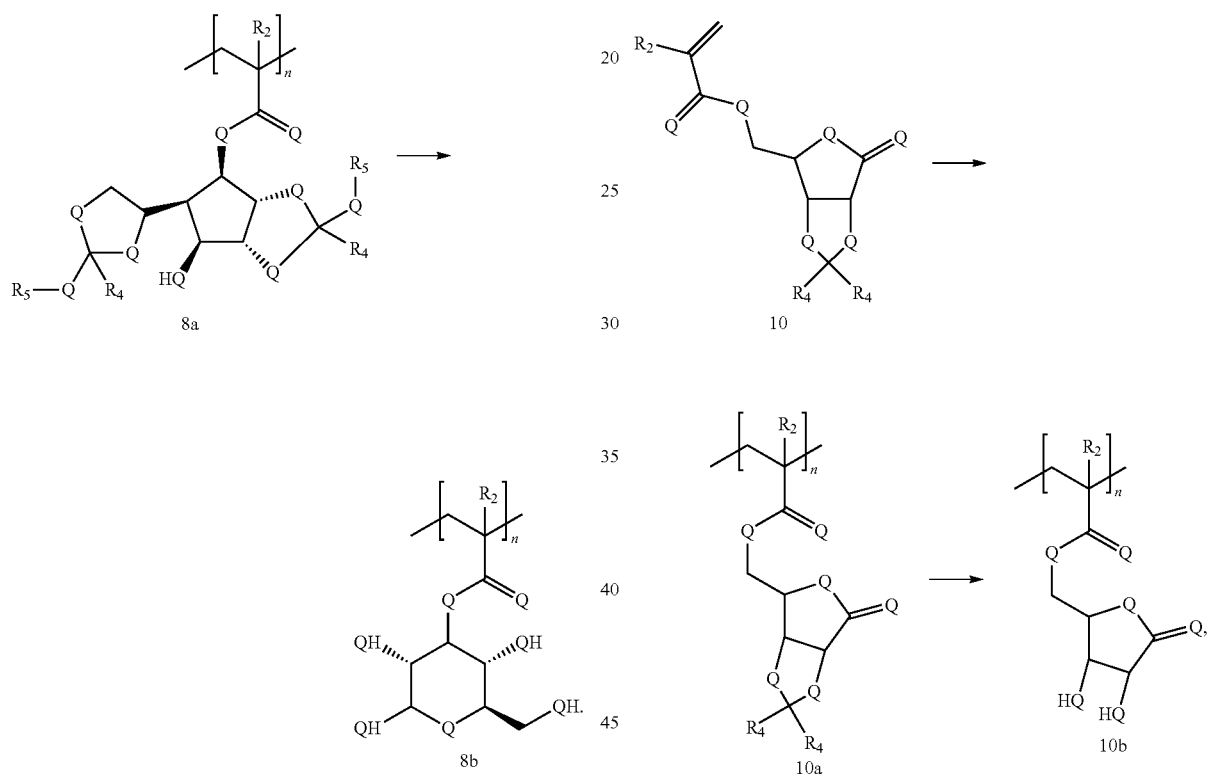
wherein each Q, G, n, R$_2$, R$_4$, R$_5$, and terminal group are independently selected as defined herein.
wherein each Q, G, n, R$_2$, R$_4$, R$_5$, and terminal group are independently selected as defined herein.
Scheme VI
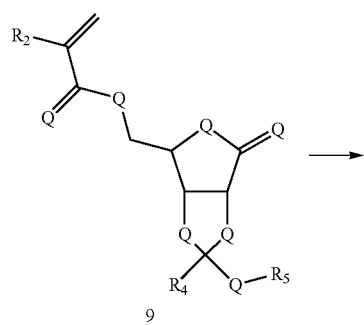
Scheme VII
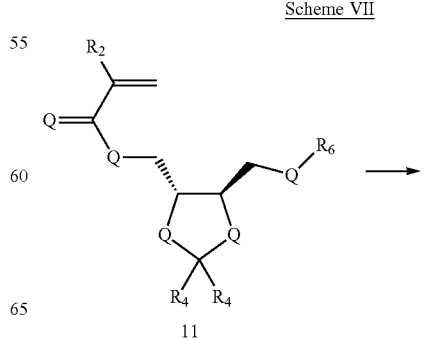

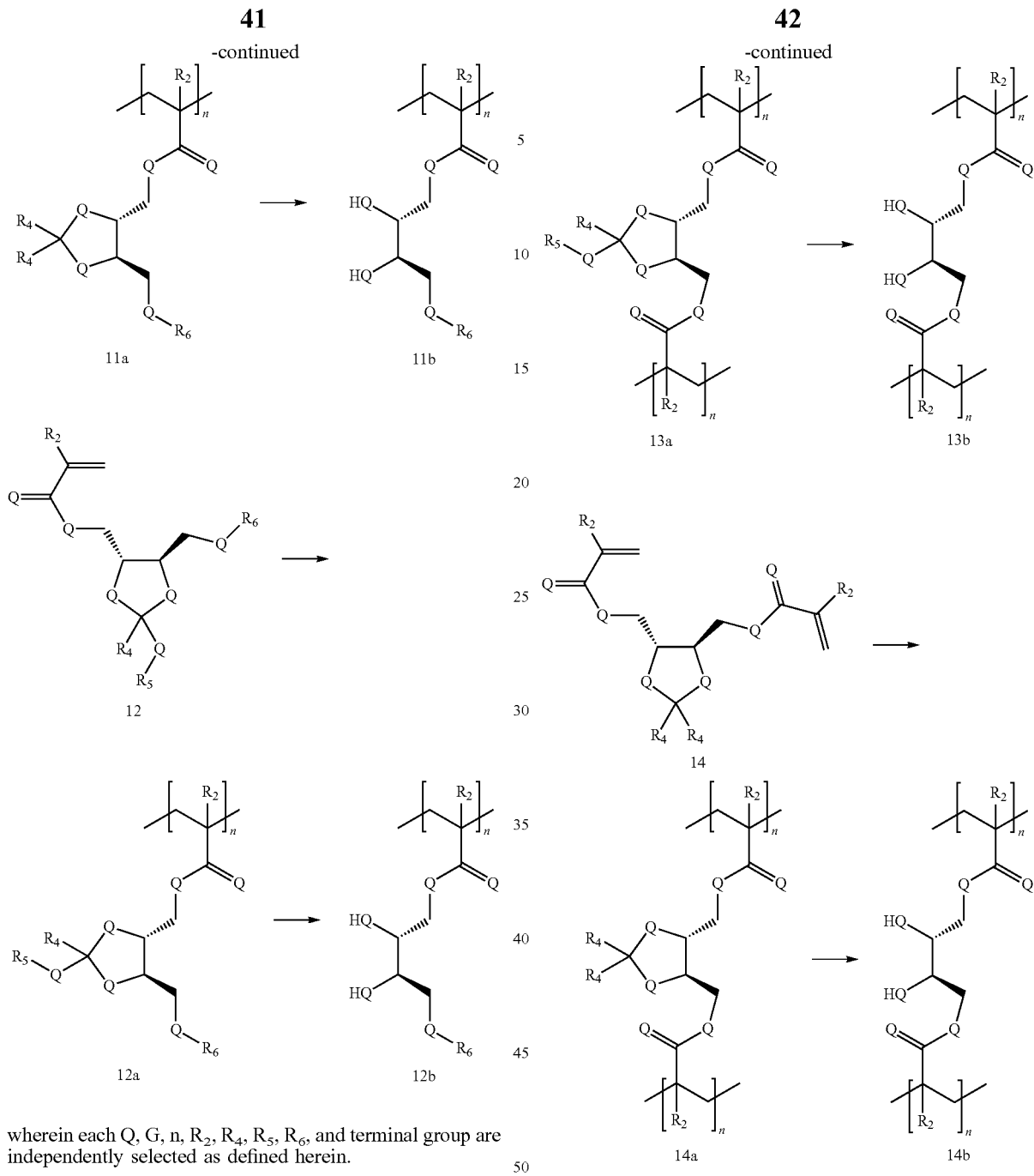
wherein each Q, G, n, R$_2$, R$_4$, R$_5$, R$_6$, and terminal group are independently selected as defined herein.
Scheme VIII
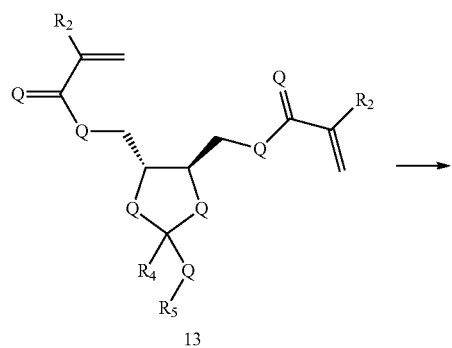
wherein each Q, G, n, R$_2$, R$_4$, R$_5$, and terminal group are independently selected as defined herein.
Scheme IX
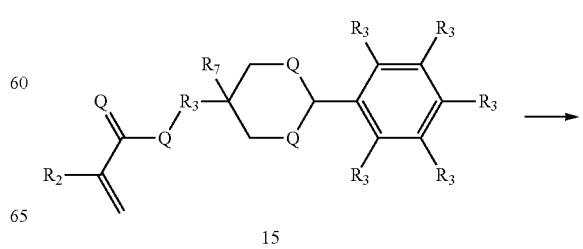

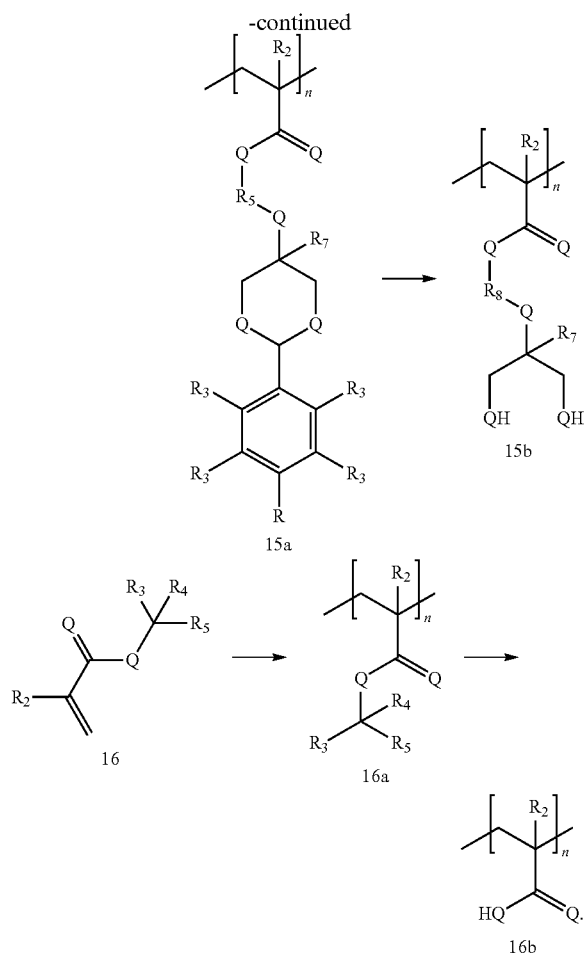

wherein each Q, G, n, R$_2$, R$_3$, R$_4$, R$_5$, R$_7$, R$_8$, and terminal group are independently selected as defined herein.

Provided herein are homopolymers prepared by polymerizing a compound of Formula I. In some embodiments, compounds of Formula I can be co-polymerized with any acryl monomer described herein or known in the art. For example, Compound 1 can be co-polymerized with Compound 2. Compound 3 can be co-polymerized with any acryl monomer known in the art, for example, methyl methacrylate.

In other embodiments, any compounds of Formula I can be co-polymerized with any acryl monomer described herein or known in the art to produce a random copolymer, a block copolymer, alternating, or a graft copolymer using any methods known in the art.

In additional embodiments, any compounds of Formula I can be co-polymerized with any acryl monomer described herein or known in the art to yield a linear, branched, star, or comb polymer, again, using any methods known in the art.

Any ratio of a single monomer relative to another monomer can be used to form a copolymer. Different ratios of monomer units impart different physical and chemical properties to the copolymer. Properties of interest include, but are not limited to, thermal transition temperature, bulk strength, crystallinity, porosity, flexibility (ability to be flexed repeatedly or malleable along surgical surfaces etc) or elasticity, hydrophobicity, changes in affinity to other surfaces or membranes and interactions with various cell types etc.

Thus, by varying monomer ratios, it is possible to afford a copolymer with desired characteristics. For example, introduction of a bulky hydrophobic side group will make the polymer more hydrophobic and reduce the rate of hydrolysis of the protecting group. These changes may also result in the particle having a smaller change in volume upon swelling. Changes may result in drug release, uptake by tumors, biocompatibility or dissolution by enzymes etc. including, but not limited to, intracellular degradation such as that within endosomes.

Various types of particles can be formed from these monomers and polymers. Any of the polymeric particles or films described herein can be made to also incorporate agents for optical, ultrasound, PET, CT, SPECT, MRI, x-ray or other methods of detection of the particle at the tissue site. Any method known in the art can be used to form a polymer/agent complex from the monomers and polymers described herein.

The polymers described herein can be used to produce polymer films or sheets using methods known in the art. For example, a monomer and a free-radical initiator, such as 2,2'-azobis(2-methylpropionitrile) (AIBN), can be dissolved in tetrahydrofuran. In some embodiments, the solution also contains a drug such as a chemotherapeutic drug, e.g., Paclitaxel. The solution can be purged of all dissolved oxygen by holding it under a nitrogen atmosphere while performing freeze-pump-thaw cycles on it. The solution is heated to 70° C. to allow for polymerization overnight. The resulting polymer can be precipitated in cold methanol, and isolated through decanting. The polymer is dissolved in dicholoromethane and small volume of this solution is spread on a glass slide to allow evaporation of the solvent; the result is a polymer film.

The polymers described herein can be used to product micro- or nanoparticles using methods known in the art. For example, a "water in oil emulsion technique" is described by Edlund and co-workers (see Edlund et al., Adv. Polymer Sci., 157:67-112, 2001; and Wang et al., Chem. Pharm. Bull., (Tokyo) 44:1935, 1996). Briefly, a polymer is dissolved in dichloromethane using a vortexing device. In some embodiments, the polymer is dissolved in dichloromethane along with an agent, such as paclitaxel. The solution is placed in a 5% polyvinyl alcohol surfactant and vortexed (or sonicated using a probe tip sonicator) and stirred for 16 hours to produce microparticles. The nanoparticles are collected and washed with distilled/deionized water and lyophilized.

To produce nanoparticles, one can, for example, use a miniemulsion polymerization method (see, e.g., Landfester et al., Macromolecules, 32:5222-8, 1999). Briefly, a monomer as described herein and a free-radical initiator (such as Cl$_2$, 2,2'-azobis(2-methylpropionitrile) (AIBN), or di-t-butylperoxide) are dissolved in a solvent, such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), or dimethyl sulfoxide. In some embodiments, an agent, such as paclitaxel, or a fluorophore, such as rhodamine B, is also dissolved in the solvent. The solution is mixed with a stabilizing surfactant, such as a solution of sodium dodecyl sulfate, in a buffer solution. This mixture is sonicated for 30 minutes (1 second pulses with a 2 second delay) with 30 W of power, which forms the miniemulsion and allows the solvent to evaporate. The miniemulsion is transferred into a temperature-controlled oil bath and stirred at 65° C. for 2 hours to initiate the free-radical polymerization. Optionally, the resulting polymeric nanospheres are dialyzed, e.g., against 5 mM pH 8 phosphate buffer, acetate buffer, bicarbonate buffer, or sodium citrate buffer, e.g., over one day, to remove excess surfactant and salts. Besides the AIBN method, the nanoparticles can be prepared using APS and TEMED, Eosin Y with 1-vinyl-2-pyrrolidoneand light, or KPS and heat to conduct the polymerization.

Alternatively, nanoparticles can be produced by photoinitiation. For example, a monomer as described herein can be dissolved in a solvent, such as hexane, benzene, toluene, diethyl ether, chloroform, ethyl acetate, dichloromethane, 1,4-dioxane, tetrahydrofuran (THF), acetone, acetonitrile (MeCN), dimethylformamide (DMF), or dimethyl sulfoxide. In some embodiments, an agent, such as paclitaxel is also dissolved in the solvent. The solvent is removed via rotary evaporation until a viscous mixture remains. The viscous mixture is mixed with a stabilizing surfactant solution, such as sodium dodecyl sulfate, in a buffer solution. The mixture is then sonicated for, for example, 30 minutes (1 second pulses with a 2 second delay) with about 30 W of power, forming the miniemulsion and allowing the solvent to partially evaporate. Eosin Y and 1-vinyl-2-pyrrolidone are added to the emulsion. The mixture is then exposed to light from a source such as a mercury arc lamp while the solution is stirred vigorously. The resulting particles are stirred overnight while open to the air to allow any remaining solvent to evaporate. Optionally, the polymeric nanoparticles can be dialyzed against a buffer solution to remove excess surfactant and salts.

In some embodiments, the diameter of the particles formed is between 1 nm and 50 microns, e.g., between 10 nm and 1 micron, between 50 nm and 1 micron, between 100 nm and 500 nm or between 1 and 50 microns.

If needed, any method known in the art for encapsulating an agent, such as a therapeutic agent, within a polymeric particle can be used to form a polymer/agent complex. For example, an oil emulsion technique can be used to form paclitaxel containing particles of Formula XX. A polymer of Formula XX can be dissolved in a solvent, such as dichloromethane, in the presence of an agent, such as a therapeutic agent, e.g., a chemotherapeutic agent, such as paclitaxel. The polymer/paclitaxel solution is vortexed. A surfactant solution, such as 5% polyvinyl alcohol, is added to the polymer/paclitaxel solution, and the resulting solution is vortexed for about 15 minutes followed by stirring for about 16 hours. The resulting particles are collected, washed with water, and lyophilized. In some embodiments, the encapsulation efficiency of the agent (e.g., paclitaxel) by the particles using this technique is between 1-99%. In another embodiment, the encapsulation efficiency of paclitaxel by the particles using this technique is between 1-95%.

In some embodiments, the polymeric particle comprises an oligomer or polymer comprising a repeat unit represented by Formula XX:

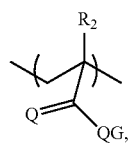

XX wherein:
Q is selected from the group consisting of O, S, Se, and NH;

G is selected from the group consisting of the following structures:

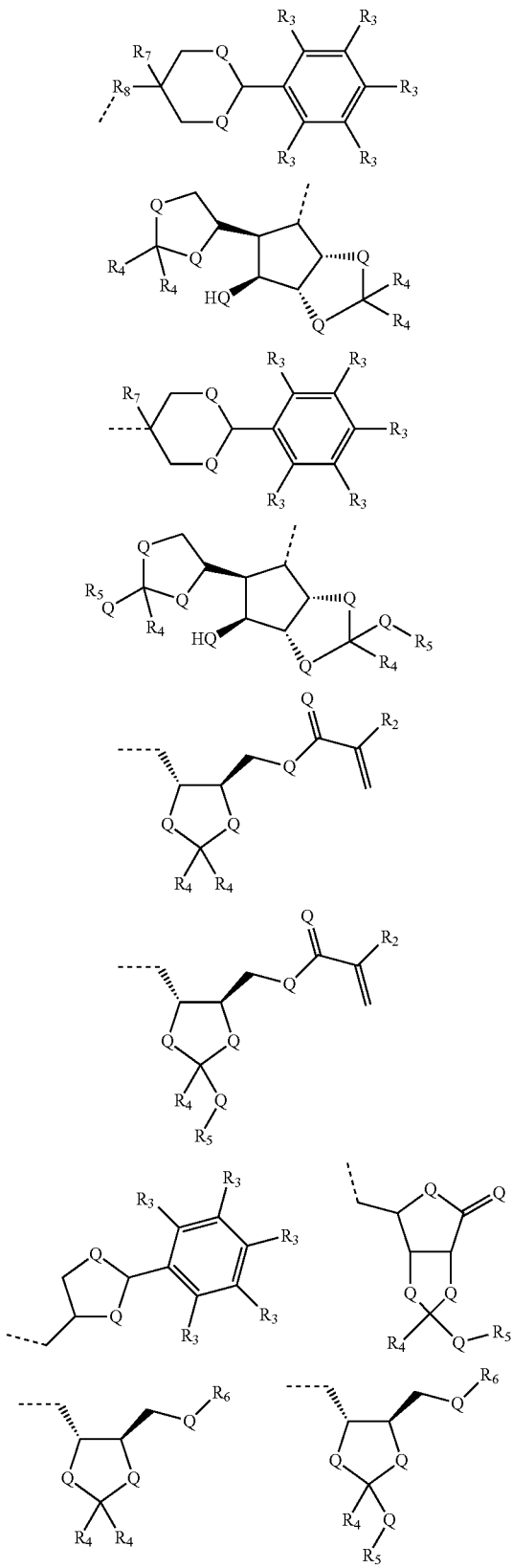

-continued

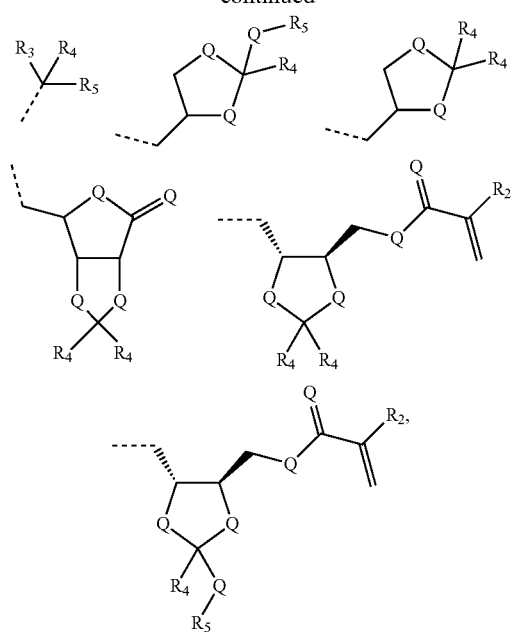

wherein

- R$_2$ is selected from the group consisting of hydrogen, a straight or branched alkyl, cycloalkyl, aryl, olefin, silyl, alkylsilyl, arylsilyl, alkylaryl, arylalkyl, and fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents; one R$_3$ is selected from the group consisting of methoxy, ethoxy, amino, nitro, cycloalkyl, aryl, olefin, silyl, alkylsilyl, arylsilyl, alkylaryl, and arylalkyl chain of 1-10 carbons; and the remaining R$_3$ are each independently selected from the group consisting of hydrogen, methoxy, ethoxy, amino, a straight and branched alkyl, cycloalkyl, aryl, olefin, silyl, alkylsilyl, arylsilyl, alkylaryl, and arylalkyl chain of 1-10 carbons;
- R$_4$, R$_5$, and R$_6$ are each independently selected from the group consisting of a straight or branched alkyl, cycloalkyl, aryl, olefin, silyl, alkylsilyl, arylsilyl, alkylaryl, and arylalkyl chain of 1-10 carbons; and
- R$_7$ and R$_8$ are each independently selected from the group consisting of hydrogen, a straight or branched alkyl, cycloalkyl, aryl, olefin, alkylaryl, and arylalkyl chain of 1-50 carbons, wherein each alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

In some embodiments, G is

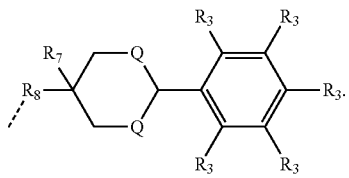

In some embodiments, Q is O.
In some embodiments, R$_2$ is hydrogen or methyl.
In some embodiments, R$_3$ is hydrogen or methoxy.
In some embodiments, the polymeric particle comprises an oligomer or polymer comprising a repeat unit

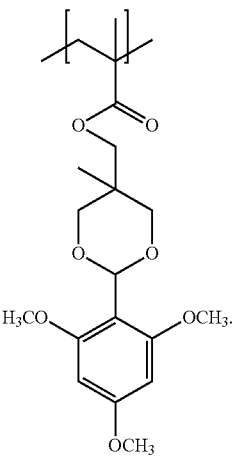

In some embodiments, the polymeric particle comprises an oligomer or polymer comprising a monomer of Formula XX and the oligomer or polymer is cross-linked.

In some embodiments, the polymeric particle comprises an oligomer or polymer comprising a monomer of Formula XX, and the polymeric particle comprises a first volume at a first pH, and a second volume at a second pH, different from the first pH, wherein the second volume is 1× or more greater than the first volume when the second pH is lower than the first pH.

In some embodiments, the polymeric particle comprises an oligomer or polymer comprising a monomer of Formula XX, and the polymeric particle comprises a first volume at a first pH, and a second volume at a second pH, different from the first pH, wherein the second volume is 1.1× or more greater than the first volume when the second pH is lower than the first pH.

In some embodiments, the polymeric particle comprises a co-polymer comprising two or more of the monomers described herein above.

The invention can be further illustrated by any one of the following numbered paragraphs:

1. A method of delivering, localizing or concentrating an agent to a tissue location in a subject, the method comprising administering to the subject an empty polymeric particle prior to, simultaneously with or after delivering an agent to the subject, wherein the empty polymeric particle undergoes a change in volume on contact with the tissue location and becomes lodged, embedded, immobilized or entrapped at the tissue location, and wherein the empty polymeric concentrates the agent at the tissue location.

2. The method of paragraph 1, wherein amount of the agent at the tissue location is at least 5% higher relative to when no polymeric particle is administered to the subject.
3. The method of any of paragraphs 1-2, wherein the tissue location is selected from the group consisting of: (i) a treated or untreated tumor or cavity; (ii) within a treated or untreated tumor or cavity; (iii) a target site of disease away from a surgical margin; (iv) a target site of disease away from a tumor; (v) a surgical resection margin at a treated or untreated tumor or cavity; (vi) a lymph node; (vii) within an airway or lumen; (viii) within an organ; (ix) site of infection; and site of inflammation.
4. The method of paragraph 3, wherein the organ is lymph node, colon, small intestine, large intestine, bladder, ovary, urethra, uterus, breast, prostate, thyroid gland, stomach, kidney, liver, heart, or brain.
5. The method of any of paragraphs 1-4, wherein the agent is selected from the group consisting small organic or inorganic molecules, saccharines, oligosaccharides, polysaccharides, biological macromolecules, peptides, proteins, peptide analogs and derivatives, peptidomimetics, antibodies, fragments or portions of antibodies, nucleic acids, nucleic acid analogs and derivatives, extracts made from biological materials, animal tissues, naturally occurring or synthetic compositions, and any combinations thereof
6. The method of any of paragraphs 1-5, wherein the agent is a therapeutic agent or a diagnostic agent.
7. The method of any of paragraphs 1-6, wherein the agent is selected from anticancer agents, immune modulator agents, anti-inflammatory agents, antibiotics, and any combinations thereof
8. The method of any of paragraphs 1-7, wherein the agent is selected from the group consisting of asparaginase; bleomycin; busulfan; capecitabine; carboplatin; carmustine chlorambucil; cisplatin; cyclophosphamide; cytarabine; cyclosporine, FK506; dacarbazine; dactinomycin; daunorubicin; dexrazoxane; docetaxel; doxorubicin; etoposide; floxuridine; fludarabine; fluorouracil; gemcitabine; hydroxyurea; idarubicin; ifosfamide; irinotecan; lomustine; link-F3, link-N3, mechlorethamine; melphalan; mercaptopurine; methotrexate; mitomycin; mitotane; mitoxantrone; paclitaxel; pemetrexed; pentostatin; plicamycin; procarbazine; pycnidione; rituximab; streptozocin; teniposide; thioguanine; thiotepa; vinblastine; vincristine; vinorelbine; 10-hydrocamptothecin and derivatives thereof and combinations thereof
9. The method of any of paragraphs 1-8, wherein the empty polymeric particle and the agent are administered within 96 hours of each other.
10. The method of any of paragraphs 1-9, wherein the empty polymeric particle comprises an agent which is different from the agent delivered prior to, simultaneously with or after providing the empty polymeric particle to the tissue.
11. The method of paragraph 10, wherein the empty polymeric particle comprises the agent selected from the group consisting of asparaginase; bleomycin; busulfan; capecitabine; carboplatin; carmustine chlorambucil; cisplatin; cyclophosphamide; cytarabine; cyclosporine, FK506; dacarbazine; dactinomycin; daunorubicin; dexrazoxane; docetaxel; doxorubicin; etoposide; floxuridine; fludarabine; fluorouracil; gemcitabine; hydroxyurea; idarubicin; ifosfamide; irinotecan; lomustine; link-F3, link-N3, mechlorethamine; melphalan; mercaptopurine; methotrexate; mitomycin; mitotane; mitoxantrone; paclitaxel; pemetrexed; pentostatin; plicamycin; procarbazine; pycnidione; rituximab; streptozocin; teniposide; thioguanine; thiotepa; vinblastine; vincristine; vinorelbine; 10-hydrocamptothecin and derivatives thereof and combinations thereof.
12. The method of any of paragraphs 1-11, wherein the polymeric particle comprises a core that is more hydrophobic than the aqueous solution is suspended into thereby being capable of localizing into a tissue site and concentrating a subsequently delivered agent.
13. The method of any of paragraphs 1-12, wherein the polymeric particle comprises a pH-sensitive, photo-sensitive or a thermosensitive monomer, thereby allowing the polymeric particle to undergo a change in volume when the pH changes, upon photolysis or thermal treatment, respectively.
14. The method of any of paragraphs 1-13, wherein the polymeric particle comprises an oligomer or a polymer comprising a monomer represented by Formula XX:

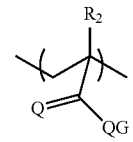

wherein:

Q is selected from the group consisting of O, S, Se, and NH;

G is selected from the group consisting of the following structures:

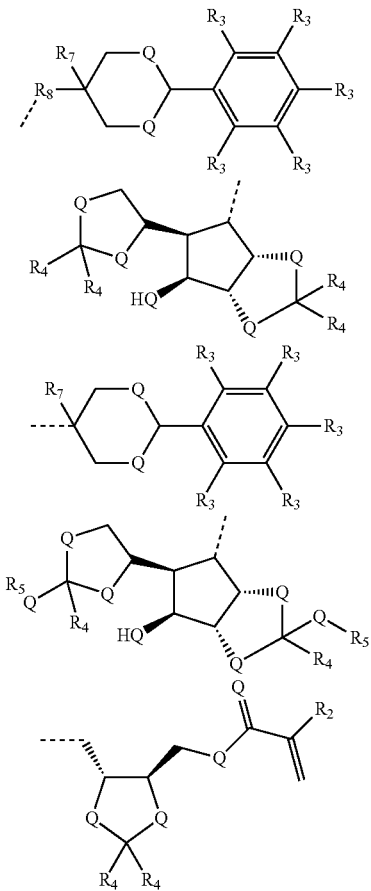

-continued

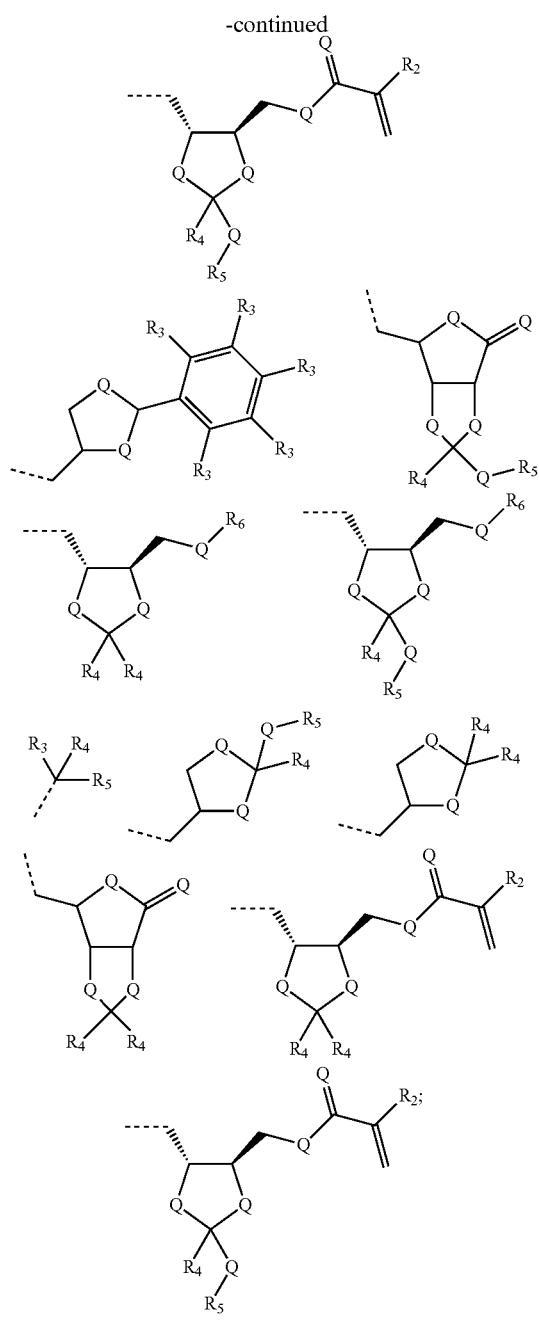

$R_2$ is selected from the group consisting of hydrogen, a straight or branched alkyl, cycloalkyl, aryl, olefin, silyl, alkylsilyl, arylsilyl, alkylaryl, arylalkyl, and fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

one $R_3$ is selected from the group consisting of methoxy, ethoxy, amino, nitro, cycloalkyl, aryl, olefin, silyl, alkylsilyl, arylsilyl, alkylaryl, and arylalkyl chain of 1-10 carbons;

and the remaining $R_3$ are each independently selected from the group consisting of hydrogen, methoxy, ethoxy, amino, a straight and branched alkyl, cycloalkyl, aryl, olefin, silyl, alkylsilyl, arylsilyl, alkylaryl, and arylalkyl chain of 1-10 carbons;

$R_4$, $R_5$, and $R_6$ are each independently selected from the group consisting of a straight or branched alkyl, cycloalkyl, aryl, olefin, silyl, alkylsilyl, arylsilyl, alkylaryl, and arylalkyl chain of 1-10 carbons; and $R_7$ and $R_8$ are each independently selected from the group consisting of hydrogen, a straight or branched alkyl, cycloalkyl, aryl, olefin, alkylaryl, and arylalkyl chain of 1-50 carbons, wherein each alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

15. The method of paragraph 14, wherein G is

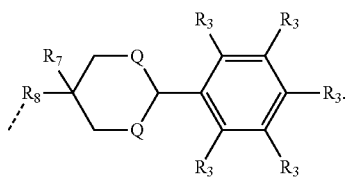

16. The method of any of paragraphs 14-15, wherein Q is O.
17. The method of any of paragraphs 14-16, wherein $R_2$ is hydrogen or methyl.
18. The method of any of paragraphs 14-17, wherein $R_3$ is hydrogen or methoxy.
19. The method of any of paragraphs 14-18, wherein the oligomer or the polymer comprises the monomer

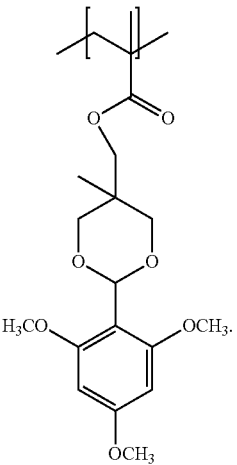

20. The method of any of paragraphs 1-19, wherein the polymeric particle comprises cross-linked oligomer or polymer.
21. The method of any of paragraphs 1-20, wherein the polymeric particle comprises a first volume at a first pH, and a second volume at a second pH, different from the first pH, wherein the second volume is 1× or more greater than the first volume when the second pH is lower than the first pH.
22. The method of any of paragraphs 1-21, wherein polymeric particle further comprises a microparticle or a nanoparticle.

23. The method of paragraph 22, wherein the microparticle or the nanoparticle has a diameter between about 2 nm and 1 microns.
24. The method of any of paragraphs 1-23, wherein the polymeric particle is administered locally to the tissue location.
25. The method of any of paragraphs 1-24, wherein the agent is administered locally to the tissue location or location of the polymeric particle at the tissue location.
26. The method of any of paragraphs 1-25, wherein the subject is need of treatment for cancer, recurrence of a malignancy, lymph node metastasis, inflammation, infection, wound healing, abnormal scar formation, a chronic condition, or post-operative pain.
27. The method of any of paragraphs 1-26, wherein the polymeric particle is formulated with a pharmaceutically acceptable carrier.
28. A method of treating a cancer or tumor in a subject, the method comprising administering to the subject in need thereof an empty polymeric particle prior to, simultaneously with or after administering an anti-cancer agent, wherein the empty polymeric particle undergoes a change in volume on contact with the tumor and becomes lodged, embedded, immobilized or entrapped in the tumor, and wherein the empty polymeric concentrates the anti-cancer agent in the tumor.
29. The method of paragraph 28, wherein the tumor is a malignant or benign tumor.
30. The method of paragraph 28-29, wherein the tumor is a primary tumor or a metastatic tumor.
31. The method of any of paragraphs 28-30, wherein the cancer is selected from the group consisting of lung, colon, prostate, pancreatic, ovarian, breast, mesothelioma, sarcoma, stomach, oesophageal, endometrium, bladder, cervix uteri, oral, paediatric tumours, lymphoma, myeloma, seminoma, Hodgkin and malignant hemopathies, leukemia, lymphoma, melanoma, bowel, rectal, colorectal, brain, liver, prostate, testicular, retinoblastoma, and any combinations thereof
32. The method of any of paragraphs 28-31, the polymeric particle is administered locally to the tumor.
33. The method of any of paragraphs 28-32, wherein the agent is administered locally to the tumor or location of the polymeric particle in the tumor.
34. The method of any of paragraphs 28-33, wherein the anti-cancer agent is selected from the group consisting small organic or inorganic molecules, saccharines, oligosaccharides, polysaccharides, biological macromolecules, peptides, proteins, peptide analogs and derivatives, peptidomimetics, antibodies, fragments or portions of antibodies, nucleic acids, nucleic acid analogs and derivatives, extracts made from biological materials, animal tissues, naturally occurring or synthetic compositions, and any combinations thereof
35. The method of any of paragraphs 28-34, wherein the anti-cancer agent is selected from the group consisting of asparaginase; bleomycin; busulfan; capecitabine; carboplatin; carmustine chlorambucil; cisplatin; cyclophosphamide; cytarabine; cyclosporine, FK506; dacarbazine; dactinomycin; daunorubicin; dexrazoxane; docetaxel; doxorubicin; etoposide; floxuridine; fludarabine; fluorouracil; gemcitabine; hydroxyurea; idarubicin; ifosfamide; irinotecan; lomustine; link-F3, link-N3, mechlorethamine; melphalan; mercaptopurine; methotrexate; mitomycin; mitotane; mitoxantrone; paclitaxel; pemetrexed; pentostatin; plicamycin; procarbazine; pycnidione; rituximab; streptozocin; teniposide; thioguanine; thiotepa; vinblastine; vincristine; vinorelbine; 10-hydrocamptothecin and derivatives thereof and combinations thereof
36. The method of any of paragraphs 38-35, wherein the empty polymeric particle and the agent are administered within 96 hours of each other.
37. The method of any of paragraphs 38-36, wherein the empty polymeric particle comprises an agent which is different from the agent delivered prior to, simultaneously with or after providing the empty polymeric particle to the tissue.
38. The method of paragraph 37, wherein the empty polymeric particle comprises the agent selected from the group consisting of asparaginase; bleomycin; busulfan; capecitabine; carboplatin; carmustine chlorambucil; cisplatin; cyclophosphamide; cytarabine; cyclosporine, FK506; dacarbazine; dactinomycin; daunorubicin; dexrazoxane; docetaxel; doxorubicin; etoposide; floxuridine; fludarabine; fluorouracil; gemcitabine; hydroxyurea; idarubicin; ifosfamide; irinotecan; lomustine; link-F3, link-N3, mechlorethamine; melphalan; mercaptopurine; methotrexate; mitomycin; mitotane; mitoxantrone; paclitaxel; pemetrexed; pentostatin; plicamycin; procarbazine; pycnidione; rituximab; streptozocin; teniposide; thioguanine; thiotepa; vinblastine; vincristine; vinorelbine; 10-hydrocamptothecin and derivatives thereof and combinations thereof.
39. The method of any of paragraphs 28-38, wherein the polymeric particle comprises a core that is more hydrophobic than the aqueous solution is suspended into thereby being capable of localizing into a tissue site and concentrating a subsequently delivered agent.
40. The method of any of paragraphs 28-40, wherein the polymeric particle comprises a pH-sensitive, photo-sensitive or a thermosensitive monomer, thereby allowing the polymeric particle to undergo a change in volume when the pH changes, upon photolysis or thermal treatment, respectively.
41. The method of any of paragraphs 28-40, wherein the polymeric particle comprises an oligomer or a polymer comprising a monomer represented by Formula XX:

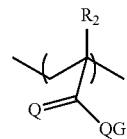

XX wherein:

Q is selected from the group consisting of O, S, Se, and NH;

G is selected from the group consisting of the following structures:

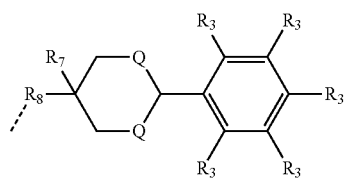

-continued

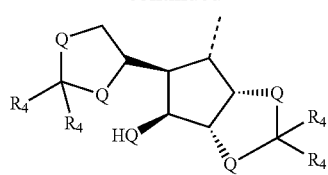
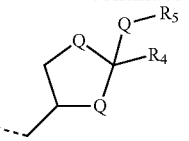

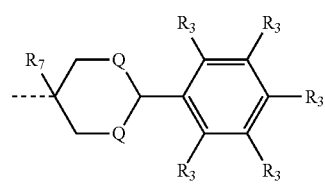

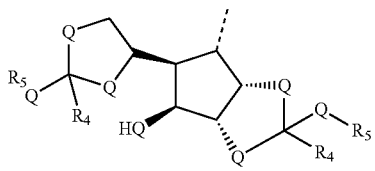
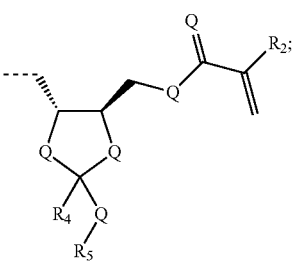

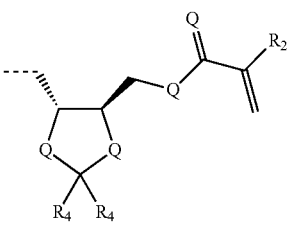

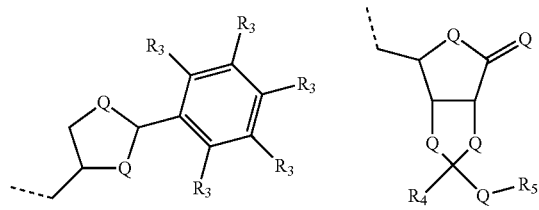

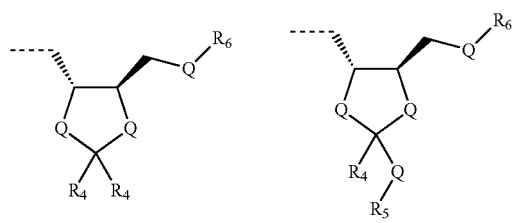

$R_2$ is selected from the group consisting of hydrogen, a straight or branched alkyl, cycloalkyl, aryl, olefin, silyl, alkylsilyl, arylsilyl, alkylaryl, arylalkyl, and fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

one $R_3$ is selected from the group consisting of methoxy, ethoxy, amino, nitro, cycloalkyl, aryl, olefin, silyl, alkylsilyl, arylsilyl, alkylaryl, and arylalkyl chain of 1-10 carbons;

and the remaining $R_3$ are each independently selected from the group consisting of hydrogen, methoxy, ethoxy, amino, a straight and branched alkyl, cycloalkyl, aryl, olefin, silyl, alkylsilyl, arylsilyl, alkylaryl, and arylalkyl chain of 1-10 carbons;

$R_4$, $R_5$, and $R_6$ are each independently selected from the group consisting of a straight or branched alkyl, cycloalkyl, aryl, olefin, silyl, alkylsilyl, arylsilyl, alkylaryl, and arylalkyl chain of 1-10 carbons; and $R_7$ and $R_8$ are each independently selected from the group consisting of hydrogen, a straight or branched alkyl, cycloalkyl, aryl, olefin, alkylaryl, and arylalkyl chain of 1-50 carbons, wherein each alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

42. The method of any of paragraphs 28-41, wherein the polymeric particle comprises an oligomer or a polymer comprising the monomer

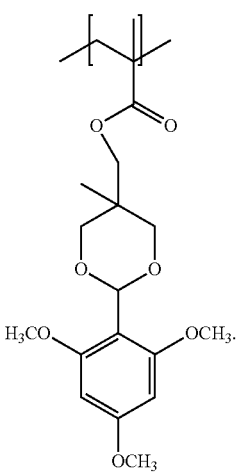

43. The method of any of paragraphs 28-42, wherein the polymeric particle comprises a cross-linked oligomer or polymer.
44. The method of any of paragraphs 28-43, wherein the polymeric particle comprises a first volume at a first pH, and a second volume at a second pH, different from the first pH, wherein the second volume is 1× or more greater than the first volume when the second pH is lower than the first pH.

Some Selected Definitions

Unless specific definitions are provided, e.g., as indicated above, the nomenclature used in connection with, and the laboratory procedures and techniques of, analytical chemistry, biochemistry, synthetic organic chemistry, and medicinal and pharmaceutical chemistry described herein are those known in the art. In the event that there is a plurality of definitions for terms herein, those in this section prevail.

As used herein, the abbreviations for any protective groups, amino acids, and other compounds are, unless indicated otherwise, in accord with their common usage, recognized abbreviations, or the IUPAC-IUB Commission on Biochemical Nomenclature, *Biochem.*, 11:942-944 (1972).

As used herein, use of the singular includes the plural unless specifically stated otherwise. As used herein, "or" means "and/or" unless stated otherwise. Furthermore, use of the term "including" as well as other forms, such as "includes," and "included," is not limiting.

By "treatment, prevention or amelioration" is meant delaying or preventing the onset of such a disorder or reversing, alleviating, ameliorating, inhibiting, slowing down or stopping the progression, aggravation or deterioration the progression or severity of such a condition. As used herein, the terms "treating" or "treatment" encompass responsive measures, e.g., designed to inhibit, slow or delay the onset of a symptom of a disease or disorder, achieve reduction of a symptom or disease state, and/or to alleviate, ameliorate, or lessen a disease or disorder and/or its symptoms. As used herein, amelioration of the symptoms of a particular disorder by administration of a particular compound or pharmaceutical composition refers to any lessening of severity, delay in onset, slowing of progression, or shortening of duration, whether permanent or temporary, lasting or transient that can be attributed to or associated with administration of the compound or composition.

In some embodiments, at least one symptom is alleviated by at least 20%, at least 30%, at least 40%, at least 50%, at least 60%, at least 70%, at least 80%, at least 90%, or at least 95% but not 100%, i.e. not a complete alleviation. In some embodiments, at least one symptom is completely alleviated.

As used herein, pharmaceutically acceptable derivatives of a compound include, but are not limited to, salts, esters, enol ethers, enol esters, acetals, ketals, orthoesters, hemiacetals, hemiketals, acids, bases, solvates, hydrates, PEGylation, or prodrugs thereof. Such derivatives can be readily prepared by those of skill in this art using known methods for such derivatization. The compounds produced can be administered to animals or humans without substantial toxic effects and either are pharmaceutically active or are prodrugs. Pharmaceutically acceptable salts include, but are not limited to, amine salts, such as but not limited to chloroprocaine, choline, N,N'-dibenzyl-ethylenediamine, ammonia, diethanolamine and other hydroxyalkylamines, ethylenediamine, N-methylglucamine, procaine, N-benzylphenethylamine, 1-para-chloro-benzyl-2-pyrrolidin-1'-ylmethyl-benzimidazole, diethylamine and other alkylamines, piperazine and tris(hydroxymethyl)-aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, aryl, heteroaryl, aralkyl, heteroaralkyl, cycloalkyl or heterocyclyl. Pharmaceutically acceptable enol esters include, but are not limited to, derivatives of formula C=C(OC(O)R) where R is hydrogen, alkyl, alkenyl, alkynyl, aryl, heteroaryl, aralkyl, heteroaralkyl, cycloalkyl or heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

"Alkyl" refers to an aliphatic hydrocarbon group which can be straight or branched having 1 to about 60 carbon atoms in the chain, and which preferably have about 6 to about 50 carbons in the chain. "Lower alkyl" refers to an alkyl group having 1 to about 8 carbon atoms. "Higher alkyl" refers to an alkyl group having about 10 to about 20 carbon atoms. The alkyl group can be optionally substituted with one or more alkyl group substituents which can be the same or different, where "alkyl group substituent" includes halo, amino, aryl, hydroxy, alkoxy, aryloxy, alkyloxy, alkylthio, arylthio, aralkyloxy, aralkylthio, carboxy, alkoxycarbonyl, oxo and cycloalkyl. There can be optionally inserted along the alkyl chain one or more oxygen, silicon, sulfur, or substituted or unsubstituted nitrogen atoms, wherein the nitrogen substituent is lower alkyl. "Branched" refers to an alkyl group in which a lower alkyl group, such as methyl, ethyl or propyl, is attached to a linear alkyl chain. Exemplary alkyl groups include methyl, ethyl, i-propyl, n-butyl, t-butyl, n-pentyl, heptyl, octyl, decyl, dodecyl, tridecyl, tetradecyl, pentadecyl and hexadecyl. Useful alkyl groups include branched or straight chain alkyl groups of 6 to 50 carbon, and also include the lower alkyl groups of 1 to about 4 carbons and the higher alkyl groups of about 12 to about 16 carbons.

"Alkenyl" refers to an alkyl group containing at least one carbon-carbon double bond. The alkenyl group can be optionally substituted with one or more "alkyl group substituents." Exemplary alkenyl groups include vinyl, allyl, n-pentenyl, decenyl, dodecenyl, tetradecadienyl, heptadec-8-en-1-yl and heptadec-8,11-dien-1-yl.

"Alkynyl" refers to an alkyl group containing a carbon-carbon triple bond. The alkynyl group can be optionally substituted with one or more "alkyl group substituents." Exemplary alkynyl groups include ethynyl, propargyl, n-pentynyl, decynyl and dodecynyl. Useful alkynyl groups include the lower alkynyl groups.

"Cycloalkyl" refers to a non-aromatic mono- or multicyclic ring system of about 4 to about 10 carbon atoms. The cycloalkyl group can be optionally partially unsaturated. The cycloalkyl group can be also optionally substituted with an aryl group substituent, oxo and/or alkylene. Representative monocyclic cycloalkyl rings include cyclopentyl, cyclohexyl and cycloheptyl. Useful multicyclic cycloalkyl rings include adamantyl, octahydronaphthyl, decalin, camphor, camphane, and noradamantyl.

"Aryl" refers to an aromatic carbocyclic radical containing about 6 to about 10 carbon atoms. The aryl group can be optionally substituted with one or more aryl group substituents, which can be the same or different, where "aryl group substituent" includes alkyl, alkenyl, alkynyl, aryl, aralkyl, hydroxy, alkoxy, aryloxy, aralkoxy, carboxy, aroyl, halo, nitro, trihalomethyl, cyano, alkoxycarbonyl, aryloxycarbonyl, aralkoxycarbonyl, acyloxy, acylamino, aroylamino, carbamoyl, alkylcarbamoyl, dialkylcarbamoyl, rylthio, alkylthio, alkylene and —NRR', where R and R' are each independently hydrogen, alkyl, aryl and aralkyl. Exemplary aryl groups include substituted or unsubstituted phenyl and substituted or unsubstituted naphthyl.

"Acyl" refers to an alkyl-CO— group, wherein alkyl is as previously described. Exemplary acyl groups comprise alkyl of 1 to about 30 carbon atoms. Exemplary acyl groups also include acetyl, propanoyl, 2-methylpropanoyl, butanoyl and palmitoyl.

"Aroyl" means an aryl-CO— group, wherein aryl is as previously described. Exemplary aroyl groups include benzoyl and 1- and 2-naphthoyl.

"Alkoxy" refers to an alkyl-O— group, wherein alkyl is as previously described. Exemplary alkoxy groups include methoxy, ethoxy, n-propoxy, i-propoxy, n-butoxy, and heptoxy.

"Aryloxy" refers to an aryl-O— group, wherein the aryl group is as previously described. Exemplary aryloxy groups include phenoxy and naphthoxy.

"Alkylthio" refers to an alkyl-S— group, wherein alkyl is as previously described. Exemplary alkylthio groups include methylthio, ethylthio, i-propylthio and heptylthio.

"Arylthio" refers to an aryl-S— group, wherein the aryl group is as previously described. Exemplary arylthio groups include phenylthio and naphthylthio.

"Aralkyl" refers to an aryl-alkyl- group, wherein aryl and alkyl are as previously described. Exemplary aralkyl groups include benzyl, phenylethyl and naphthylmethyl.

"Aralkyloxy" refers to an aralkyl-O— group, wherein the aralkyl group is as previously described. An exemplary aralkyloxy group is benzyloxy.

"Aralkylthio" refers to an aralkyl-S— group, wherein the aralkyl group is as previously described. An exemplary aralkylthio group is benzylthio.

"Dialkylamino" refers to an —NRR' group, wherein each of R and R' is independently an alkyl group as previously described. Exemplary alkylamino groups include ethylmethylamino, dimethylamino, and diethylamino.

"Alkoxycarbonyl" refers to an alkyl-O—CO— group. Exemplary alkoxycarbonyl groups include methoxycarbonyl, ethoxycarbonyl, butyloxycarbonyl, and t-butyloxycarbonyl.

"Aryloxycarbonyl" refers to an aryl-O—CO— group. Exemplary aryloxycarbonyl groups include phenoxy- and naphthoxy-carbonyl.

"Aralkoxycarbonyl" refers to an aralkyl-O—CO— group. An exemplary aralkoxycarbonyl group is benzyloxycarbonyl.

"Carbamoyl" refers to an $H_2N$—CO— group.

"Alkylcarbamoyl" refers to a R'RN—CO— group, wherein one of R and R' is hydrogen and the other of R and R' is alkyl as previously described.

"Dialkylcarbamoyl" refers to R'RN—CO— group, wherein each of R and R' is independently alkyl as previously described.

"Acyloxy" refers to an acyl-O— group, wherein acyl is as previously described.

"Acylamino" refers to an acyl-NH— group, wherein acyl is as previously described.

"Aroylamino" refers to an aroyl-NH— group, wherein aroyl is as previously described.

"Alkylene" refers to a straight or branched bivalent aliphatic hydrocarbon group having from 1 to about 30 carbon atoms. The alkylene group can be straight, branched, or cyclic. The alkylene group can be also optionally unsaturated and/or substituted with one or more "alkyl group substituents." There can be optionally inserted along the alkylene group one or more oxygen, sulphur, or substituted or unsubstituted nitrogen atoms, wherein the nitrogen substituent is alkyl as previously described. Exemplary alkylene groups include methylene (—$CH_2$—), ethylene (—$CH_2$—$CH_2$—), propylene (—$(CH_2)_3$—), cyclohexylene (—$C_6H_{10}$—), —CH=CH—CH=CH—, —$(CF_2)_n$$(CH_2)_m$—, wherein n is an integer from about 1 to about 50 and m is an integer from 0 to about 50, —$(CH_2)_n$—N(R)—$(CH_2)_m$—, wherein each of m and n is independently an integer from 0 to about 50 and R is hydrogen or alkyl, methylenedioxy (—O—$CH_2$—O—) and ethylenedioxy (—O—$(CH_2)_2$—O—). An alkylene group can have about 2 to about 3 carbon atoms and can further have 6-50 carbons.

"Halo" or "halide" refers to fluoride, chloride, bromide, or iodide.

"Genetic material" refers generally to nucleotides and polynucleotides, including deoxyribonucleic acid (DNA), ribonucleic acid (RNA), and peptide nucleic acid (PNA). The genetic material can be made by synthetic chemical methodology known to one of ordinary skill in the art, or by the use of recombinant technology, or by a combination of the two. The DNA and RNA can optionally comprise unnatural nucleotides and can be single or double stranded. "Genetic material" refers also to sense and anti-sense DNA and RNA, that is, a nucleotide sequence that is complementary to a specific sequence of nucleotides in DNA and/or RNA.

As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight of less than 5000 Daltons (5 kD), preferably less than 3 kD, still more preferably less than 2 kD, and most preferably less than 1 kD. In some embodiments, a small molecule can have a molecular weight equal to or less than 700 Daltons. In some embodiments, a small molecule can have a molecular weight equal to or less than 500 Daltons As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. Patient or subject includes any subset of the foregoing, e.g., all of the above, but excluding one or more groups or species such as humans, primates or rodents. In certain embodiments, the subject is a mammal, e.g., a primate, e.g., a human. The terms, "patient" and "subject" are used interchangeably herein. In some embodiments, the subject or the patient is human. In some embodiments, subject is need of treatment for cancer.

Unless otherwise defined, e.g., as above, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety, unless noted otherwise. In case of conflict, the present specification, including definitions, will control. In addition, the materials, methods, and examples are illustrative only and not intended to be limiting.

Standard techniques can be used for chemical syntheses, chemical analyses, pharmaceutical preparation, formulation and delivery, and treatment of subjects. Reactions and purification techniques can be performed, e.g., using kits according to manufacturer's specifications or as commonly accomplished in the art or as described herein. The foregoing techniques and procedures generally are performed according to conventional methods well known in the art and as described in various general and more specific references that are cited and discussed throughout the present specification. See e.g., Sambrook et al., Molecular Cloning: A Laboratory Manual (2d ed., Cold Spring Harbor Laboratory Press, Cold Spring Harbor, N.Y. (1989).

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated may be further modified to incorporate features shown in any of the other embodiments disclosed herein.

The disclosure is further illustrated by the following examples which should not be construed as limiting. The examples are illustrative only, and are not intended to limit, in any manner, any of the aspects described herein. The following examples do not in any way limit the invention.

EXAMPLES

Example 1: Synthesis of (5-methyl-2-(2,4,6-trimethoxyphenyl)-1,3-dioxan-5-yl)methanol

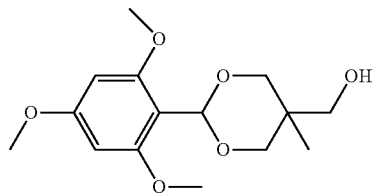 [SMILES: COc1cc(OC)c(C2OCC(C)(CO)CO2)c(OC)c1]

The synthesis of this precursor compound (1) follows a modification of a previously reported method (Gillies et al., J Am Chem Soc 126:11936-43, 2004). First, 1,1,1-tris (hydroxymethyl)ethane (5.5115 g) and 2,4,6-trimethoxybenzaldehyde (3 g) were dissolved in tetrahydrofuran, and 5 Å molecular sieves (45 g) were added as a desiccant. A catalytic amount of sulfuric acid was then added to the mixture, and the reaction vessel was shaken at room temperature overnight. When the reaction was complete, triethylamine (6 mL) was added to quench the acid. The molecular sieves were then removed using filtration. The solvent was removed via rotary evaporation under reduced pressure, and the residue dissolved in dichloromethane. This mixture was then washed three times with 100 mM pH 8.0 Tris buffer and dried over anhydrous sodium sulfate. The solvent was subsequently removed using rotary evaporation under reduced pressure, and the residue was purified using silica gel chromatography at 80% yield.

Example 2. Synthesis of (5-methyl-2-(2,4,6-trimethoxyphenyl)-1,3-dioxan-5-yl)methyl Methacrylate

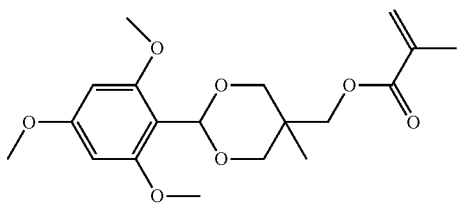 [SMILES: C=C(C)C(=O)OCC1(C)COC(c2c(OC)cc(OC)cc2OC)OC1]

The product of Example 1 (1.5 g) and triethylamine (1.527 g) were dissolved in dichloromethane and chilled to 0° C. Methacryloyl chloride (1.08 mL) was then added drop wise to the mixture under nitrogen atmosphere. After mixing overnight, methanol (1 mL) was added to quench the acid and the mixture was then washed three times with 100 mM pH 8.0 Tris buffer and dried over anhydrous sodium sulfate. The solvent was subsequently removed using rotary evaporation under reduced pressure and the residue, i.e. the title compound, was isolated using silica gel chromatography at 71% yield.

Example 3: Synthesis of 1,4-phenylene bis(2-methylacrylate)

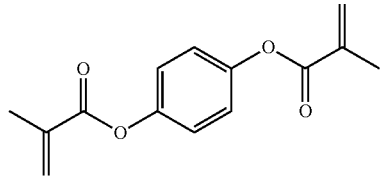 [SMILES: C=C(C)C(=O)Oc1ccc(OC(=O)C(=C)C)cc1]

Hydroquinone (1.0 g) and triethylamine (4.68 mL) were dissolved in dichloromethane and chilled to 0° C. Methacryloyl chloride (3.28 mL) was then added drop wise to the mixture under nitrogen atmosphere. After mixing overnight, methanol (1 mL) was added to quench the acid and the mixture was then washed three times with 100 mM pH 8.0 Tris buffer, washed once with Brine and dried over anhydrous sodium sulfate. The solvent was subsequently removed using rotary evaporation under reduced pressure and the residue, i.e. the title compound, was isolated using silica gel chromatography at 99% yield.

Example 4: Synthesis of (5-methyl-2-phenyl-1,3-dioxan-5-yl)methanol

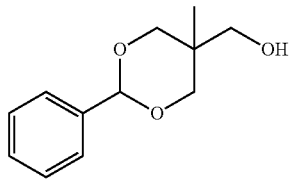

1,1,1-Tris(hydroxymethyl)ethane (2.61 g) and p-toluenesulfonic acid (0.339 g) were dissolved in benzaldehyde (2.8 mL) and stirred at 45° C. for 1 h. At this time, toluene (1.0 mL) was added to the solution, and toluene/water was distilled out of the mixture at 95° C. Fresh toluene was added, and distillation was carried out again. This process was repeated until no water was observed in the distillate. Sodium bicarbonate was added to quench the acid, and excess sodium bicarbonate was removed using filtration. The remaining toluene was removed via rotary evaporation, leaving a slightly yellow oil. This mixture was then purified using silica gel chromatography. The product was obtained as a white solid at 42% yield.

Example 5: Synthesis of (5-methyl-2-phenyl-1,3-dioxan-5-yl)methyl Methacrylate

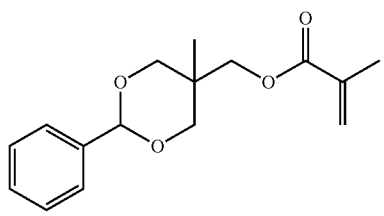 [SMILES: C=C(C)C(=O)OCC1(C)COC(c2ccccc2)OC1]

The product of Example 4 (0.504 g) and triethylamine (0.68 mL) were dissolved in dichloromethane and chilled to 0° C. Methacryloyl chloride (0.35 mL) was then added drop wise to the mixture under nitrogen atmosphere. After mixing overnight, the mixture was then washed with 100 mM pH 8.0 phosphate buffer and dried over anhydrous sodium sulfate. The solvent was subsequently removed using rotary evaporation under reduced pressure, and the product was isolated using silica gel chromatography at 84% yield.

Example 6: Synthesis of 1,3-bis(benzyloxy)propan-2-yl Methacrylate

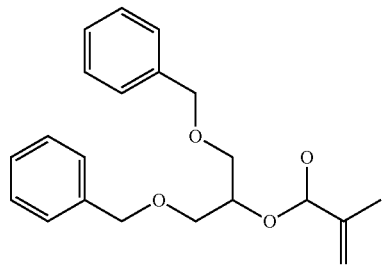 [SMILES: C=C(C)C(O)OC(COCc1ccccc1)COCc1ccccc1]

1,3-bis(benzyloxy)propan-2-ol (0.50 g) and triethylamine (0.52 mL) were dissolved in dichloromethane and chilled to 0° C. Methacryloyl chloride (0.27 mL) was then added drop wise to the mixture under nitrogen atmosphere. After mixing for overnight, the mixture was then washed with 100 mM pH 8.0 phosphate buffer and dried over anhydrous sodium sulfate. The solvent was subsequently removed using rotary evaporation under reduced pressure, and the product was isolated using silica gel chromatography at 81% yield.

Example 7: Synthesis of Benzyl Methacrylate

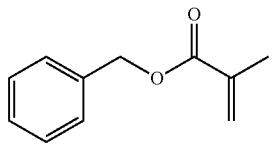

Phenylmethanol (1.0 g) and triethylamine (2.79 mL) were dissolved in dichloromethane and chilled to 0° C. Methacryloyl chloride (2.12 mL) was then added drop wise to the mixture under nitrogen atmosphere. After mixing for overnight, the mixture was then washed with 100 mM pH 8.0 phosphate buffer and dried over anhydrous sodium sulfate. The solvent was subsequently removed using rotary evaporation under reduced pressure, and the product was isolated using silica gel chromatography at 50% yield.

Example 8: Synthesis of (3aR,5R,6S,6aR)-5-((S)-2, 2-dimethyl-1,3-dioxolan-4-yl)-2,2-dimethyltetrahydrofuro[2,3-d][1,3]dioxol-6-yl Methacrylate

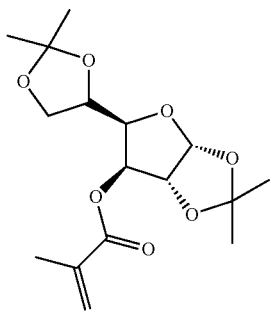

The synthesis of this compound was carried out as described by Black et al. and is described briefly. (Black et al., Journal of the Chemical Society 4433-4439, 1963). 1,2:5,6-di-O-isopropylidene-α-D-glucofuranose (1.00 g) and methacrylic anhydride (1.2 mL) were dissolved in pyridine (5 mL) and stirred at 65° C. for 3.5 h. Water (2.5 mL) was then added and stirring at 65° C. was continued for another 1.5 h and at room temperature overnight. The mixture was extracted with hexanes (5 mL×3), and the combined hexanes extracts were then washed with 1 M NaOH (15 mL×3) and deionized water (15 mL), followed by drying over $Na_2SO_4$. The solvent was removed using rotary evaporation under reduce pressure, and the remaining compound was dried under high vacuum. The product was obtained as a clear oil at 74% yield.

Example 9: Synthesis of Unloaded-Nanoparticles Using APS/TEMED

The monomer from Example 1 (100 mg) and crosslinker from Example 3 (1 mg, 1% wt/wt) were dissolved in dichloromethane (DCM) (920 μL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 μL) and tetramethylethylenediamine (TEMED) (4 μL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 10: Synthesis of Unloaded-Nanoparticles Using AIBN

Nanoparticles were prepared using a modification of a miniemulsion polymerization method previously reported (Landfester et al., Macromolecules 32:5222-8, 1999). Briefly, the monomer from Example 1 (100 mg), crosslinker from Example 3 (1 mg, 1% wt/wt), and free-radical initiator 2,2'-azobis(2-methlpropionitrile) (AIBN), were dissolved in dichloromethane (DCM) (920 μL), followed by removal of the solvent via rotary evaporation until a viscous mixture remained. The viscous oil was then mixed with a solution of sodium dodecyl sulfate (10 mg, 10% wt/wt), the stabilizing surfactant dissolved in 10 mM pH 7.4 phosphate buffer (4 mL). The mixture was sonicated for 30 min (1 s pulses with a 2 s delay) with 30 W of power under an argon blanket, forming a miniemulsion. Following sonication, the miniemulsion was transferred into a temperature-controlled oil bath and stirred at 65° C. for 2 hr under nitrogen atmosphere to initiate the free-radical polymerization. The solution was then stirred overnight under atmosphere to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 11: Synthesis of Unloaded-Nanoparticles Using Photoinitiation

The monomer from Example 1 (100 mg) and crosslinker from Example 3 (1 mg, 1% wt/wt) were dissolved in dichloromethane (DCM) (920 μL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 0.2 mM Eosin Y and 2 mM 1-vinyl-2-pyrrolidone were added to the emulsion. This mixture was then exposed to light from a xenon lamp operating at 300 W for 10 min while being stirred vigorously, causing polymerization. Following photopolymerization, the particles were stirred overnight while open to the air to allow any remaining DCM to evaporate. The resulting polymeric nanoparticles were dialyzed against 5 mM pH 7.4 phosphate buffer (1 L) for 24 hr to remove excess surfactant and salts; the buffer was exchanged once after 8 hr.

Example 12: Synthesis of Paclitaxel Loaded-Nanoparticles Using APS/TEMED

The monomer from Example 1 (100 mg), crosslinker from Example 3 (1 mg, 1% wt/wt), and Paclitaxel (1 mg, 1% wt/wt) were dissolved in dichloromethane (DCM) (920 μL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 μL) and tetramethylethylenediamine (TEMED) (4 μL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 13: Synthesis of Paclitaxel Loaded-Nanoparticles Using AIBN

Nanoparticles were prepared using a modification of a miniemulsion polymerization method previously reported (Landfester et al., Macromolecules 32:5222-8, 1999). Briefly, the monomer from Example 1 (100 mg), crosslinker from Example 3 (1 mg, 1% wt/wt), Paclitaxel (1 mg, 1% wt/wt), and free-radical initiator 2,2'-azobis(2-methlpropionitrile) (AIBN), were dissolved in dichloromethane (DCM) (920 µL), followed by removal of the solvent via rotary evaporation until a viscous mixture remained. The viscous oil was then mixed with a solution of sodium dodecyl sulfate (10 mg, 10% wt/wt), the stabilizing surfactant dissolved in 10 mM pH 7.4 phosphate buffer (4 mL). The mixture was sonicated for 30 min (1 s pulses with a 2 s delay) with 30 W of power under an argon blanket, forming a miniemulsion. Following sonication, the miniemulsion was transferred into a temperature-controlled oil bath and stirred at 65° C. for 2 hr under nitrogen atmosphere to initiate the free-radical polymerization. The solution was then stirred overnight under atmosphere to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 14: Synthesis of Paclitaxel Loaded-Nanoparticles Using Photoinitiation

The monomer from Example 1 (100 mg), crosslinker from Example 3 (1 mg, 1% wt/wt), and Paclitaxel (1 mg, 1% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 0.2 mM Eosin Y and 2 mM 1-vinyl-2-pyrrolidone were added to the emulsion. This mixture was then exposed to light from a xenon lamp operating at 300 W for 10 min while being stirred vigorously, causing polymerization. Following photopolymerization, the particles were stirred overnight while open to the air to allow any remaining DCM to evaporate. The resulting polymeric nanoparticles were dialyzed against 5 mM pH 7.4 phosphate buffer (1 L) for 24 hr to remove excess surfactant and salts; the buffer was exchanged once after 8 hr.

Example 15: Synthesis of Fluorescently Labeled-Nanoparticles Using APS/TEMED

The monomer from Example 1 (100 mg), crosslinker from Example 3 (1 mg, 1% wt/wt), and a fluorophore (either methacryloxyethyl thiocarbamoyl rhodamine B or 9-anthracenylmethyl methacrylate 0.2 mg, 0.2% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 16: Synthesis of Fluorescently Labeled-Nanoparticles Using AIBN

Nanoparticles were prepared using a modification of a miniemulsion polymerization method previously reported (Landfester et al., Macromolecules 32:5222-8, 1999). Briefly, the monomer from Example 1 (100 mg), crosslinker from Example 3 (1 mg, 1% wt/wt), a fluorophore (either methacryloxyethyl thiocarbamoyl rhodamine B or 9-anthracenylmethyl methacrylate 0.2 mg, 0.2% wt/wt), and free-radical initiator 2,2'-azobis(2-methlpropionitrile) (AIBN), were dissolved in dichloromethane (DCM) (920 µL), followed by removal of the solvent via rotary evaporation until a viscous mixture remained. The viscous oil was then mixed with a solution of sodium dodecyl sulfate (10 mg, 10% wt/wt), the stabilizing surfactant dissolved in 10 mM pH 7.4 phosphate buffer (4 mL). The mixture was sonicated for 30 min (1 s pulses with a 2 s delay) with 30 W of power under an argon blanket, forming a miniemulsion. Following sonication, the miniemulsion was transferred into a temperature-controlled oil bath and stirred at 65° C. for 2 hr under nitrogen atmosphere to initiate the free-radical polymerization. The solution was then stirred overnight under atmosphere to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 17: Synthesis of Fluorescently Labeled Paclitaxel Loaded-Nanoparticles Using APS/TEMED The monomer from Example 1 (100 mg), crosslinker from Example 3 (1 mg, 1% wt/wt), Paclitaxel (1 mg, 1% wt/wt), and a fluorophore (either methacryloxyethyl thiocarbamoyl rhodamine B or 9-anthracenylmethyl methacrylate 0.2 mg, 0.2% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 18: Synthesis of Fluorescently Labeled Paclitaxel Loaded-Nanoparticles Using AIBN Nanoparticles were prepared using a modification of a miniemulsion polymerization method previously reported (Landfester et al., Macromolecules 32:5222-8, 1999). Briefly, the monomer from Example 1 (100 mg), crosslinker from Example 3 (1 mg, 1% wt/wt), Paclitaxel (1 mg, 1% wt/wt), a fluorophore (either methacryloxyethyl thiocarbamoyl rhodamine B or 9-anthracenylmethyl methacrylate 0.2 mg, 0.2% wt/wt), and free-radical initiator 2,2'-azobis(2-methlpropionitrile) (AIBN), were dissolved in dichloromethane (DCM) (920 µL), followed by removal of the solvent via rotary evaporation until a viscous mixture remained. The viscous oil was then mixed with a solution of sodium dodecyl sulfate (10 mg, 10% wt/wt), the stabilizing surfactant dissolved in 10 mM pH 7.4 phosphate buffer (4 mL). The mixture was sonicated for 30 min (1 s pulses with a 2 s delay) with 30 W of power under an argon blanket, forming a miniemulsion. Following sonication, the miniemulsion was transferred into a temperature-controlled oil bath and stirred at 65° C. for 2 hr under nitrogen atmosphere to initiate the free-radical polymerization. The solution was then stirred overnight under atmosphere to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 19: Synthesis of Pycnidione Loaded-Nanoparticles Using APS/TEMED

The monomer from Example 1 (100 mg), crosslinker from Example 3 (1 mg, 1% wt/wt), and Pycnidione (1 mg, 1% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 20: Synthesis of Pemetrexed Loaded-Nanoparticles Using APS/TEMED

The monomer from Example 1 (100 mg), crosslinker from Example 3 (1 mg, 1% wt/wt), and Pemetrexed (1 mg, 1% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 21: Synthesis of Iodine Doped Unloaded-Nanoparticles for TEM Imaging

The monomer from Example 1 (100 mg), crosslinker from Example 3 (1 mg, 1% wt/wt), and a tri-iodo co-monomer, 2-(3-acetamido-2,4,6-triiodobenzamido)ethyl methacrylate, (1 mg, 1% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 22: Synthesis of Unloaded-Nanoparticles with PEG-PPG-PEG Coating Using APS/TEMED The monomer from Example 1 (100 mg) and crosslinker from Example 3 (1 mg, 1% wt/wt) were dissolved in dichloromethane (DCM) (920 µL). The stabilizing surfactant, a tri-block copolymer PEG-PPG-PEG, Pluronic F-127 (50 mg, 50% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 23: Synthesis of Unloaded-Nanoparticles with PEG Coating Using APS/TEMED The monomer from Example 1 (100 mg) and crosslinker from Example 3 (1 mg, 1% wt/wt) were dissolved in dichloromethane (DCM) (920 µL). The stabilizing surfactant, sodium dodecyl sulfate (10 mg, 10% wt/wt), and 2,4,6,8,11,14,17-heptaoxanonadecan-19-yl methacrylate (25 mg, 25% wt/wt) was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 24: Synthesis of Unloaded-PLGA Nanoparticles

Nanoparticles were prepared using a modification of a miniemulsion polymerization method previously reported by Edlund & Albertsson and Wang et. al. (Edlund et al., Adv. Polymer Sci., 157:67-112, 2001; Wang et al., Chem. Pharm. Bull., (Tokyo) 44:1935, 1996)). First, 500 mg of 75:25 PLGA tablets were dissolved in 4 mL dichloromethane using a vortex. The solution was placed in 10 ml of 5% polyvinyl alcohol surfactant and vortexed for 15 minutes (or sonicated using a probe tip sonicator) and stirred overnight. The nanoparticles were collected and washed three times in 50 mL of distilled/deionized water.

Example 25: Synthesis of Paclitaxel Loaded-PLGA Nanoparticles

Nanoparticles were prepared using a modification of a miniemulsion polymerization method previously reported by Edlund & Albertsson and Wang et. al. (Edlund et al., Adv. Polymer Sci., 157:67-112, 2001; Wang et al., Chem. Pharm. Bull., (Tokyo) 44:1935, 1996)). First, 500 mg of 75:25 PLGA tablets (the greater the ratio of lactic acid to glycolic acid the slower the release) were dissolved in 4 mL dichloromethane using a vortex. After the plastic was completely dissolved, 50 mg of Paclitaxel previously solubilized in ~100 µl of dimethyl sulfoxide, was added and further vortexed. The solution was placed in 10 ml of 5% polyvinyl alcohol surfactant and vortexed for 15 minutes (or sonicated using a probe tip sonicator) and stirred overnight. The nanoparticles were collected and washed three times in 50 mL of distilled/deionized water. Following washing, the nanoparticles were lyophilized (freeze dried) and stored at −20° C. to insure the stability of Paclitaxel. The encapsulation efficiency of Paclitaxel was determined to be 74%+/− 4% by HPLC analysis.

Example 26: Synthesis of Non-Expansile-Nanoparticles (neNPs) Using APS/TEMED

The monomer from Example 5 (100 mg) and crosslinker from Example 3 (1 mg, 1% wt/wt) were dissolved in dichloromethane (DCM) (920 µL). The stabilizing surfactant, sodium dodecyl sulfate (10 mg, 10% wt/wt), was dissolved in 10 mM pH 7.4 phosphate buffer (4 mL). The organic and aqueous phases were mixed and sonicated for 30 min (1 s pulses with a 2 s delay) with 30 W of power under an argon blanket, forming a miniemulsion. Following sonication, 200 mM ammonium peroxydisulfate (APS) (40 µL) and tetramethylethylenediamine (TEMED) (4 µL) were added to the emulsion. This mixture was stirred under an argon atmosphere for 2 hr to allow for polymerization and then overnight while open to the air to allow for evaporation of any remaining DCM. The resulting polymeric nanoparticles were dialyzed against 5 mM pH 7.4 phosphate buffer (1 L) for 24 hr to remove excess surfactant and salts; the buffer was exchanged once after 8 hr.

Example 27: Scanning Electron Microscope Characterization of Nanoparticles

Samples for scanning electron microscope (SEM) imaging were prepared by diluting a sample of nanoparticles to a concentration of 0.25 mg/mL with deionized water. A 10 µL portion of the diluted sample was then placed on a silicon wafer, which was attached to a clean aluminum stub using copper tape and allowed to air dry. Prior to imaging, the samples were coated with a 5 nm layer of Au/Pd. Samples were then imaged on a Zeiss SUPRA 55VP field emission SEM using an accelerating voltage of 1 or 5 kV. Nanoparticles ranging in size from 1 nm to 200 nm were observed (FIG. 1)

Figure 2:
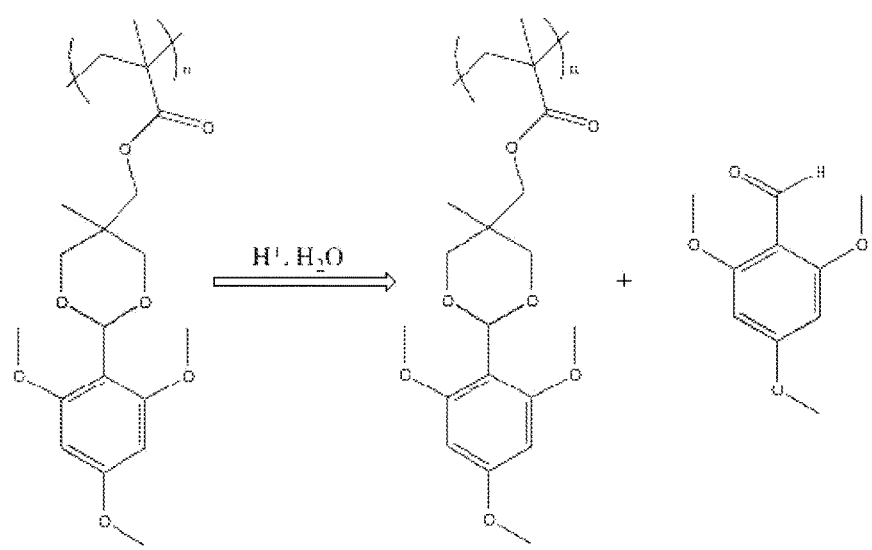
FIG. 2 is a schematic representation of the chemical reaction leading to the deprotection of individual monomer units within the nanoparticle polymer and subsequent change from a more hydrophobic to a less hydrophobic structure with loss of the trimethoxy benzaldehyde protecting group. The trimethoxy benzaldehyde protecting group absorbs at 292 nm.
Figure 3:
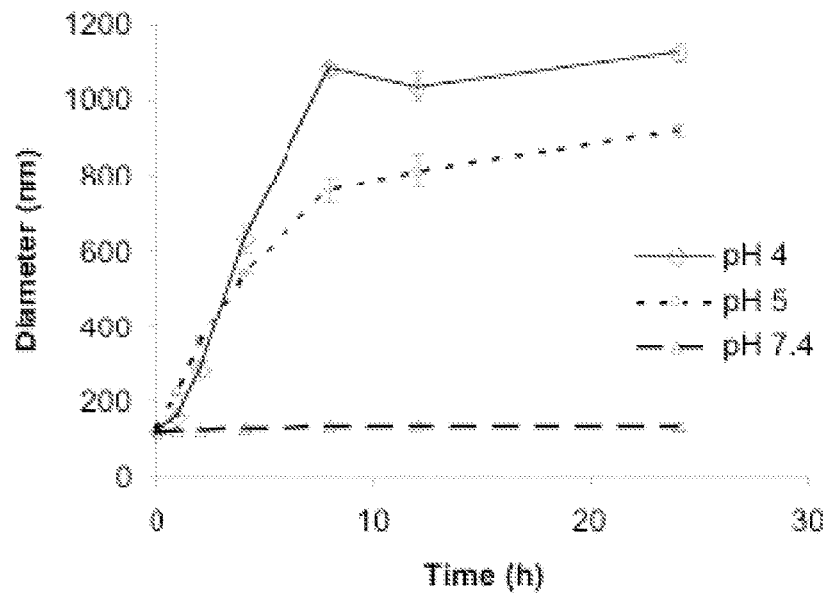
FIG. 3 is a line graph showing particle diameter as a function of time at various pHs. As can be seen, particles maintained at pH 4 and 5 swell to ~10× their original diameter while those maintained at pH 7.4 do not swell.
Figure 4:
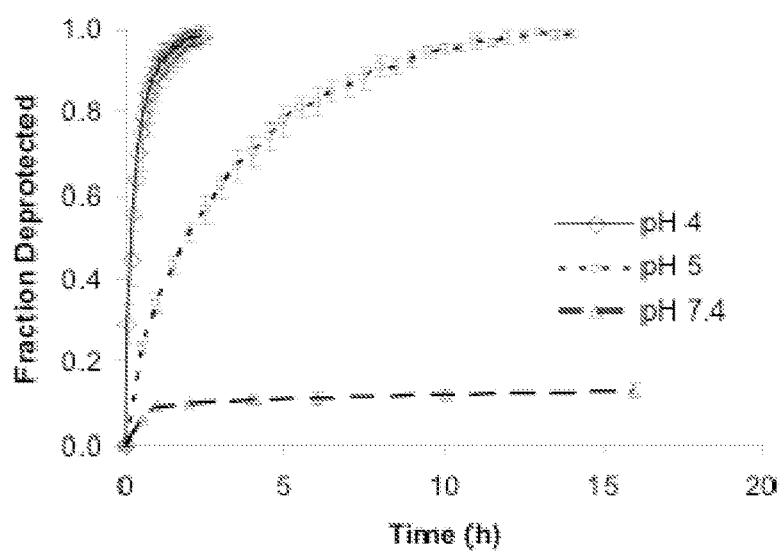
FIG. 4 is a line graph showing deprotection observed by absorbance using UV/Vis spectroscopy at wavelength of 292 nm.

Example 28: Nanoparticle Swelling Measured Using Dynamic Light Scattering (DLS) and UV/Vis Spectroscopy As schematically shown in FIG. 2, nanoparticles can swell under acidic but not neutral conditions. A sample of the nanoparticles was diluted in buffer at a pH 4, 5, or 7.4 and maintained at 37° C. The diameter of the particles was then measured at regular time intervals using dynamic light scattering (DLS), showing how the particles increased in size over time. Prior to each DLS measurement, the samples were sonicated for 5 s to break up aggregates. Particle swelling from 100 nm in diameter to near 1 µm in diameter was observed (FIG. 3). In addition, the release of free 2,4,6-trimethoxybenzaldehyde was observed using UV/Vis spectroscopy at a wavelength of 292 nm (FIG. 4).

Example 29: Nanoparticle Swelling Measured Using Light Microscopy

Figure 5:
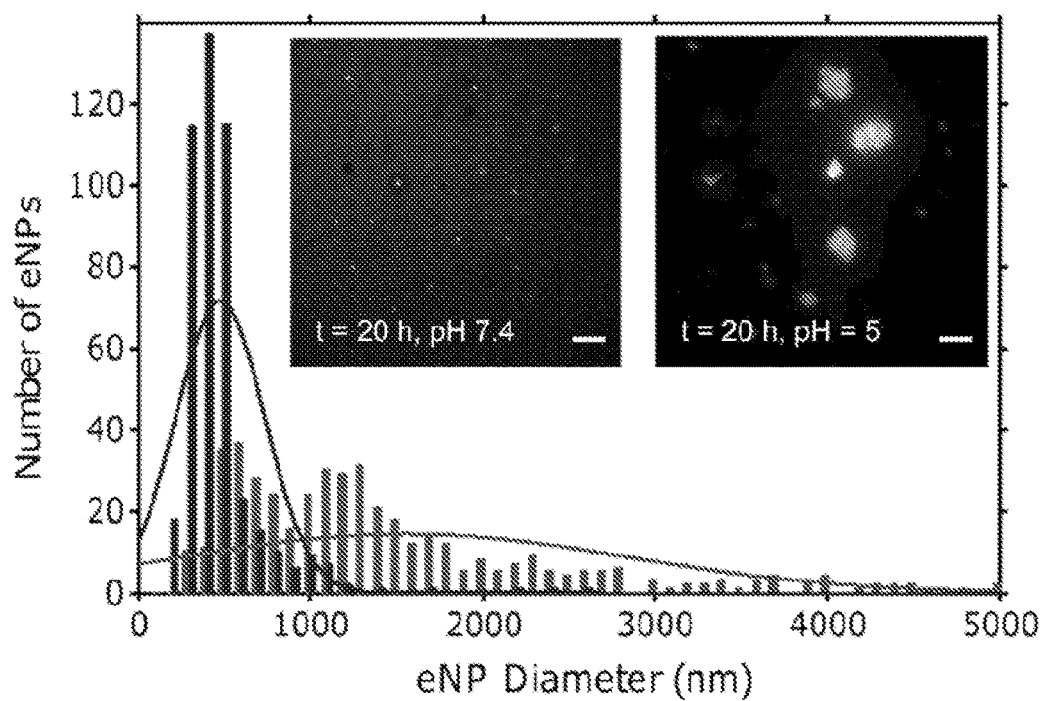
FIG. 5 is a histogram showing distribution of eNP sizes at pH 7.4 (blue) and pH 5 (red). Insert—photographs of eNP at pH 7.4 and pH 5. Scale bar=5 µm.

To optically observe and characterize individual particles, we prepared nanoparticles of ≈450 nm in diameter containing a fluorescent tag. Specifically, a rhodamine co-monomer was used to covalently attach the fluorescent tag to the polymer backbone of the nanoparticles as in Example 15. The nanoparticles were diluted in buffer at pH 7.4 or 5, and, after 20 hours, viewed under a Zeiss 200M inverted microscope with fluorescence epi-illumination from a Coherent Sapphire solid-state 488-nm laser for counting and diameter determination using a 100×/1.40 NA oil immersion objective. Semrock long-pass filters were used to eliminate scattered light from the laser illumination and an Andor iXon 897 back-illuminated Electron-Multiplying CCD camera was used to record the images. The histogram in FIG. 5, shows that eNPs at neutral pH are, on average, 479±257 nm in diameter whereas after 20 hours at pH 5 diameters are 1556±1274 nm, with the distribution of diameters ranging from several hundred to several thousand nanometers (FIG. 5). The difference between the two populations is statistically significant with a $p<0.001$.

Example 30: Nanoparticle Swelling Measured Using Scanning Electron Microscopy (SEM)

Figure 6:
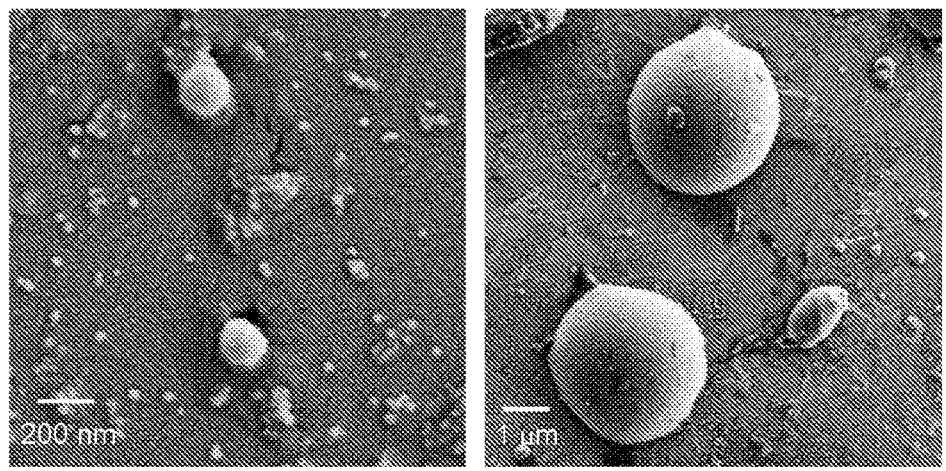
FIG. 6 shows SEM images of expansile nanoparticles maintained at pH 7.4 (left) and pH 5 (right) for 72 hr._Particles maintained at pH 5 are ~10× larger in diameter than those maintained at pH 7.4.

Samples were prepared for imaging by diluting an aliquot of eNPs in pH 5 or 7.4 buffer and incubating them for up to 72 hours. Particles kept at neutral pH range from ≈20 to 200 nm in diameter whereas those exposed to an acidic pH of 5 are roughly a micron or more in diameter. Particles maintained at pH 5 were ~10× larger in diameter than those maintained at pH 7.4 (FIG. 6)

Example 31: Nanoparticle Swelling Measured Using Transmission Electron Microscopy (TEM)

Figure 7:
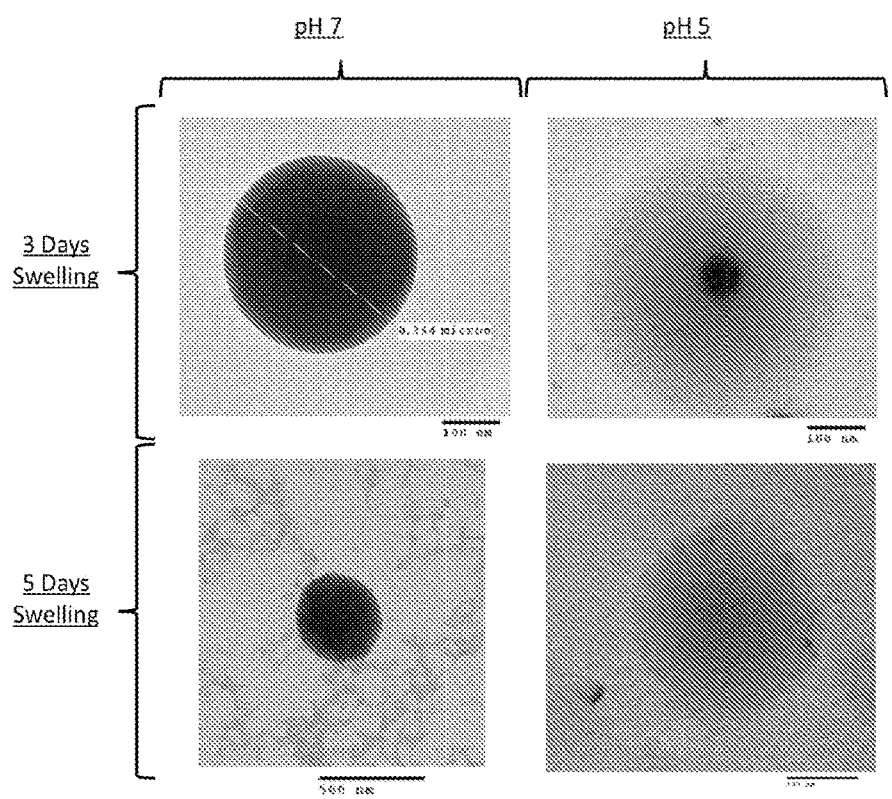
FIG. 7 shows TEM images of expansile nanoparticles maintained at pH 7.4 (left) and pH 5 (right) for 3 days (top) and 5 days (bottom). Particles maintained at pH 5 have a diffuse core and edge as compared to those maintained at pH 7.4.

Nanoparticles prepared as in Example 21 were maintained at pH 5 or pH 7.4 at 37° C. for 3 and 5 days. Samples were diluted 10× into de-ionized water containing 0.1% Triton X-100 and adsorbed onto imaging grids. TEM imaging revealed uniform dense, spherical structures at pH 7.4 at both time points. After 3 days of swelling at pH 5, the structures became larger with a dense core and diffuse corona within a distinct spherical boundary. After 5 days of swelling, these structures lost their distinct boundary and dense core becoming a diffuse roughly spherical structure (FIG. 7).

Example 32: Nanoparticle Swelling Measured Using Freeze Fracture-Transmission Electron Microscopy (ff-TEM)

Figure 8:
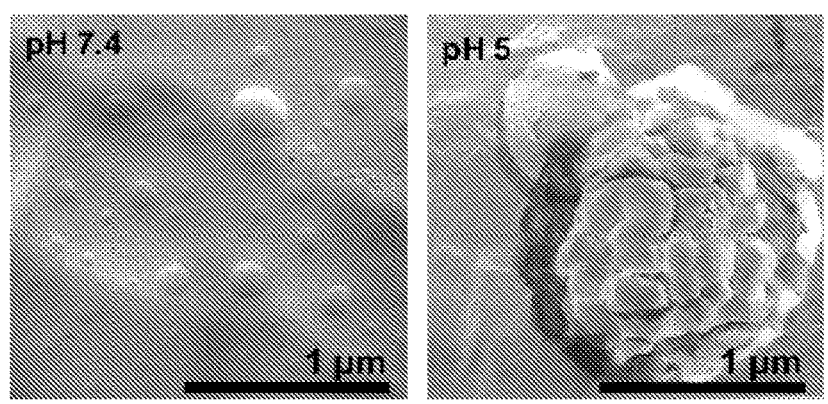
FIG. 8 shows freeze fracture-TEM images of eNPs after exposure to pH 7.4 (left) and pH 5 (right) solutions.

Freeze-fracture TEM was used to examine nanoparticle swelling; this technique was chosen as it enables one to capture and replicate the state of the non-expanded and expanded nanoparticles in solution. Samples were prepared for imaging by diluting an aliquot of eNPs in pH 5 or 7.4 buffer and incubating them at 37° C. for 24 hours. The samples were flash frozen using liquid-nitrogen cooled in propane and fractured along a plane. The fracture planes were shadowed with platinum and carbon to replicate the planes' surfaces. The replicas were then imaged using TEM. Images of the sample are shown in FIG. 8. The eNPs maintained at pH 7.4 appeared as spherical≈50 to 200 nm structures, while the eNPs maintained at pH 5 appeared as larger irregular structures≈1 μm in diameter. Additionally, the pH 5 samples noticeably lacked smaller 100 nm particles.

Example 33: Nanoparticle Swelling Measured Using qNano Nanopore Technology

Figure 9:
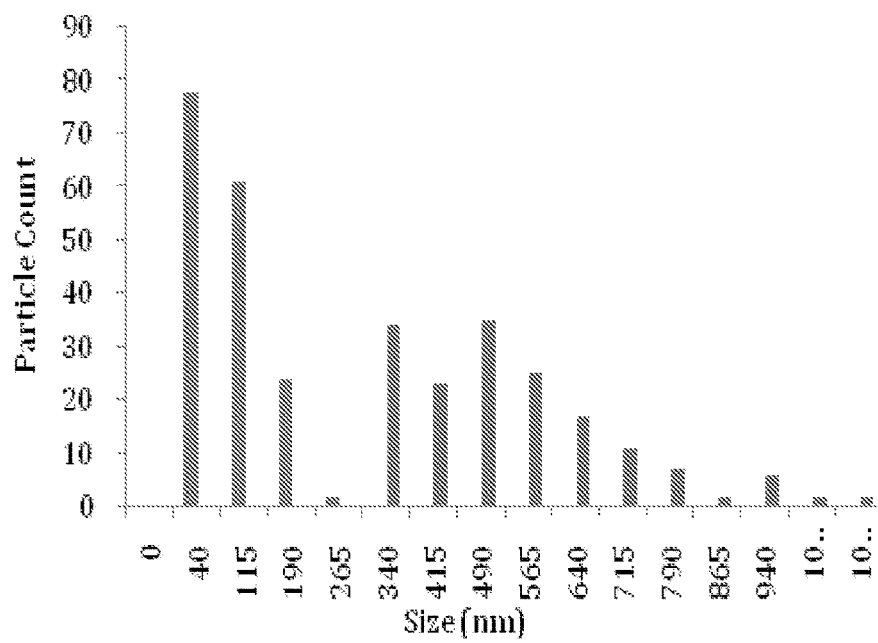
FIG. 9 is a bar graph showing expansile nanoparticles maintained at pH 7.4 (blue) and pH 5 (red) for 72 hr. Particles maintained at pH 5 are ~6× larger in diameter than those maintained at pH 7.4

Samples were prepared for imaging by diluting an aliquot of eNPs in pH 5 or 7.4 buffer and incubating them for up to 72 hours. Measurement of particle diameter using qNano nanopore technology from Izon Ltd. showed that particles kept at neutral pH range from 20 to 200 nm in diameter whereas those exposed to an acidic pH of 5 range from 300 nm to over a 1 μm in diameter (FIG. 9).

Figure 10:
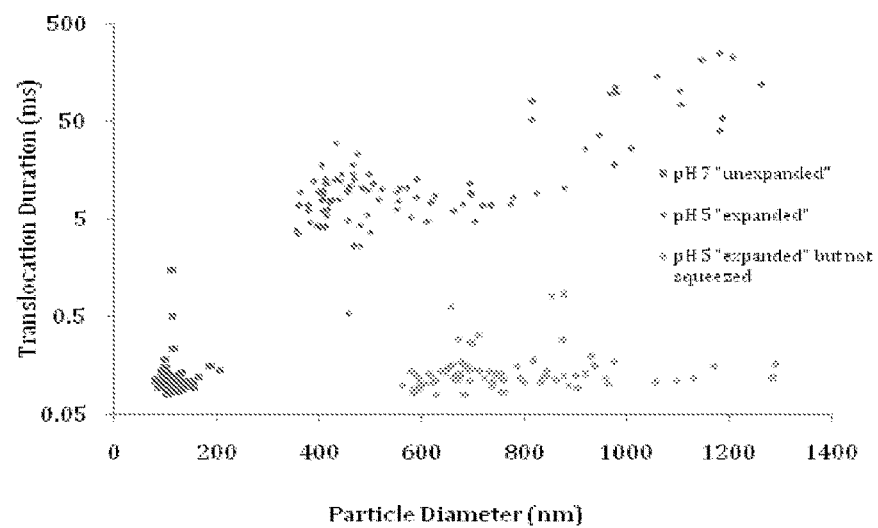
FIG. 10 is dot plot showing gating of expansile nanoparticles using qNano nanopore technology. Particles maintained at pH 7.4 (blue) for 72 hr easily pass through the nanopore; particles maintained at pH 5 (green) also pass easily through a larger nanopore; particles maintained at pH 5 (red) can be squeezed through a smaller nanopore than is used to measure the green particles and thus exhibit a longer time to translocate the pore.

Further analysis of the swollen and unswollen particles was performed by using the nanopore to "gate" particles (FIG. 10). When a large enough pore opening is used, unswollen particles (average diameter 115±21 nm) maintained at pH 7.4 pass easily through the pore with an average time to traverse the pore of 0.13±0.17 ms; if the pore is too small, particles do not pass through and are not counted. Similarly, when a large enough pore opening is used, swollen particles (average diameter 766±162 nm) maintained at pH 5 pass easily through the pore with an average time to traverse the pore of 0.15±0.13 ms. However, when the size of the nanopore is decreased, swollen particles can still pass through the pore for by deforming and squeezing through the smaller opening. This deformation of the softer, swollen (average diameter 615±250 nm) particle is reflected in a longer time required to traverse the pore at 26.4±47.8 ms.

Example 34: Measurement of Nanoparticle Swelling of a Sugar Analog Using Dynamic Light Scattering (DLS)

Figure 11:
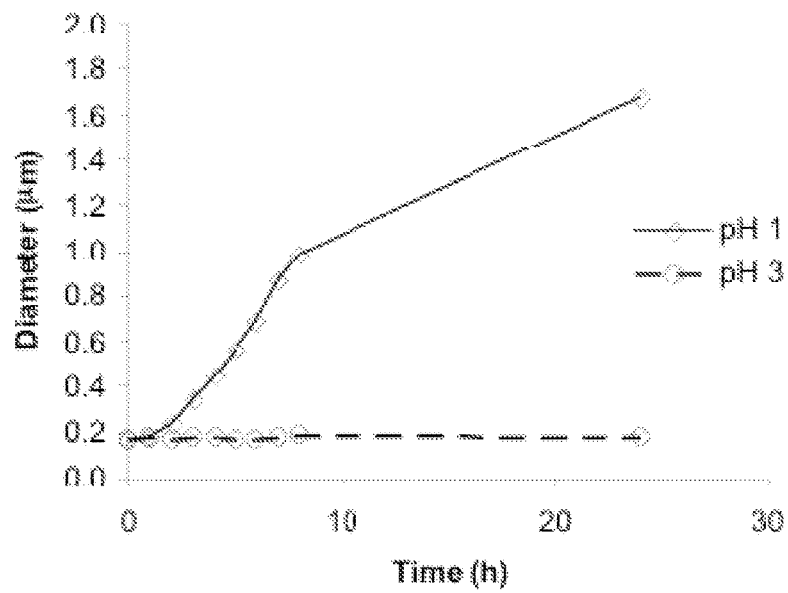
FIG. 11 is a line graph showing diameter of sugar derived nanoparticles maintained at pH 1 and pH 3 over a time course of 24 hr.

Nanoparticles as prepared in Example 8 were diluted in 0.1 M HCl and maintained at 25° C. The diameter of the particles was then measured at regular time intervals using dynamic light scattering (DLS), showing how the particles increased in size over time. FIG. 11 shows the diameter of sugar derived nanoparticles maintained at pH 1 and pH 3 over a time course of 24 hr.

Example 35: Paclitaxel Release from Nanoparticles into a Sink

Figure 12:
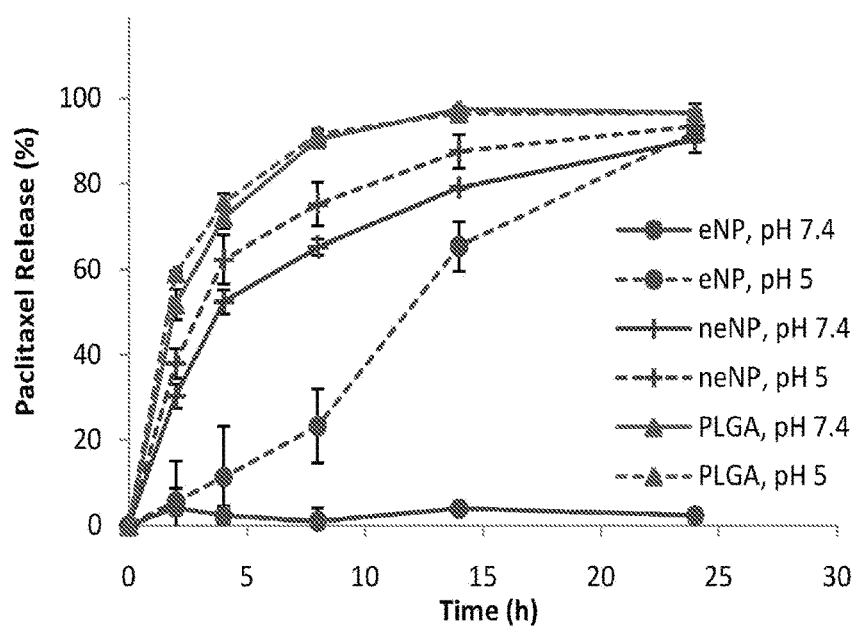
FIG. 12 is a line graph showing release of paclitaxel as a function of pH and time for expansile, non-expansile, and PLGA nanoparticles. Data displayed as mean±SD; n=3.

Paclitaxel was loaded intonanoparticlesas in Example 12 at a concentration of 1% wt/wt with 85% encapsulation efficiency as determined by HPLC. As shown in FIG. 12, the release of paclitaxel from the Pax-eNPs (filled circles, blue) was pH dependent and related to the hydrophobic to hydrophilic transformation. Minimal paclitaxel release by Pax-eNPs was observed at pH 7.4 whereas nearly 100% release occurred within 24 hr at pH 5. In contrast, Paclitaxel loaded-non-expansile nanoparticles as those made from the monomer in Example 5 (Pax-neNPs)(vertical lines, red) showed significant, rapid paclitaxel release at pH 7.4 within the first 5 hours, but the release was not correlated with the surrounding pH. We also evaluated traditional paclitaxel-loaded poly(lactide-co-glycolide) (Pax-PLGA) nanoparticles (filled triangles, green), since these nanoparticles are not a hydrogel and represent the prototypical non-expansile nanoparticle that many investigators use. As shown in FIG. 12, Paclitaxel release was observed from PLGA nanoparticles at both pH 7.4 and pH 5 with a rapid burst release of nearly 75% of the drug within 4 hours and 100% of the drug by 10 hours. This indicates that most of the drug is released, regardless of pH, from Pax-neNPs and Pax-PLGA-NPs.

Figure 13:
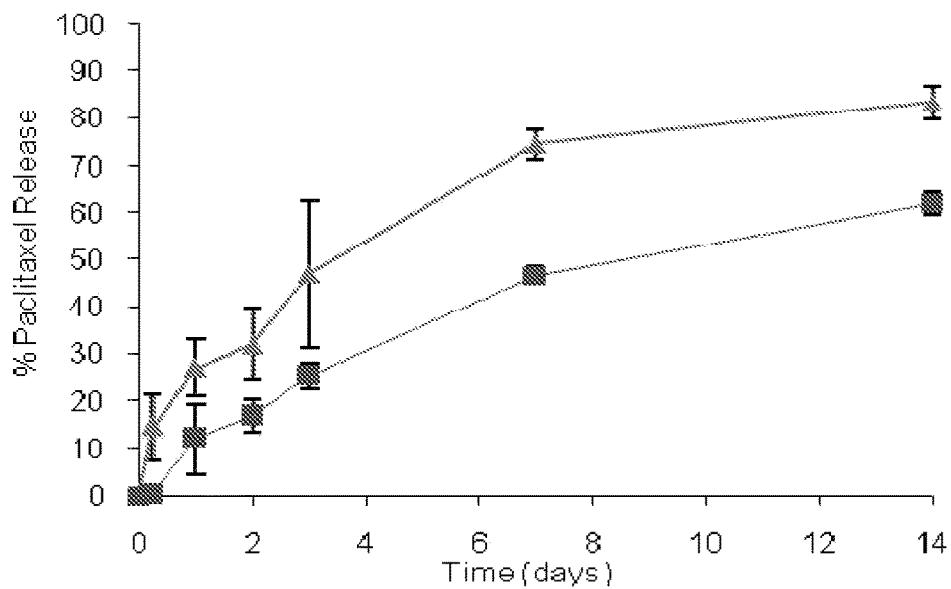
FIG. 13 is a line graph showing release of paclitaxel as a function of pH and time for expansile particles with 30% crosslinker wt/wt at pH 5 (triangle, red) and pH 7 (square, blue). Data displayed as mean±SD; n=3.

Example 36: Paclitaxel Release from Heavily Crosslinked Nanoparticles into a Sink Paclitaxel was loaded into nanoparticles similar to those in Example 12 but with 30% wt/wt crosslinker; Paclitaxel was loaded at a concentration of 5% wt/wt with 86% encapsulation efficiency as determined by HPLC. Paclitaxel loaded-nanoparticles were maintained at pH 7.5 and pH 5 for 14 days in an aqueous sink with 0.001%/wt SDS (10 mg in 1 L of sink). Paclitaxel concentration in the particles was measured via HPLC. Paclitaxel diffused out of the particles maintained at pH 5 at a faster rate than from those maintained at pH 7.4, but at a slower rate than seen in Example 35 due to the increased cross-linking and decreased swelling of the nanoparticles (FIG. 13) The non-zero release from particles at pH 7.4 is likely due to the SDS in the sink which enables the hydrophobic Paclitaxel to reside in the aqueous sink.

Example 37: In Vitro Efficacy of Nanoparticle Mediated Drug Delivery (Cell Culture)

Melanoma B16 (murine), Calu 6 (human lung carcinoma), A549 (human lung carcinoma), LLC (murine Lewis Lung Carcinoma), NCI-H460 (human lung), MSTO-211H (human mesothelioma), MSTO-211H-Luc (luciferase transfected human mesothelioma), MCF7 (human breast), LMS05 (human sarcoma) were incubated (37° C., 5% $CO_2$) with MEM (with 10% fetal bovine serum (FBS), 1% essential amino acids, and 1% Penicillin/Streptomyocin with L glutamine (Pen/Strep), F-12 HAM (with 10% FBS and 1% Pen/Strep), DMEM (with 10% FBS and 1% Pen/Strep) media, or DMEM (with 10% FBS and 1% GPS), with media changes once every three days. When not cultured, all cell lines were stored in RPMI freezing media at −80° C. (with 50% FBS, 40% RPMI and 10% dimethyl sulfoxide (DMSO)). Cell lines were trypsinized from the plates and seeded into 96 well plates at a concentration of 3000 cells per well. All cell lines were cultured for a period of at least seven days before being tested in cell uptake or proliferation assays etc.

Example 38: Nanoparticle Uptake by Cells

Figure 14A:
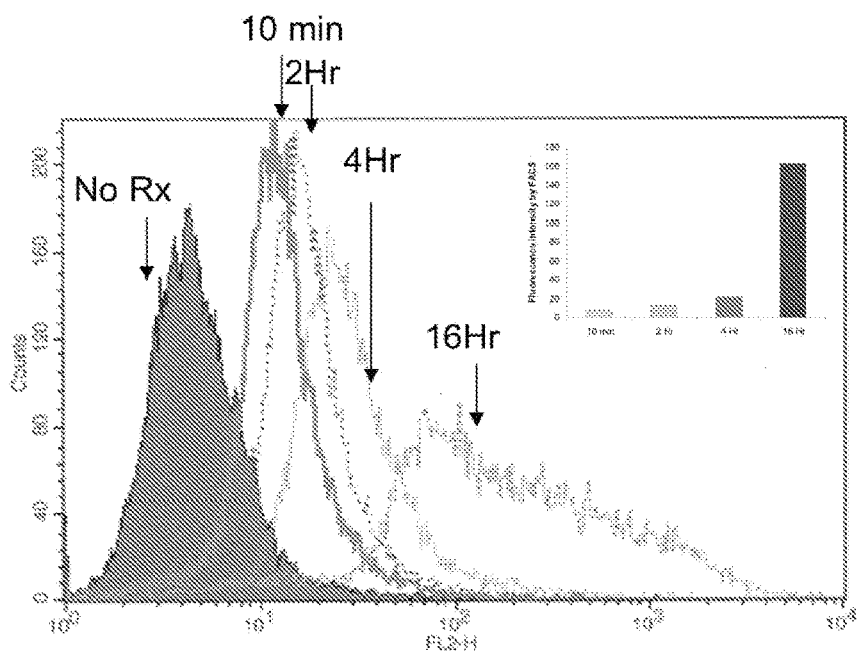
FIG. 14A shows quantification of eNP uptake by A549 lung cancer cells by flow cytometry. Insert shows the increased uptake of eNPs as a function of time.
Figure 14B:
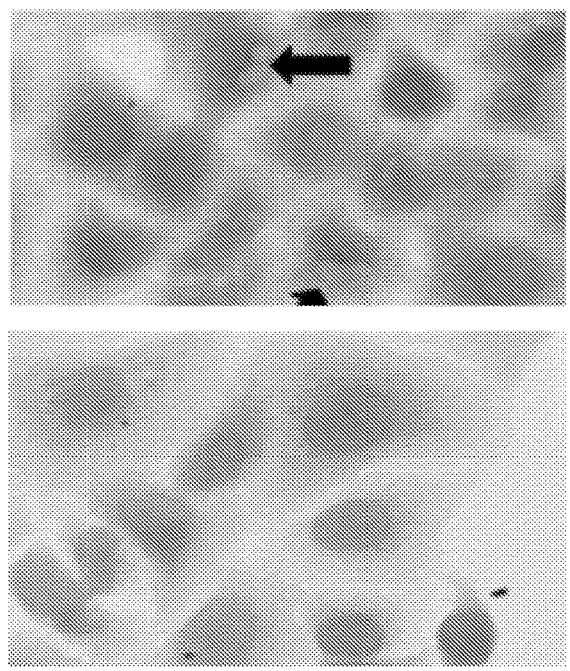
FIG. 14B shows direct visualization of the expanded NPs in A549 cells after 24 hours (40×). Cells were fixed and stained with H&E. Note accumulation of nanoparticles in the cytoplasm of many cells (upper panel; arrows). No such structures were seen in untreated control cells (lower panel).
Figure 14C:
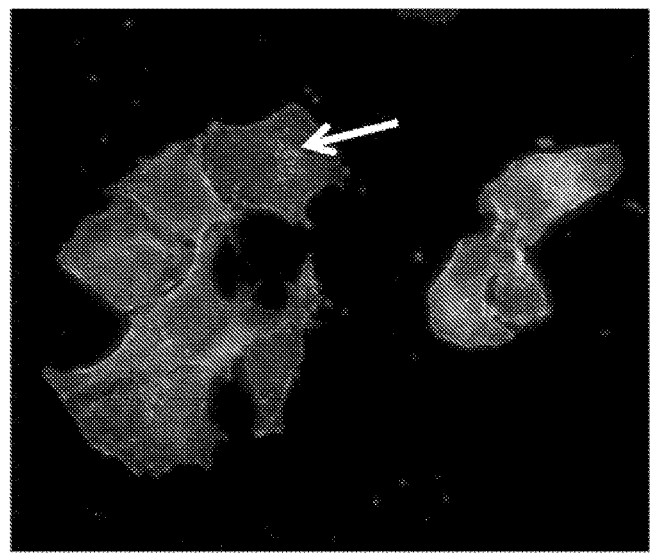
FIG. 14C shows the merged fluorescent image of A549 cells treated with rhodamine-eNPs (red) followed by staining for with phalloidin (green) and DAPI (blue) (40×).

Fluorescent nanoparticles were synthesized as in Example 15 using a Rhodamine B co-monomer. Non-small cell lung cancer A549 cells were seeded onto a 96-well plate (20,000 cells/well) and incubated overnight at 37° C. and 5% $CO_2$. The media was then removed from the wells and replaced with a buffered saline solution containing the rhodamine labeled-nanoparticles at a concentration of 0.5, 1, or 5 mg/mL. Controls not containing nanoparticles were also performed. After incubation at 37° C. and 5% carbon dioxide for 0.5, 1, 2, or 4 hours, the particle suspension was removed, and the cells were washed twice with buffered saline and then lysed with 100 μL of 0.5% Triton X-100 in 0.2 M sodium hydroxide. Measuring the fluorescence of the cell lysate samples (excitation wavelength=470 nm, emission wavelength=518 nm) and comparing to a standard curve gave the concentration of nanoparticles in the samples. The cells showed increased uptake of nanoparticles over time and increased uptake atlowernanoparticle concentrations. Alternatively confocal microscopy, histology or flow cyctometry can be used to document intracellular uptake of the fluorescently labeled nanoparticles. Similar results were obtained with these modalities as seen in FIGS. 14A-14C. These results have been also observed with LLC (murine Lewis Lung Carcinoma), MSTO-211H (human mesothelioma), and MDA-MB-231 (breast cancer cells).

Example 39: In Vitro Cell Uptake of Paclitaxel Loaded-Nanoparticles

Figure 15:
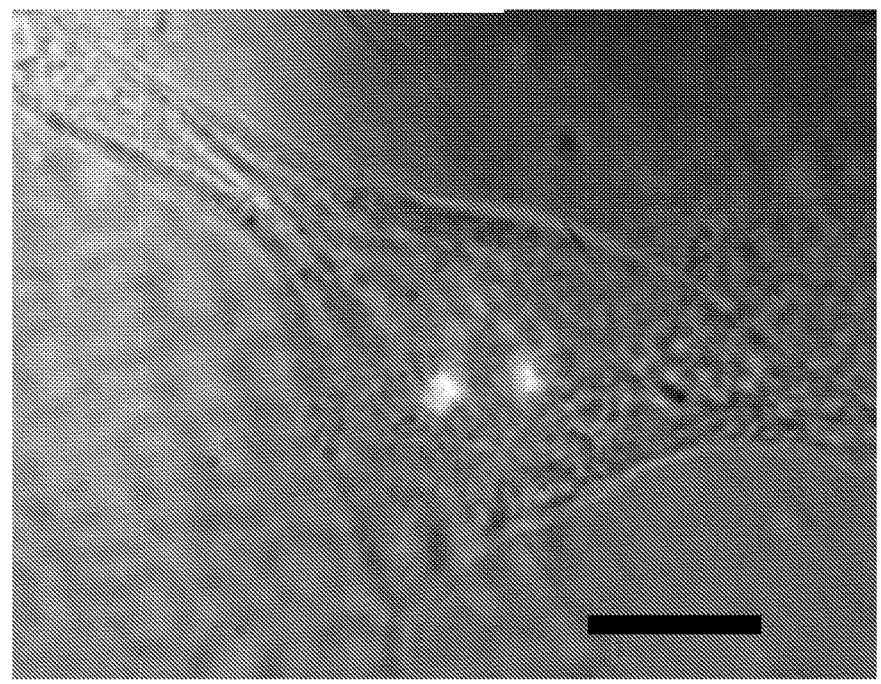
FIG. 15 is a fluorescence microscopy image of rhodamine-labeled eNPs in A549 cells 24 hours after treatment at 37° C. Scale bar=10 µm.

To confirm uptake of nanoparticles in A549 human non-small cell lung cancer cells, rhodamine labeled-nanoparticles similar to those in Example 15 were visualized with fluorescence microscopy FIG. 15. After 24 hours large (~1000 nm) fluorescent polymeric structures were observed, consistent with a swollen state of the expansile nanoparticles. Next, we quantified the eNPs cellular uptake via flow cytometry using rhodamine-labeled nanoparticles. A shift in fluorescence intensity due to the internalization of the rhodamine-eNPs was observed and the cellular level of nanoparticles progressively increased with incubation time at 37° C. with 88.3±0.8% of cells demonstrating particle uptake by 24 hours. The initial rate of eNP cellular uptake (0 to 8 hours) can be modeled linearly giving a rate of 6.3% of cells with eNP uptake per hour. As further proof of cellular uptake of nanoparticles, when cells were incubated at 4° C. to decrease metabolic activity, cellular uptake was prevented (P<0.001 for all treatment times). This reduction of intracellular eNP levels at low temperature indicates that the cellular uptake of our expansile nanoparticles is an energy-dependent process.

Example 40: Cell Proliferation Assays

In some experiments, tumor cells were washed with sterile phosphate buffered saline (PBS) and trypsinized. The cells were then counted using a Coulter counter and plated 3,000 cells/well in 96 well plates. Cells were serum starved overnight and then treated with paclitaxel, control nanoparticles, or paclitaxel loaded-nanoparticles the next day. A positive control contained 10% FBS or the same concentration of FBS provided for treated cells, while a negative control lacked FBS. At the completion of the assay the cells were incubated with 50 μl of 1× Thiazolyl Blue Tetrazolium Bromide (MTT, Sigma) dissolved in PBS at 37° C. for two hours. The media was then aspirated and 100 μl of DMSO was added to each well. The plates were then placed on a shaking device for 10 minutes and the wells turned purple, corresponding with the numbers of viable mitochondria in the well. The plates were placed on an ELISA reader and scanned at a wavelength of 570 nm. The absorbance values were normalized to values from a known number of stained cells. The dose of paclitaxel at which 50% of cells are killed, or LD50, was determined to be between 1-10 ng/mL.

In other experiments, tumor cells were washed with sterile phosphate buffered saline (PB) and trypsinized. The cells were then counted and re-plated onto 96 well plates at 2,000-3,000 cells/well. Cells were grown in media for 24 hr to allow cell adhesion before administration of treatment (e.g. unloaded-nanoparticles, drug loaded-nanoparticles, free drug, saline or other positive or negative controls). Cells were then allowed to grow without media changes for an additional 7 days before aspiration of media and replacement with 100 μL of MTS:media (1:5 vol/vol ratio). Plates were then read on a plate reader at 492 nm to determine cell viability.

Example 41: Anti-Tumor Response In Vitro

Cell proliferation assays testing the effects of paclitaxel encapsulated within nanoparticles were performed using three tumor cell lines. Lewis Lung Carcinoma (LLC), Melanoma, and Calu6 (human lung cancer) cell lines were plated at 3,000 cells/well and when established, cultured in media with/without paclitaxel. Some cultures were maintained with optimal growth factors (serum) whereas others were serum starved (non-growing) cultures. At the end of 5 days, tumor cell proliferation was assessed via MTT analysis. Data was plotted by normalization to the positive and negative control cultures as 0% and 100% inhibition, respectively. The results indicated that media containing paclitaxel at a concentration of 1-10 ng/mL reliably inhibits growth of the LLC, melanoma, and Calu6 tumor cell lines in proliferation assays. This data was obtained using media containing 10% FBS (positive control).

Cell proliferation assays were utilized to study the effects of paclitaxel-loaded nanoparticles on tumor growth. Tumor cells were plated at 3,000 cells/well and positive (serum-rich) and negative (serum-poor) cultures were used to signify 0% and 100% growth inhibition respectively. Inhibition of tumor growth was not present with control (DMSO) loaded-nanoparticle that did not contain paclitaxel. These results demonstrate that paclitaxel-loaded nanoparticles are an effective means of drug delivery and specifically result in an effective anti-tumor response in vitro.

To determine the kinetics of the anti-tumor response elicited by paclitaxel-loaded microspheres and to assess for a potential "burst effect" of drug release, a cell proliferation assay comparing paclitaxel-loaded nanoparticles and DMSO (control) nanoparticles using the melanoma cell line was run for five consecutive days with a plate undergoing MTT analysis each day for days 2-5. Paclitaxel loaded nanoparticles and DMSO nanoparticles were added to serum rich media and individually assessed on tumor cells of the same plate. The results demonstrate a dose-dependent inhibition with the administration of paclitaxel loaded-nanoparticles, but little difference in inhibition for a given dose on day 2 vs. day 5. These findings confirm that paclitaxel loaded-nanoparticles inhibit tumor growth quickly with little difference in growth inhibition following the initial exposure. This is consistent with an immediate release of drug and maximum burst effect.

Example 42: In Vitro Tumor Cytoxicity with Paclitaxel-Loaded Nanoparticles

Cultured tumor cell lines for lung (murine LLC, human A549 and NCI-H460), melanoma (B16), mesothelioma (human MSTO-211H), breast (human MCF7), and human sarcoma (LMS05) cancers were cultured at 37° C./5% $CO_2$ in the appropriate media supplemented with 10% Fetal Bovine Serum (FBS) and 1% penicillin/streptomycin with L-glutamine, with the exception of MEM media which also contained 1% essential amino acids and 1 mg/mL of bovine insulin. Each cell line was seeded at concentrations of 3,000

Figure 16:
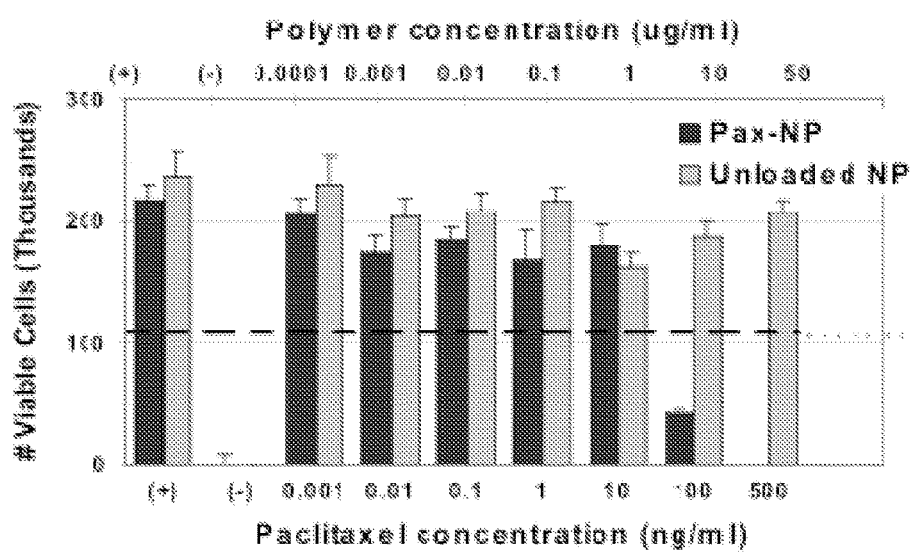
FIG. 16 is a bar graph showing the anti-cancer activity of paclitaxel loaded-nanoparticles with LLC cells in vitro.
Figure 17:
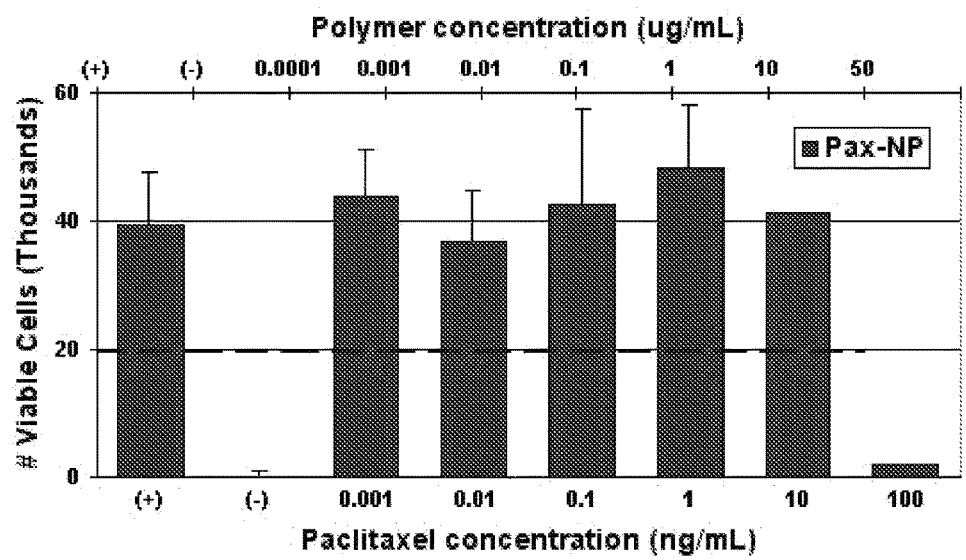
FIG. 17 is a bar graph showing activity of paclitaxel loaded nanoparticles with mesothelioma cells in vitro.
Figure 18:
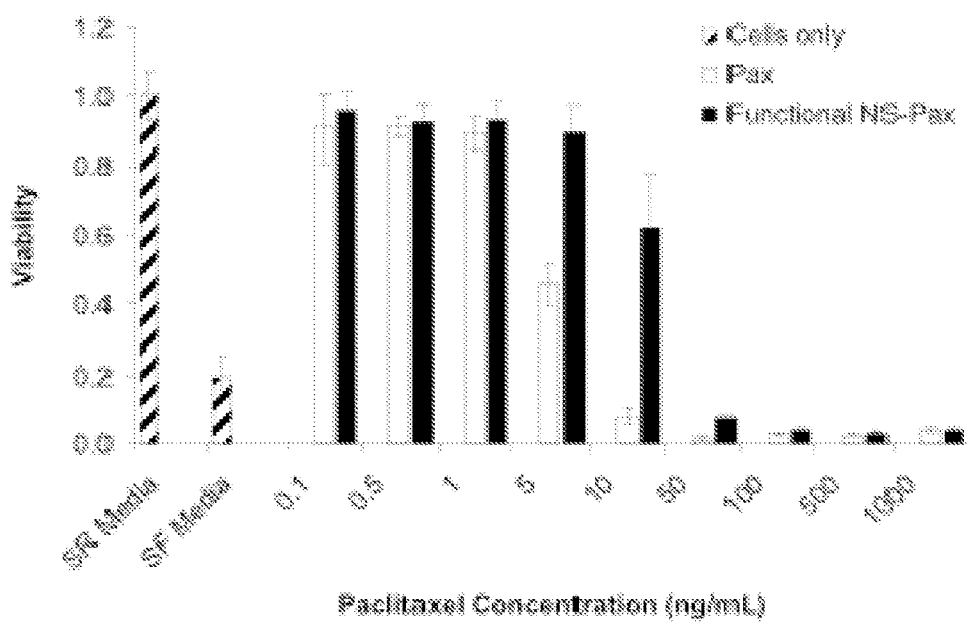
FIG. 18 is a bar graph showing the anti-cancer activity of paclitaxel loaded-nanoparticles with A459 cells in vitro.

(LLC, B16, A549, MSTO-211H, NCI-H460), 5,000 (MCF7) or 10,000 (LMSOS) cells/well into 96-well assay plates in order to establish the appropriate tumor cell plating density. Cells were co-cultured for 7 days with paclitaxel-loaded and unloaded nanoparticles such as those in Example 9 and Example 12. After the incubation period, cells were assayed for viability via MTT analysis and plotted as the percentage of viable cells using a positive control (culture containing no nanoparticles) to represent 100% viability. See FIG. 16 for results from LLC, FIG. 17 for results from MSTO-211H, and FIG. 18 for results from A549 cells that demonstrate paclitaxel-loaded, but not unloaded, nanoparticles reduce cell proliferation for several different cancer lines at concentrations as low as 10 µg/mL of polymer nanoparticles (containing approximately 10-100 ng/mL of Paclitaxel, consistent with the $IC_{50}$ of free paclitaxel).

Example 43: Nanoparticles Localize to Established Tumors after IP Injection

Figure 19:
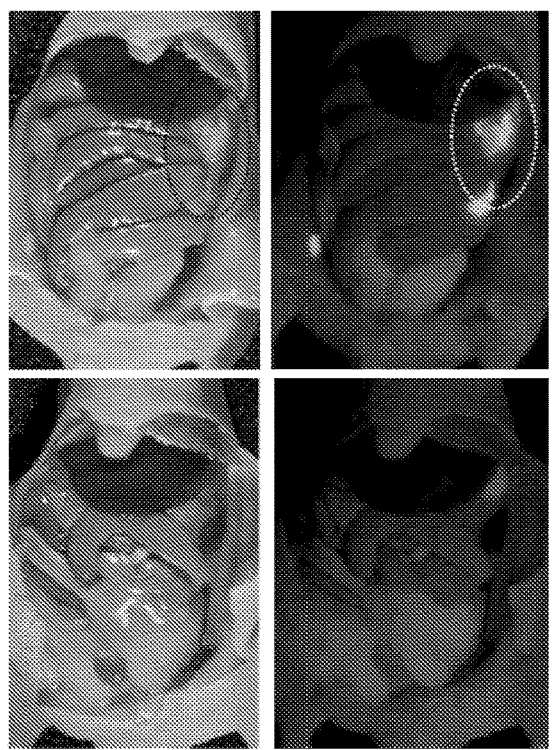
FIG. 19 shows localization of nanoparticles (Rho-eNPs) to mesothelioma tumor after IP injection (top). Image after injection of Rho alone, confirming that nanoparticles are required for localization (bottom).

The application of expansile nanoparticles to an established tumor or surgically resected tumor site and their ability to remain there is key. Recently, we observed that eNPs localize to the site of an established human mesothelioma tumor after IP administration using a established in vivo tumor murine model of mesothelioma (Colson et al., Biomaterials. 32:832-840, 2011, Adusumilli et al., J Thorac Cardiovasc Surg. 132:1179-88, 2006). This discovery was made using covalently tagged rhodamine labeled-nanoparticles (Rho-eNP), such as those in Example 15, and the fact that these NPs fluoresce under UV irradiation. Human malignant mesothelioma xenografts were established by injecting 5 million MSTO-211H cells intraperitoneally (IP) into nude mice. After 14 days, Rho-eNPs were injected IP. The mice were then sacrificed 24 hours later. Illumination under UV light showed the Rho-eNPs were localized to sites of tumor (FIG. 19).

Example 44: Anti-Tumor Response of Paclitaxel Loaded-Nanoparticles In Vivo

Figure 20:
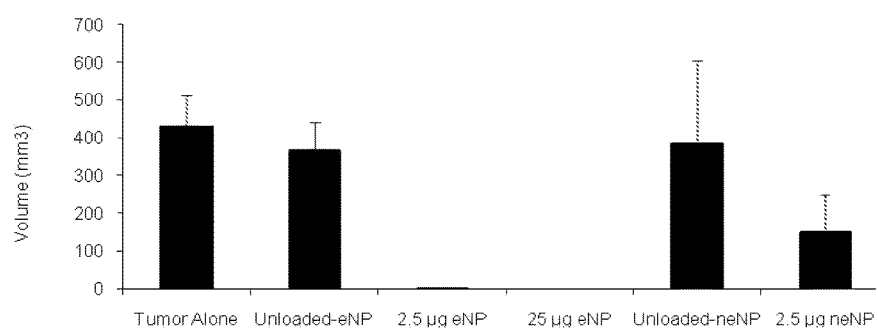
FIG. 20 is a bar graph showing that tumor volume in response to Paclitaxel loaded-nanoparticles.

The anti-tumor effects of chemotherapy-loaded nanoparticles were evaluated in well-established subcutaneous tumor models. Mouse LLC or human MSTO-211H cancer cell lines were implanted into C57BL6 or nude mice, respectively. For example, cultured LLC tumor cell suspensions were co-injected with drug-loaded nanoparticles, similar to those in Example 12, into the subcutaneous tissues on the back of mice. Both "high" (25 µg paclitaxel) and "low" (2.5 µg paclitaxel) doses of nanoparticles were evaluated. Animals injected whose tumor cells were injected alone or with unloaded expansile nanoparticles, such as those in Example 9, or Paclitaxel loaded non-expansile (non-pH-responsive) nanoparticles, such as those made from the monomer in Example 5, served as controls. Tumor size was monitored biweekly and animals were euthanized if tumors reached 2 cm in size. As demonstrated in FIG. 20, both the high and low doses of Paclitaxel loaded-expansile-nanoparticles prevented tumor growth in mice (p<<0.0001), and were more effective than the Paclitaxel loaded non-expansile nanoparticles. These data clearly demonstrate that the anti-tumor effects of paclitaxel-loaded expansile nanoparticles translate to inhibition of in vivo tumor growth.

Figure 21:
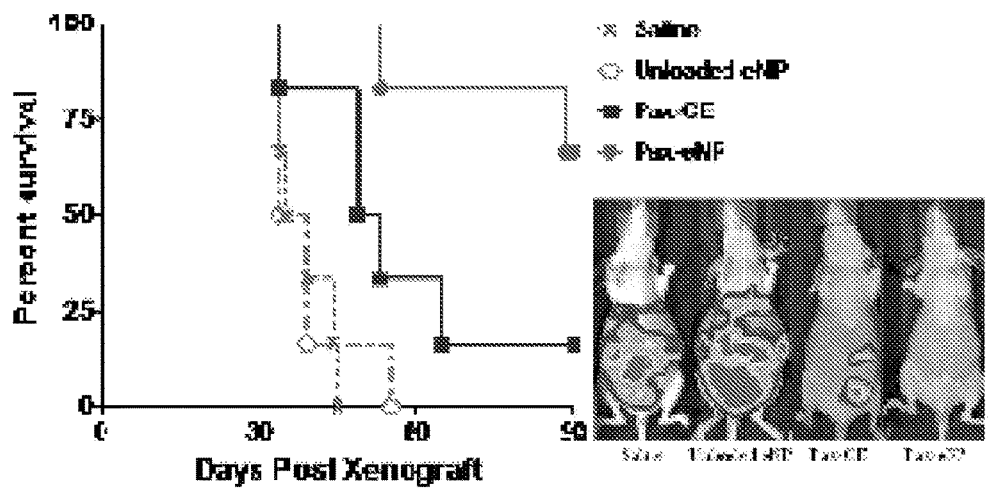
FIG. 21 shows that paclitaxel loaded-nanoparticles prolong survival in peritoneal carcinomatosis. Athymic nude mice received $5 \times 10^6$ MSTO-211H-Luc cells IP followed 7 days later by 4 weekly doses of 10 mg/kg paclitaxel as Pax-eNP (red) or in Crempahor®EL (blue). Controls received equivalent doses of unloaded-nanoparticles or saline. A representative image from bioluminescent imaging 7 days after final treatment shows tumor in all mice except those treated with Pax-eNP is also shown.

Example 45: Anti-Tumor Response of Paclitaxel Loaded-Nanoparticles in a Multiple-Dosing in Vivo Survival Study To evaluate the efficacy of Paclitaxel loaded-nanoparticles in treatment of established intraperitoneal (IP) mesothelioma, we performed the following in vivo survival study. Xenografts were established in 6-8 week old female athymic nude mice via IP injection of $5 \times 10^6$ MSTO-luc tumor cells. Seven days after xenograft establishment mice received a total of 40 mg/kg paclitaxel delivered as four weekly injections of either 1) Pax-eNP, 2) Paclitaxel in Cremophor EL/ethanol (Pax-CE), 3) an equivalent dose of unloaded eNP or 4) saline control, standardized to 500 µL volume. Animals were monitored daily until morbidity from tumor burden met humane criteria requiring sacrifice. Representative animals were evaluated using bioluminescent imaging (BLI) for comparison of tumor burden 7 days after initial treatment (FIG. 21 inset). Treatment with Pax-eNP results in superior anti-tumor efficacy against established mesothelioma and significantly improved survival in vivo (FIG. 21).

Figure 22:
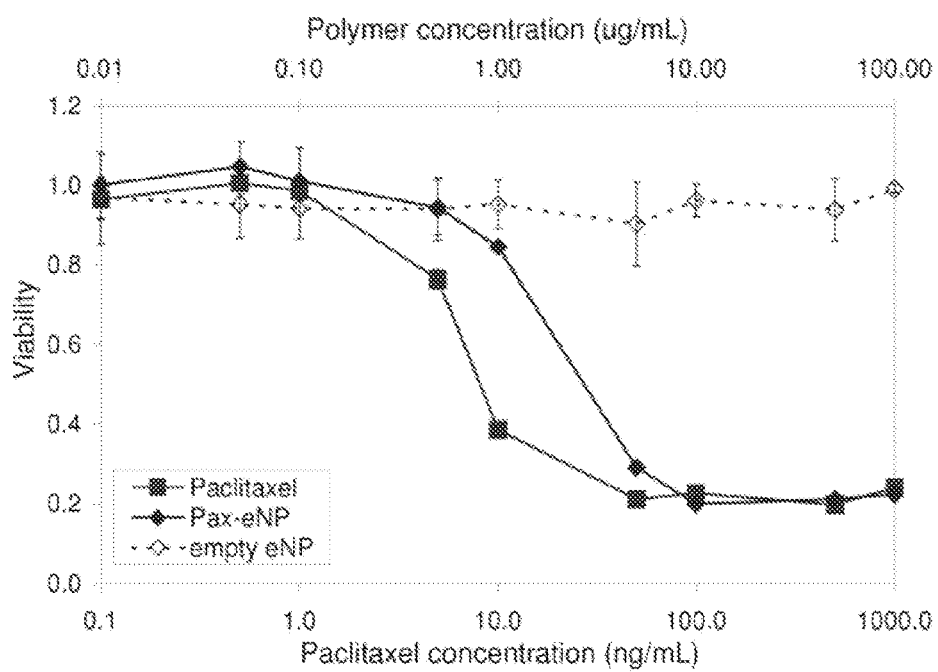
FIG. 22 is a line graph showing the percent relative viability of A549 cells following 72 hours of exposure to paclitaxel, empty expansile nanoparticles, and paclitaxel loaded expansile nanoparticles. Data displayed as mean±SD; n=3.

Example 46: In Vitro Cell Cytotoxicity of Paclitaxel Loaded-Expansile Nanoparticles Shows Depot Effect To evaluate in vitro activity, we performed cell cytotoxicity experiments with Paclitaxel loaded-eNPs, unloaded-eNPs, and paclitaxel alone against the human A549 lung cancer cell line. Upon loading the nanoparticles with paclitaxel (1 mg of polymer contains 10 ng of paclitaxel) we observed a dose dependent decrease in cell viability with an $IC_{50}$ value between 1 and 10 ng/mL (FIG. 22). Co-culture of A549 cells with the unloaded eNPs, did not result in tumor cytotoxicity, demonstrating that cell death was due to paclitaxel release and not exposure to the polymer itself. The shift of the curve, and corresponding increase in $IC_{50}$ value for the Paclitaxel loaded-eNPs indicates that more paclitaxel must be given to afford the same cytotoxic effect—i.e., less Paclitaxel is bioavailable when delivered using the eNPs. The explanation for this observation is that once the eNP is in the cell, it swells, and acts like a hydrogel or sponge/depot for Paclitaxel. Such an intracellular drug depot, we hypothesize, would decrease the immediate bioavailability of Paclitaxel leading to a higher $IC_{50}$ initially, but would also lead to more paclitaxel residing in the cell and prolonged long-term effect.

Figure 23:
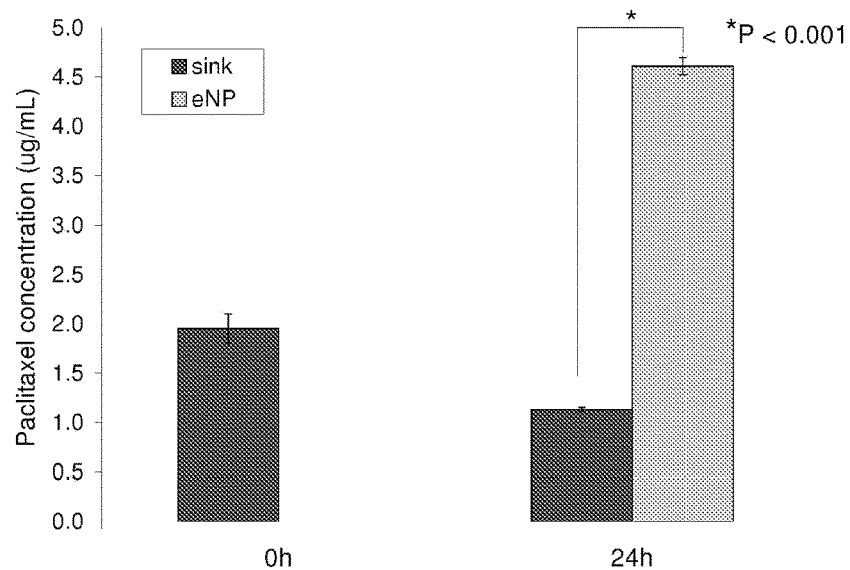
FIG. 23 is a bar graph showing paclitaxel concentration in swollen expanded nanoparticle (eNP) phase compared to aqueous buffer (sink) phase after 24 hours. Data displayed as mean±SD; n=3.

Example 47: Drug Depot Capability of Unloaded-Nanoparticles Measured by Partitioning from an Aqueous Sink To quantify the ability of the eNPs to act as a paclitaxel depot, expansile nanoparticles without drug were added to a pH 5 acetate buffer and incubated at 37° C. for 24 hours to initiate swelling. An aliquot of the expanded eNPs was then placed in 10,000 MWCO dialysis tubing and dialyzed against a 10 mM pH 7.4 phosphate buffer sink containing 2 µg/mL paclitaxel. After dialysis at 37° C. for 24 hours, aliquots were taken of both the sink and the expanded nanoparticle phase and analyzed for Paclitaxel concentration via HPLC. FIG. 23 shows that at 24 hours, the Paclitaxel preferentially partitioned to the swollen nanoparticle phase with a four-fold increase of Paclitaxel in the expanded nanoparticle phase and a log D-value of 0.61±0.001. This partitioning indicates that swollen expansile particles may act as intracellular paclitaxel depots increasing and prolonging a cell's exposure to the drug.

Figure 24:
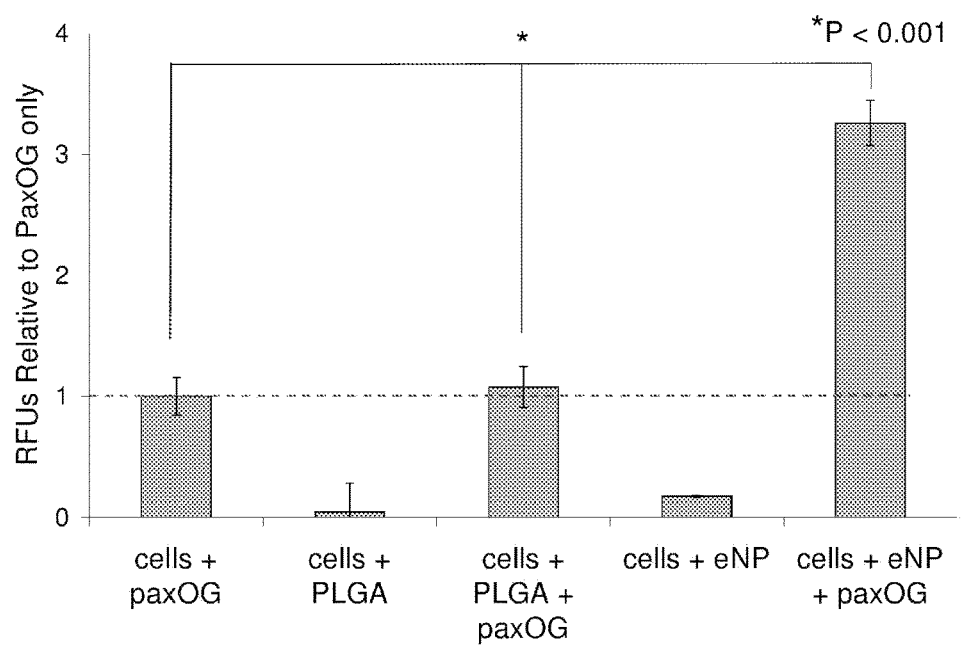
FIG. 24 is a bar graph showing the relative uptake of Paclitaxel-OREGON GREEN® (PaxOG) in untreated cells, cells treated with conventional PLGA-NPs, or cells treated with expansile nanoparticles (eNPs). Data displayed as mean±SD; n=3.

Example 48: Drug Depot Capability of Unloaded Expansile Nanoparticles for Paclitaxel within Cells In order to monitor the intracellular depot capability of the expansile nanoparticles, we performed a similar experiment as in Example 47 but measured uptake of paclitaxel-OREGON GREEN® (PaxOG) in the A549 lung cancer cells. After plating at 24,000 cells/mL on a 24-well plate and allowing the cells to adhere for 24 hours, cells were treated for an additional 24 h with media alone, media containing eNPs, or media containing PLGA-NPs. The cells were then washed with PBS, and incubated for 4 hours with either media alone or media containing paclitaxel-OREGON GREEN®. After 4 hours, the media was aspirated and the cells were washed 2× with PBS before being trypsinized and replated in a new 24-well plate. A fluorescence plate reader was then used to measure fluorescence ($\lambda_{ex}$=488 nm; $\lambda_{em}$ 518 nm). As shown in FIG. 24, a 3-fold increase in cellular uptake of PaxOG was noted in cells that were first treated with eNPs compared to both non-NP treated cells and cells treated with conventional PLGA NPs. Finally, to visualize the nanoparticles acting as intracellular depots, we repeated the previous experiment treating A549 cells first with rhodamine-tagged unloaded particles for 24 h before treating with paclitaxel-OREGON GREEN® for an additional 4 h. Confocal microscopy images showed co-localization of the PaxOG and eNPs.

Figure 25:
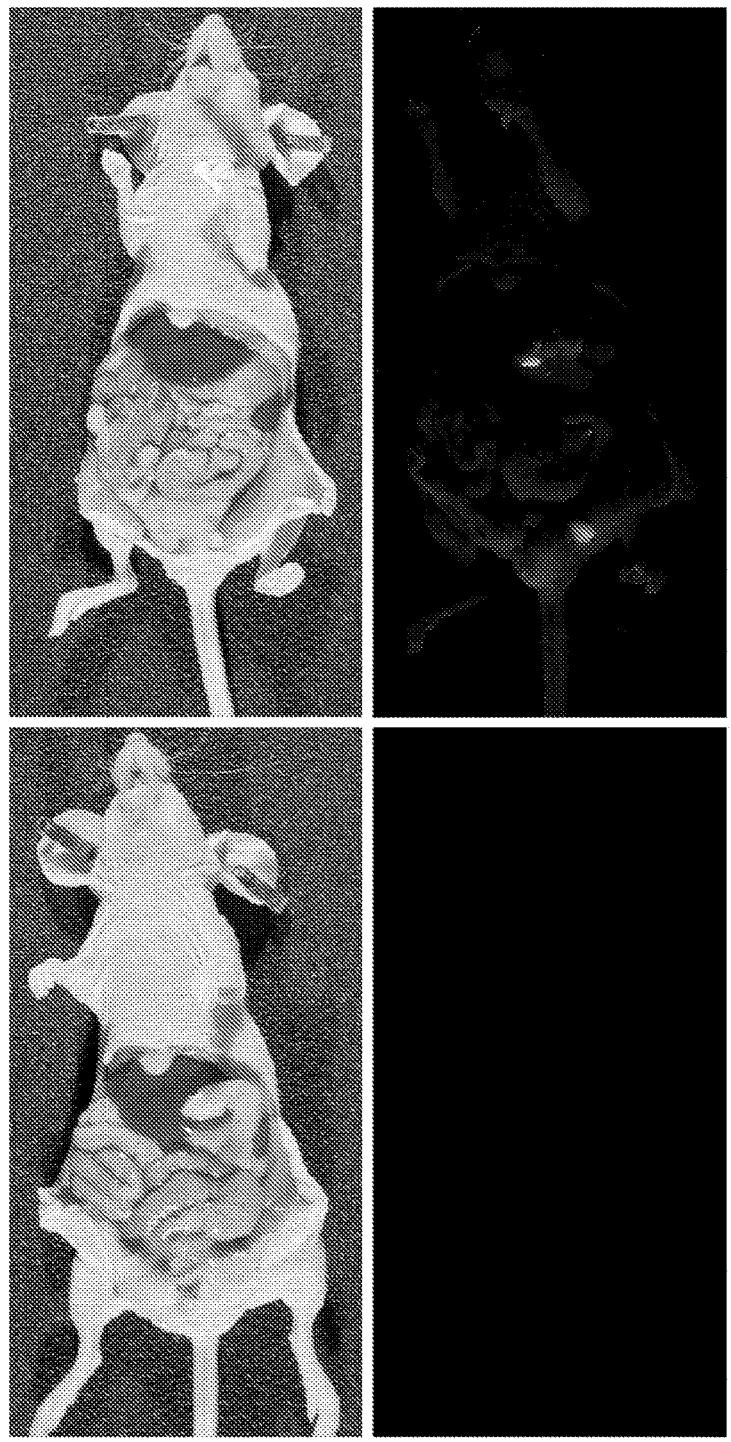
FIG. 25 shows that fluorescently labeled Paclitaxel localized at the tumor site only in the animals treated with eNPs prior to drug delivery. Athymic nude mice were injected with $5\times10^6$ mesotheliomatumor cells intraperitoneally (IP). After 7 days, eNPs (top) or saline (bottom) were injected IP followed 72 hours later by the IP injection of Paclitaxel-OREGON GREEN®. The mice were then sacrificed 48 hours later and illuminated under UV light.
Figure 26:
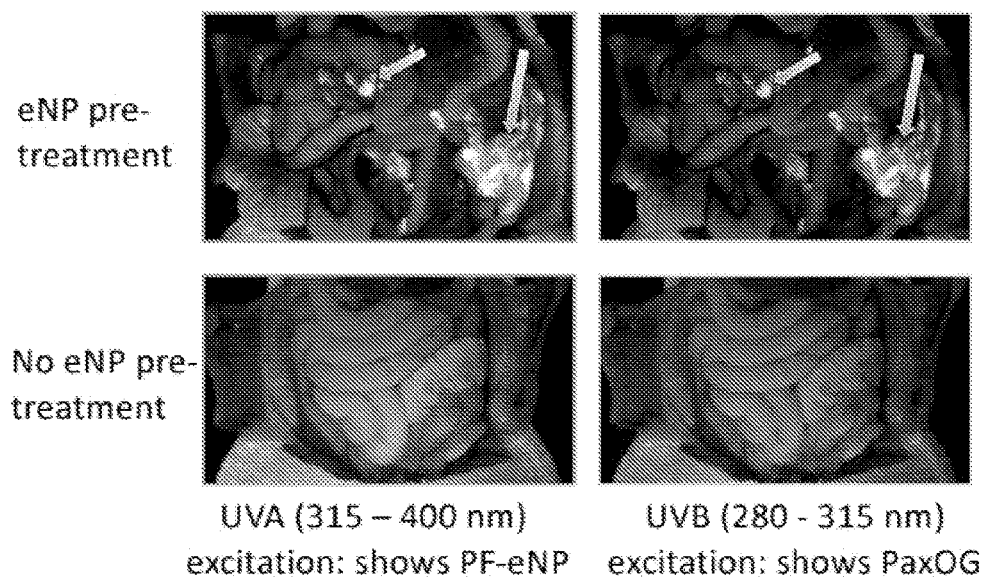
FIG. 26 shows in vivo assessment of the depot effect. To assess eNPs as drug depots in vivo, MSTO-211H cells were injected into the intraperitoneal (IP) space in mice. After allowing 7 d for tumor establishment, fluorescently (polyfluor407, PF) labeled PF-eNPs or saline were injected IP. Forty eight hours later, allowing time for eNP localization to regions of IP tumor, PaxOG in Cremophor/Ethanol was injected IP and a further 24 h given for PaxOG accumulation in eNPs and clearance of free drug. Animals were sacrificed and imaged under normal light (to visualized tumors) and UVA excitation (to visualized PaxOG). As can be seen eNP (blue) and PaxOG (green) co-localized with the tumor (arrows). However, without eNP pre-treatment (no blue), no PaxOG signal (green) was observed in the tumor.
Figure 27:
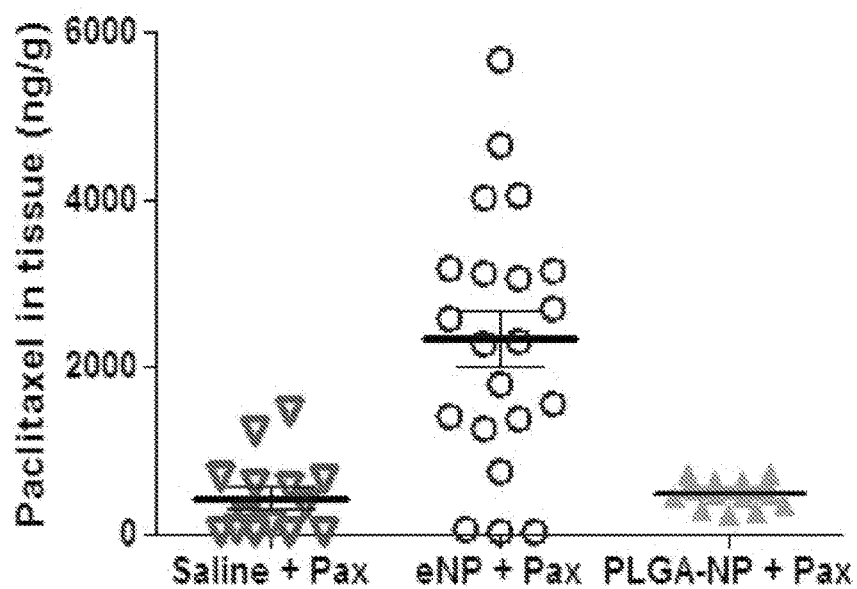
FIG. 27 shows the in vivo quantification of the depot effect. To quantify eNPs as drug depots in vivo, MSTO-211H cells were injected into the intraperitoneal (IP) space in mice. After allowing 11 d for tumor establishment, eNPs or PLGA NPs (control) or saline (control) were injected IP. Forty-eight hours later, allowing time for NP localization to regions of IP tumor, Pax in Cremophor/Ethanol was injected IP and a further 72 h given for Pax accumulation in eNPs and clearance of free drug. Animals were sacrificed and tumors harvested, and Pax quantified by LCM. As seen, significantly ($P<0.05$) more paclitaxel accumulated in the tumor tissue of mice receiving a pre-treatment of eNPs than in mice receiving a PLGA NP pre-treatment or no NP pre-treatment at all.
Figure 28:
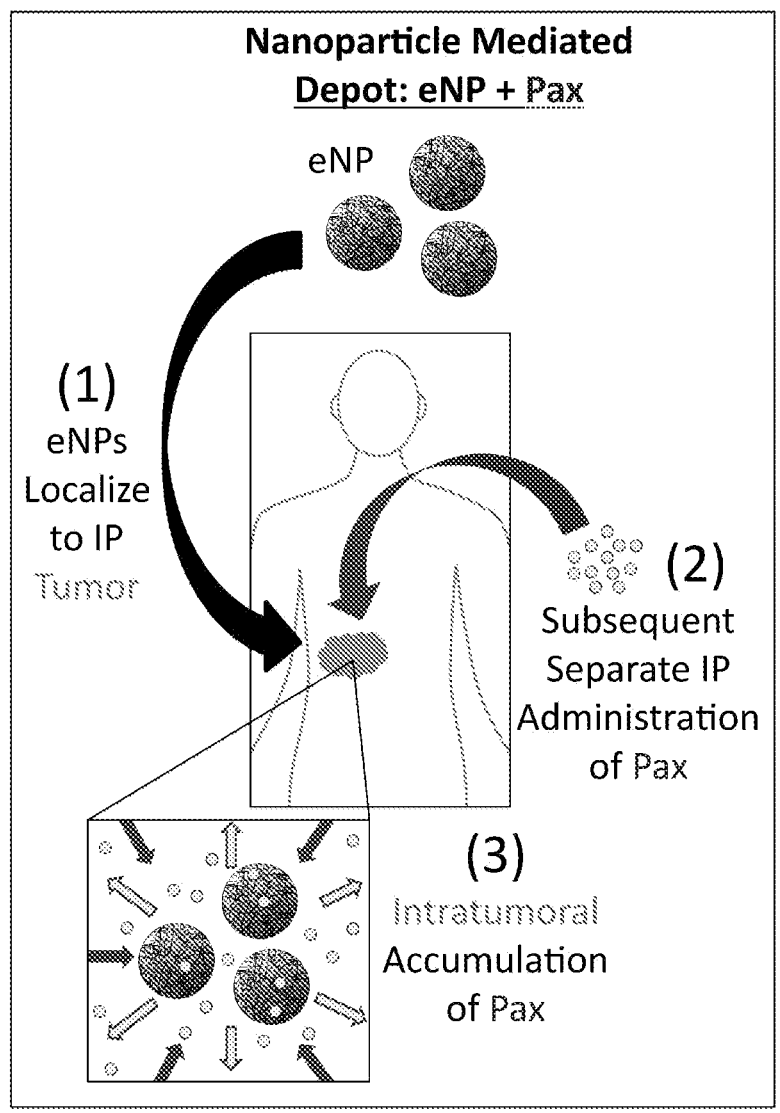
FIG. 28 is a schematic representation of an embodiment of the method described herein illustrating mechanisms of Paclitaxel (Pax) delivery to an in vivo depot for subsequent concentration of intracavitary paclitaxel (eNPs+Pax). Generally, unloaded "carriers" (eNPs) are injected alone. Free drug is separately & subsequently injected and the free drug concentrates into the "carrier" in situ.

Example 49: Unloaded-Expansile-Nanoparticles Localize to Established Tumors after IP Injection and then Concentrate Subsequently Delivered Paclitaxel to the Tumor This example illustrates application of eNPs to an established tumor or surgically resected tumor site and their ability to remain there and act as a drug depot for subsequent delivery of an agent. Human malignant mesothelioma xenografts were established intraperitoneally (IP) in nude mice as Example 45. After 7 days, eNPs, such as those prepared in Example 9, were injected IP followed 72 hours later with the IP injection of Paclitaxel-OREGON GREEN®. The mice were then sacrificed 48 hours later and illumination under UV light showed the fluorescently labeled paclitaxel localized or concentrated at the tumor site. A control experiment was also performed where mice were given the Paclitaxel-OREGON GREEN® via IP injection but not the eNPs. The mice were then sacrificed 48 hours later and illumination under UV light showed no fluorescently labeled paclitaxel at the tumor site (FIG. 25).

All patents and other publications identified in the specification and examples are expressly incorporated herein by reference for all purposes. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

What is claimed is:

1. A method of administering an agent to a tissue location in a subject, the method comprising administering to the subject polymeric particle prior to, or after administering said agent to the subject, wherein said agent is administered without the polymeric particle and the polymeric particle does not include any therapeutic agent or diagnostic agent when the polymeric particle is administered, wherein the polymeric particle comprises an oligomer or a polymer comprising a monomer represented by Formula XX:

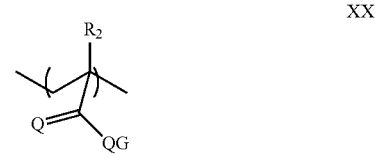

wherein:

Q is selected from the group consisting of O, S, Se, and NH;

G is selected from the group consisting of the following structures:

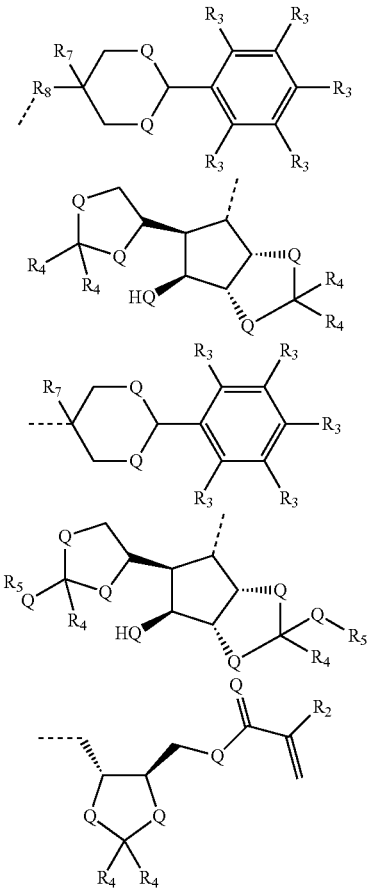

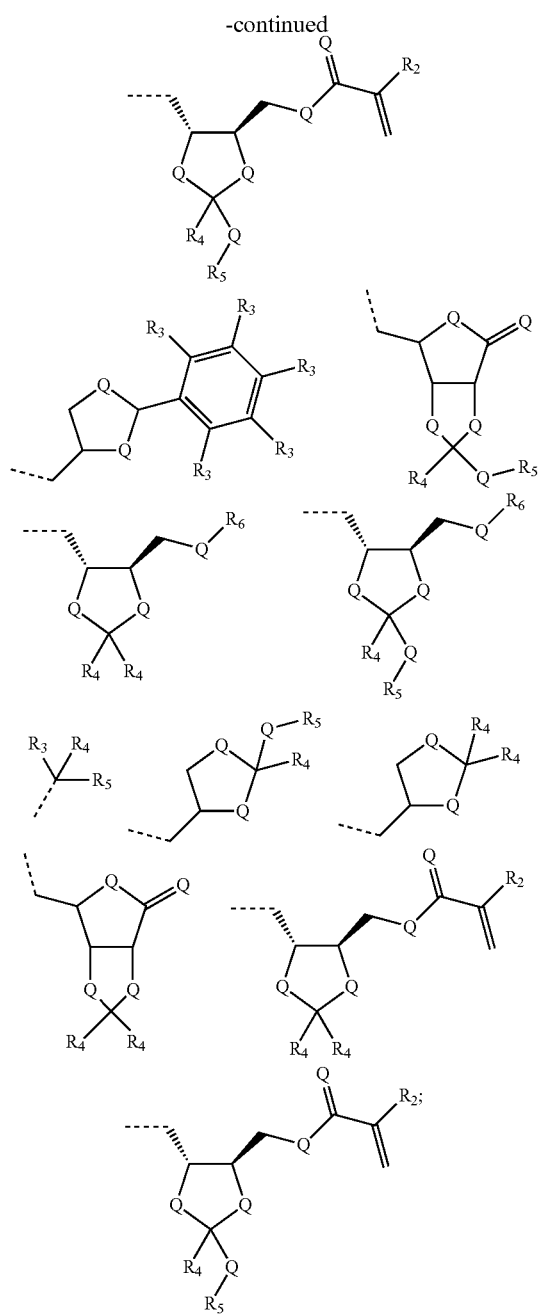

$R_2$ is selected from the group consisting of hydrogen, a straight or branched alkyl, cycloalkyl, aryl, olefin, silyl, alkylsilyl, arylsilyl, alkylaryl, arylalkyl, and fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

one $R_3$ is selected from the group consisting of methoxy, ethoxy, amino, nitro, cycloalkyl, aryl, olefin, silyl, alkylsilyl, arylsilyl, alkylaryl, and arylalkyl chain of 1-10 carbons;

and the remaining $R_3$ are each independently selected from the group consisting of hydrogen, methoxy, ethoxy, amino, a straight and branched alkyl, cycloalkyl, aryl, olefin, silyl, alkylsilyl, arylsilyl, alkylaryl, and arylalkyl chain of 1-10 carbons;

$R_4$, $R_5$, and $R_6$ are each independently selected from the group consisting of a straight or branched alkyl, cycloalkyl, aryl, olefin, silyl, alkylsilyl, arylsilyl, alkylaryl, and arylalkyl chain of 1-10 carbons; and $R_7$ and $R_8$ are each independently selected from the group consisting of hydrogen, a straight or branched alkyl, cycloalkyl, aryl, olefin, alkylaryl, and arylalkyl chain of 1-50 carbons, wherein each alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

2. The method of claim 1, wherein the agent is a therapeutic agent or a diagnostic agent.

3. The method of claim 2, wherein the agent is selected from anticancer agents, immune modulator agents, anti-inflammatory agents, antibiotics, and any combinations thereof.

4. The method of claim 1, wherein the oligomer or the polymer comprises the monomer

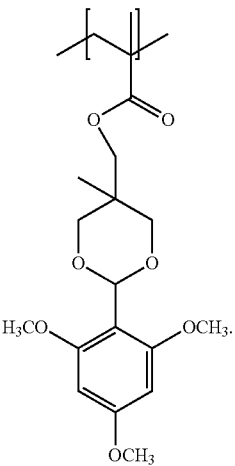

5. The method of claim 1, wherein the polymeric particle further comprises a microparticle or a nanoparticle.

6. The method of claim 1, wherein the subject is in need of treatment for cancer, recurrence of a malignancy, lymph node metastasis, inflammation, infection, wound healing, abnormal scar formation, a chronic condition, or post-operative pain.

7. A method of treating a cancer or tumor in a subject, the method comprising administering to the subject in need thereof polymeric particle prior to, or after administering an anti-cancer agent, wherein said anti-cancer agent is administered without the polymeric particle and the polymeric particle does not include any therapeutic agent or diagnostic agent when the polymeric particle is administered, wherein the polymeric particle comprises an oligomer or a polymer comprising a monomer represented by Formula XX:

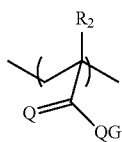

XX wherein:
Q is selected from the group consisting of O, S, Se, and NH;
G is selected from the group consisting of the following structures:

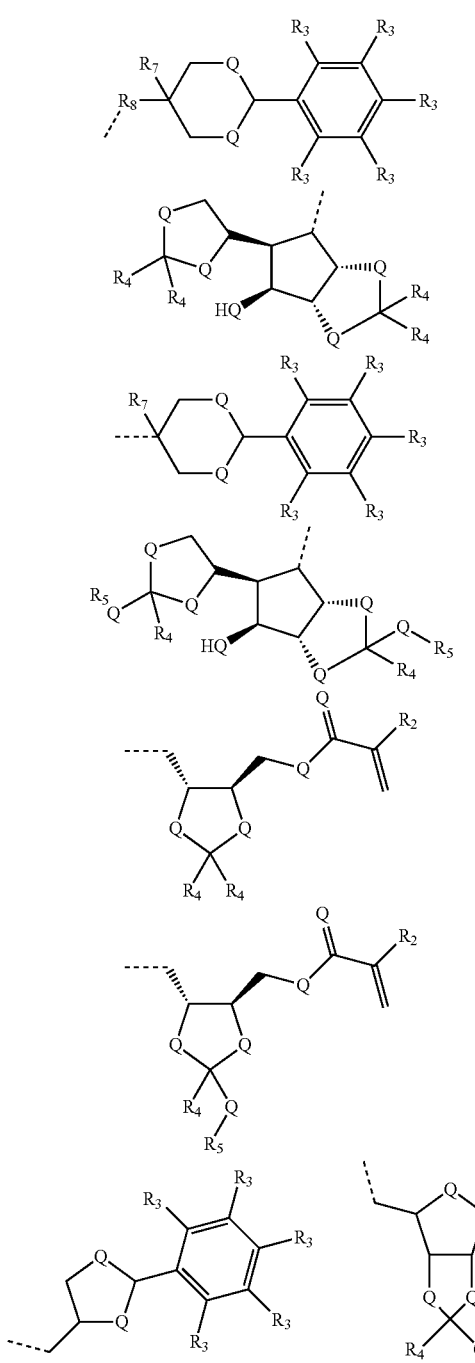

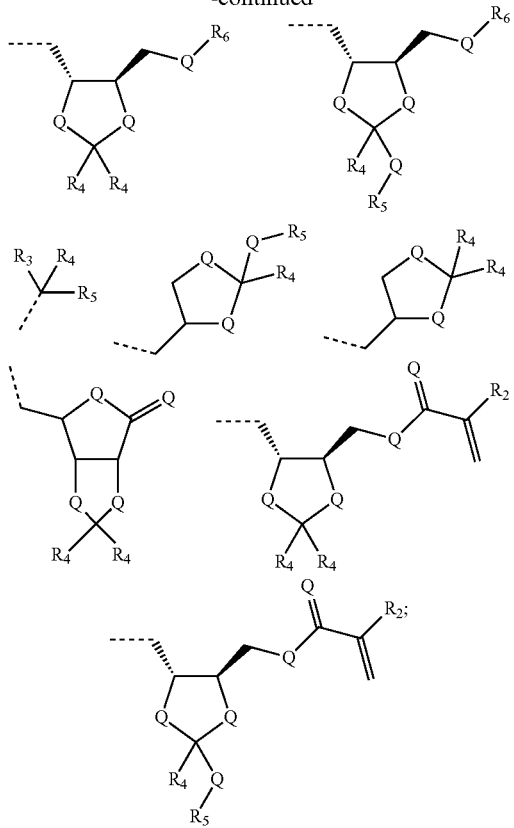

R$_2$ is selected from the group consisting of hydrogen, a straight or branched alkyl, cycloalkyl, aryl, olefin, silyl, alkylsilyl, arylsilyl, alkylaryl, arylalkyl, and fluorocarbon chain of 1-50 carbons, wherein each alkyl, cycloalkyl, aryl, olefin, silyl, alkylsilyl, arylsilyl, alkylaryl, arylalkyl, or fluorocarbon chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents;

one R$_3$ is selected from the group consisting of methoxy, ethoxy, amino, nitro, cycloalkyl, aryl, olefin, silyl, alkylsilyl, arylsilyl, alkylaryl, and arylalkyl chain of 1-10 carbons;

and the remaining R$_3$ are each independently selected from the group consisting of hydrogen, methoxy, ethoxy, amino, a straight and branched alkyl, cycloalkyl, aryl, olefin, silyl, alkylsilyl, arylsilyl, alkylaryl, and arylalkyl chain of 1-10 carbons;

R$_4$, R$_5$, and R$_6$ are each independently selected from the group consisting of a straight or branched alkyl, cycloalkyl, aryl, olefin, silyl, alkylsilyl, arylsilyl, alkylaryl, and arylalkyl chain of 1-10 carbons; and R$_7$ and R$_8$ are each independently selected from the group consisting of hydrogen, a straight or branched alkyl, cycloalkyl, aryl, olefin, alkylaryl, and arylalkyl chain of 1-50 carbons, wherein each alkyl, cycloalkyl, aryl, olefin, alkylaryl, or arylalkyl chain is optionally substituted internally or terminally by one or more hydroxyl, hydroxyether, carboxyl, carboxyester, carboxyamide, amino, mono- or di-substituted amino, thiol, thioester, sulfate, phosphate, phosphonate, or halogen substituents.

8. The method of claim 7, wherein the tumor is a malignant tumor, a benign tumor, a primary tumor or a metastatic tumor.

9. The method of claim 7, wherein the polymeric particle comprises an oligomer or a polymer comprising the monomer

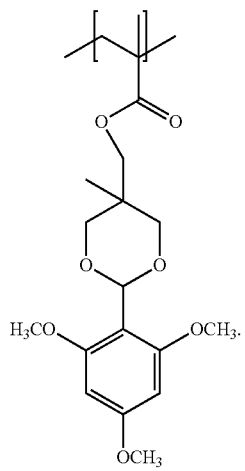

10. The method of claim 1, wherein the polymeric particle comprises an oligomer or polymer comprising the cross linker:

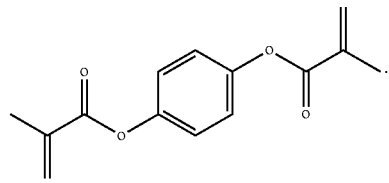

11. The method of claim 1, wherein the polymeric particle comprises an oligomer or polymer comprising a monomer of formula:

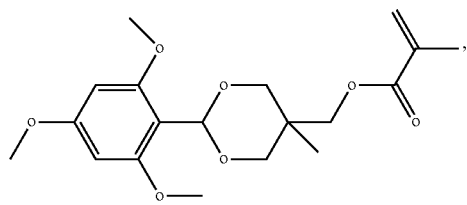

and a cross-linker monomer of formula:

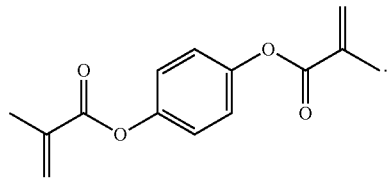 [SMILES: C=C(C)C(=O)Oc1ccc(OC(=O)C(=C)C)cc1]

12. The method of claim 9, wherein the polymeric particle comprises an oligomer or polymer comprising the cross linker:

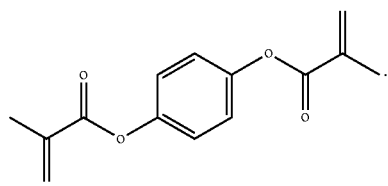

13. The method of claim 7, wherein the polymeric particle comprises an oligomer or polymer comprising a monomer of formula:

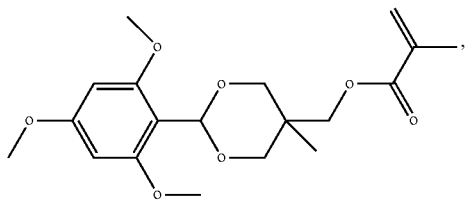

and a cross-linker monomer of formula:

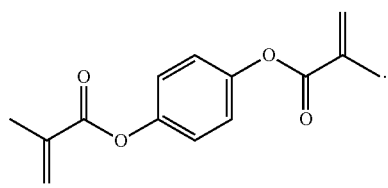

* * * * *